US011970479B2

(12) United States Patent
Acton, III et al.

(10) Patent No.: US 11,970,479 B2
(45) Date of Patent: *Apr. 30, 2024

(54) 3-(1H-PYRAZOL-4-YL)PYRIDINE ALLOSTERIC MODULATORS OF THE M4 MUSCARINIC ACETYLCHOLINE RECEPTOR

(71) Applicants: Merck Sharp & Dohme LLC, Rahway, NJ (US); MSD R&D (China) Co. LTD., Shanghai (CN)

(72) Inventors: John J. Acton, III, Cranford, NJ (US); Melissa Egbertson, Ambler, PA (US); Xiaolei Gao, Bridgewater, NJ (US); Scott T. Harrison, Elkins Park, PA (US); Timothy J. Henderson, Natick, MA (US); Michael Man-Chu Lo, Bedminster, NJ (US); Robert D. Mazzola, Jr., Stewartsville, PA (US); Zhaoyang Meng, Ambler, PA (US); James Mulhearn, Elkins Park, PA (US); Vanessa L. Rada, Hatfield, PA (US); Jeffrey W. Schubert, North Wales, PA (US); Oleg B. Selyutin, West Windsor, NJ (US); David M. Tellers, Lansdale, PA (US); Ling Tong, Warren, NJ (US); Fengqi Zhang, Edison, NJ (US); Jianming Bao, South San Francisco, CA (US); Chunsing Li, Shanghai (CN)

(73) Assignees: Merck Sharp & Dohme LLC, Rahway, NJ (US); MSD R&D (China) Co. LTD., Shanghai (CN)

( * ) Notice: Subject to any disclaimer, the term of this patent is extended or adjusted under 35 U.S.C. 154(b) by 422 days.

This patent is subject to a terminal disclaimer.

(21) Appl. No.: 17/286,591

(22) PCT Filed: Oct. 24, 2019

(86) PCT No.: PCT/US2019/057746
§ 371 (c)(1),
(2) Date: Apr. 19, 2021

(87) PCT Pub. No.: WO2020/092102
PCT Pub. Date: May 7, 2020

(65) Prior Publication Data
US 2021/0395224 A1 Dec. 23, 2021

(30) Foreign Application Priority Data
Oct. 29, 2018 (WO) ............... PCT/CN18/112403

(51) Int. Cl.
*C07D 401/14* (2006.01)
*C07D 405/14* (2006.01)
(52) U.S. Cl.
CPC ......... *C07D 401/14* (2013.01); *C07D 405/14* (2013.01)

(58) Field of Classification Search
CPC ...... C07D 401/14; C07D 405/14; A61P 25/00
See application file for complete search history.

(56) References Cited

U.S. PATENT DOCUMENTS

| | | |
|---|---|---|
| 10,329,289 B2 | 6/2019 | Bao |
| 10,351,564 B2 | 7/2019 | Gao |
| 10,512,638 B2 | 12/2019 | Rudd |
| 10,836,775 B2 | 11/2020 | Gao et al. |
| 10,945,771 B2 | 3/2021 | Clausen et al. |
| 11,149,036 B2 * | 10/2021 | Acton, III ............... A61P 25/00 |
| 2016/0333021 A1 | 11/2016 | Mandal et al. |
| 2019/0315708 A1 | 10/2019 | Bao et al. |
| 2020/0095261 A1 | 3/2020 | Gao et al. |
| 2020/0109137 A1 | 4/2020 | Bao et al. |
| 2020/0207758 A1 * | 7/2020 | Acton, III ............ C07D 498/04 |

FOREIGN PATENT DOCUMENTS

| | | | | |
|---|---|---|---|---|
| WO | WO-2017107089 A1 * | 6/2017 | ........... | A61K 31/437 |
| WO | 2018023081 A1 | 2/2018 | | |
| WO | 2019005587 A1 | 1/2019 | | |

OTHER PUBLICATIONS

Antipsychotic Drug-Like Effects of the Selective M4 Muscarinic Acetylcholine Receptor Positive Allosteric N. Byun et al., 39 Neuropsychopharmacology, 1578-1593 (2014) (Year: 2014).*
Allosteric activation of M4 muscarinic receptors improve behavioral and physiological alterations in early symptomatic YAC128 mice T. Pancani et.al., 112, Proc Natl Acad Sci U S A., 14078-83 (2015). (Year: 2015).*
Muscarinic acetylcholine receptor expression in memory circuits:Implications for treatment of Alzheimer disease A.I. Levery, 93, Proc Natl Acad Sci U S A., 13541-46 (1996). (Year: 1996).*
Selective Activation of M4 Muscarinic Acetylcholine Receptors Reverses MK-801-Induced Behavioral Impairments and Enhances Associative Learning in Rodents M. Bubser et.al. 5, ACS Chem Neurosci, 920-42 (2014). (Year: 2014).*

(Continued)

*Primary Examiner* — Theodore R. Howell
*Assistant Examiner* — Pierre P Eleniste
(74) *Attorney, Agent, or Firm* — Eric A. Meade; John C. Todaro

(57) ABSTRACT

The present invention is directed to cinnolinyl and quinolinyl pyrazol-4-yl-pyridine compounds which are allosteric modulators of the M4 muscarinic acetylcholine receptor. The present invention is also directed to uses of the compounds described herein in the potential treatment or prevention of neurological and psychiatric disorders and diseases in which M4 muscarinic acetylcholine receptors are involved. The present invention is also directed to compositions comprising these compounds. The present invention is also directed to uses of these compositions in the potential prevention or treatment of such diseases in which M4 muscarinic acetylcholine receptors are involved.

18 Claims, No Drawings

(56) References Cited

OTHER PUBLICATIONS

Birdsall, Multiple Allosteric Sites on Muscarinic Receptors, NPL-Birdsall-2001-2517, 2001, 2517-2524, 58, Life Science.
Bodick, Neil C. et al., Effects of Xanomeline, a Selective Muscarinic Receptor Agonist, on Cognitive Function and Behavioral Symptoms in Alzheimer Disease, Arch Neurol., 1997, 465-473, 54.
Brauner-Osborne, Pharmacology of Muscarinic Acetylcholine Receptor Subtypes (ml-m5): High Throughout Assays in Mammalian Cells, E. Journal of Pharmacology, 1996, 93-102, 295.
Carruthers, Sean P. et al., The muscarinic system, cognition and schizophrenia, Neuroscience and Biobehavioral Reviews, 2015, 393-402, 55.
Caufield, Muscarinic Receptors Characterization, Coupling and Function, uscarinic Receptors Characterization, Coupling and Function, 1993, 319-379, 58, Pharmac. Ther.
Christopoulos, Allosteric Binding Sites on Cell-Surface Receptors: Novel Targets for Drug Discovery, Nature, 2002, 198-210, 1.
Coward, Peter et al., Chimeric G Proteins Allow a High-Throughput Signaling Assay of Gi-Coupled Receptors, Analytical Biochemistry, 1999, 242-248, 270.
Jones, Carrie K. et al., Muscarinic and Nicotinic Acetylcholine Receptor Agonists and Allosteric Modulators for the Treatment of Schizophrenia, Neuropsychopharmacology, 2012, 16-42, 37.
Lazareno, Analogs of WIN 62,577 Define a Second Allsoteric Site on Muscarinic Receptors, Molecular Pharmacology, 2002, 1492-1505, 62.
Pubchem Compound Record for CID 118265914, 4-Quinolin-7-yl-3-(2H-tetrazol-5-yl)pyridine-2-sulfonamide, U.S. National Library of Medicine, Feb. 23, 2016, pp. 1-22; p2 (https://pubchem.ncbi.nlm.nih.gov/compound/118265914).
Pubmed Compound Record for CID 118019076, 1-[4-[6-Chloro-7[2-(1H-pyrazol-4-yl)phenyl]quinazolin-4-yl]piperazin-1-yl]prop-2-en-1-one, U.S. National Library of Medicine, Feb. 23, 2016, pp. 1-20; p2 (https://pubchem.ncbi.nlm.nih.gov/compound/118019076).
Pubmed Compound Record for CID 90094904, 6-[3-(6-Methylpyridin-2-yl)pyridin-2-yl]quinoxaline, U.S. National Library of Medicine, Feb. 13, 2015, pp. 1-20; p2 (https://pubchem.ncbi.nlm.nih.gov/compound/90094904).
Schubert, Jeffrey W. et al., Discovery, Optimization, and Biological Characterization of 2,3,6-Trisubstituted Pyridine-Containing M4 Positive Allosteric Modulators, ChemMedChem, 2019, 943-951, 14.
Spalding et al., Discovery of an Ectopic Activation Site on the M1 Muscarinic Receptor, Site on the M1 Muscarinic Receptor, 2002, pp. 1297-1302, 61, Molecular Pharmacology, US.

* cited by examiner

3-(1H-PYRAZOL-4-YL)PYRIDINE ALLOSTERIC MODULATORS OF THE M4 MUSCARINIC ACETYLCHOLINE RECEPTOR

CROSS REFERENCE TO RELATED APPLICATIONS

This application is a U.S. National Phase application under 35 U.S.C. § 371 of PCT Application No. PCT/US2019/057746, filed Oct. 24, 2019, which claims priority under 35 U.S.C. § 119(e) from PCT/CN2018/112403, filed Oct. 29, 2018.

BACKGROUND OF THE INVENTION

Acetylcholine (ACh) is a key neurotransmitter that modulates neuronal function in the peripheral nervous system (PNS) and central nervous system (CNS). ACh mediates its actions via two families of receptors, termed the muscarinic ACh receptors (mAChRs) and the nicotinic ACh receptors (nAChRs). A large body of evidence suggests that basal forebrain cholinergic neurons and basalo-cortical cholinergic pathways are selectively vulnerable to degeneration in Alzheimer's disease. It has therefore been hypothesized that cholinergic hypofunction contributes to the cognitive deficits of patients suffering from Alzheimer's disease. Consequently, acetylcholinesterase inhibitors, which inhibit ACh hydrolysis and potentiate cholinergic signaling have been demonstrated to not only provide improvements in cognitive symptoms associated with Alzheimer's disease, but also show efficacy in treating the psychiatric symptoms. Acetylcholinesterase inhibitors, however, have not been shown to change the underlying disease pathology.

Another potential pharmacotherapeutic target to counteract cholinergic hypofunction is the activation of muscarinic acetylcholine receptors (mAChRs). Muscarinic acetylcholine receptors are members of the G protein-coupled receptor superfamily which mediate the actions of the neurotransmitter acetylcholine in both the central and peripheral nervous system. Muscarinic acetylcholine receptors are prevalent throughout the body and five distinct muscarinic receptors (M1-M5) have been identified in mammals. The muscarinic receptors are known to contain one or more allosteric sites which may alter the affinity with which muscarinic ligands bind to the primary binding or orthosteric sites. In the central nervous system, muscarinic receptors are involved in cognitive, behavior, sensory, motor and autonomic functions. The M4 muscarinic acetylcholine receptor is predominantly expressed in the striatum, but also in the hippocampus and cortex.

Muscarinic receptors in the central nervous system play a critical role in mediating higher cognitive processing and control of dopamine release. Administration of nonselective muscarinic antagonists can induce cognitive deficits and psychosis in humans suggesting that mAChR activation may provide pro-cognitive and antipsychotic efficacy. Accordingly, several mAChR agonists have been developed and entered clinical studies for the treatment of cognitive and psychiatric symptoms associated with Alzheimer's and neuropsychiatric diseases such as schizophrenia. (Carruthers, Neuroscience & Biobehavioral Rev., 2015, 55: 393-402; Jones, et al. Neuropsychopharmacology, 2012, 37: 16-42). One of these, the M1/M4 preferring mAChR agonist xanomeline was assessed in patients with Alzheimer's disease, and while showing a trend for improving cognitive deficits, did produce robust and dose-dependent reductions in hallucinations, delusions, vocal outbursts, and other behavioral disturbances in these patients. A subsequent study in patients with schizophrenia demonstrated that xanomeline produced robust improvements in positive, negative and cognitive symptoms. (Bodick, et al., Arch Neurol. 1997; 54: 465-73). Xanomeline, in addition to other mAChR agonists have been demonstrated to produce robust antipsychotic-like effects in a number of preclinical paradigms. For instance, xanomeline, reverses a number of dopamine driven behaviors, including amphetamine induced locomotion in rats, apomorphine induced climbing in mice, dopamine agonist driven turning in unilateral 6-OH-DA lesioned rats and amphetamine induced motor unrest in monkeys (without EPS liability). It also has been shown to inhibit A10, but not A9, dopamine cell firing and conditioned avoidance and induces c-fos expression in prefrontal cortex and nucleus accumbens, but not in striatum in rats. These data are all suggestive of an atypical antipsychotic-like profile. Subsequent studies with M4 knockout mice have demonstrated that the antipsychotic-like effects of xanomeline are mediated by the M4 receptor. Despite these promising clinical and preclinical effects, xanomeline, like other muscarinic agonists, ultimately failed in clinical development due to lack of adequate receptor subtype selectivity resulting in dose-limiting side effects including disturbed gastrointestinal motility, bradycardia, nausea and vomiting.

The development of selective M4 positive allosteric modulators (PAMs) is a strategy to overcome the challenges of developing selective orthosteric muscarinic agonists. Indeed, studies with M4 PAMs have shown that selective activation of M4 mAChRs can reverse both hyperdopaminergic and hypoglutamatergic behaviors in preclinical models. Accordingly, the compounds of the present invention, which are allosteric modulators of the M4 muscarinic acetylcholine receptor, are believed to be useful in the treatment of Alzheimer's disease and other diseases mediated by the muscarinic M4 muscarinic acetylcholine receptor.

SUMMARY OF THE INVENTION

The present invention is directed to cinnolinyl and quinolinyl pyrazol-4-yl-pyridine compounds which are allosteric modulators of the M4 muscarinic acetylcholine receptor. The present invention is also directed to uses of the compounds described herein in the potential treatment or prevention of neurological and psychiatric disorders and diseases in which M4 muscarinic acetylcholine receptors are involved. The present invention is also directed to compositions comprising these compounds. The present invention is also directed to uses of these compositions in the potential prevention or treatment of such diseases in which M4 muscarinic acetylcholine receptors are involved.

DETAILED DESCRIPTION OF THE INVENTION

The present invention is directed to compounds of the formula I:

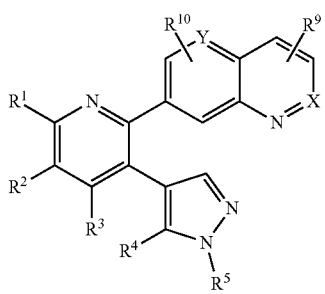

(I)

wherein:
X is —N= or —C(R$^8$)=;
Y is —N= or —C(R$^{11}$)=;
R$^1$ is selected from:
(1) hydrogen,
(2) halogen,
(3) —CN,
(4) —C$_{1-6}$alkyl, which is unsubstituted or substituted with a hydroxy, pyrazolyl, dihydropyranyl, or 1-3 fluoro,
(5) —O—C$_{1-6}$alkyl, which is unsubstituted or substituted with a hydroxy, —O—C$_{1-3}$alkyl, or 1-3 fluoro,
(6) cyclopropyl,
(7) —C=CH$_2$,
(8) —C≡CH,
(9) -pyrazolyl, which is unsubstituted or substituted with —C$_{1-6}$alkyl, and
(10) dihydropyranyl;
R$^2$ is selected from:
(1) hydrogen,
(2) halogen,
(3) —C$_{1-6}$alkyl,
(4) —CN,
(5) —OC$_{1-6}$alkyl, and
(6) —SC$_{1-6}$alkyl;
R$^3$ is selected from:
(1) hydrogen,
(2) chloro,
(3) —C$_{1-6}$alkyl, and
(4) —OC$_{1-6}$alkyl;
R$^4$ is selected from:
(1) hydrogen, and
(2) fluoro;
R$^5$ is —C$_{1-6}$alkyl, which is unsubstituted or substituted with:
(1) fluoro,
(2) hydroxy,
(3) —CN,
(4) keto,
(5) —C$_{1-6}$alkyl, which is unsubstituted or substituted with hydroxy, methoxy, fluoro, or —C$_{1-6}$alkyl-fluoro,
(6) —C$_{2-6}$alkenyl, which is unsubstituted or substituted with fluoro,
(7) —OC$_{1-6}$alkyl, which is unsubstituted or substituted with —C$_{1-6}$alkyl, hydroxy, methoxy, fluoro, or —C$_{1-6}$ alkyl-fluoro,
(8) —C$_{3-4}$cycloalkyl or C$_{6-10}$cycloalkyl, which is unsubstituted or substituted with —C$_{1-6}$alkyl, hydroxy, methoxy, fluoro, or —C$_{1-6}$alkyl-fluoro,
(9) tetrahydrofuranyl, which is unsubstituted or substituted with —C$_{1-6}$alkyl, hydroxy, methoxy, or 1-3 fluoro,
(10) tetrahydropyranyl, which is unsubstituted or substituted with —C$_{1-6}$alkyl, hydroxy, methoxy, or 1-3 fluoro, and
(11) phenyl, which is unsubstituted or substituted with —C$_{1-6}$alkyl, hydroxy, methoxy, or 1-3 fluoro;
each of R$^8$, R$^9$, R$^{10}$ and R$^{11}$ is independently selected from:
(1) hydrogen,
(2) halogen,
(3) —C$_{1-6}$alkyl, which is unsubstituted or substituted with: hydroxy, —OC$_{1-6}$alkyl, cyclopropyl, cyclobutyl, or 1-3 fluoro; phenyl, which is unsubstituted or substituted with hydroxy, —C$_{1-6}$alkyl or fluoro; or pyridyl, which is unsubstituted or substituted with hydroxy, —C$_{1-6}$alkyl or fluoro,
(4) —OC$_{1-6}$alkyl, which is unsubstituted or substituted with a hydroxy, —OC$_{1-6}$alkyl, cyclopropyl, cyclobutyl, or 1-3 fluoro,
(5) —C$_{3-6}$cycloalkyl, which is unsubstituted or substituted with a hydroxy, methoxy, or 1-3 fluoro, and
(6) —CN;
or a pharmaceutically acceptable salt thereof.

An embodiment of the present invention includes compounds of the formula Ia:

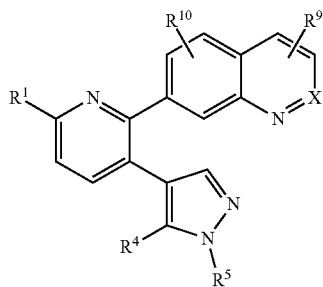

Ia wherein X, R$^1$, R$^4$, R$^5$, R$^9$ and R$^{10}$ are defined herein; or a pharmaceutically acceptable salt thereof.

An embodiment of the present invention includes compounds of the formula Ib:

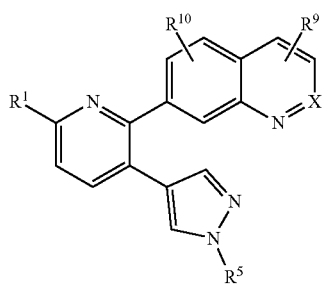

Ib wherein X, R$^1$, R$^5$, R$^9$ and R$^{10}$ are defined herein; or a pharmaceutically acceptable salt thereof.

An embodiment of the present invention includes compounds of the formula Ic:

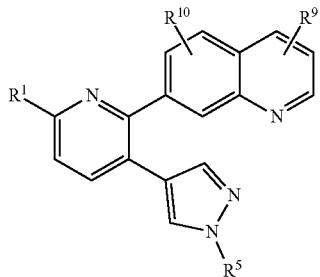

wherein $R^1$, $R^5$, $R^9$ and $R^{10}$ are defined herein; or a pharmaceutically acceptable salt thereof.

An embodiment of the present invention includes compounds of the formula Id:

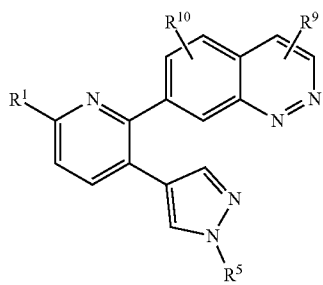

wherein $R^1$, $R^5$, $R^9$ and $R^{10}$ are defined herein; or a pharmaceutically acceptable salt thereof.

An embodiment of the present invention includes compounds wherein X is —N═.
An embodiment of the present invention includes compounds wherein X is $C(R^8)$═.
An embodiment of the present invention includes compounds wherein Y is —N═.
An embodiment of the present invention includes compounds wherein Y is $C(R^{11})$═.
An embodiment of the present invention includes compounds wherein $R^1$ is selected from:
(1) hydrogen,
(2) fluoro,
(3) chloro,
(4) —CN, and
(5) methyl.
An embodiment of the present invention includes compounds wherein $R^1$ is selected from:
(1) hydrogen,
(2) —CN, and
(3) methyl.
An embodiment of the present invention includes compounds wherein $R^1$ is hydrogen. An embodiment of the present invention includes compounds wherein $R^1$ is methyl.
An embodiment of the present invention includes compounds wherein $R^2$ is selected from:
(1) hydrogen, and
(2) methyl.
An embodiment of the present invention includes compounds wherein $R^2$ is hydrogen.

An embodiment of the present invention includes compounds wherein $R^3$ is selected from:
(1) hydrogen, and
(2) methyl.
An embodiment of the present invention includes compounds wherein $R^3$ is hydrogen.
An embodiment of the present invention includes compounds wherein $R^4$ is hydrogen. An embodiment of the present invention includes compounds wherein $R^4$ is fluoro.
An embodiment of the present invention includes compounds wherein $R^5$ is —$CH_2$—, which is substituted with a group selected from:
(1) adamantyl,
(2) bicyclopentyl,
(3) bicyclooctyl,
(4) cyclopropyl, which is unsubstituted or substituted with —$C_{1-6}$alkyl or 1-3 fluoro,
(5) cyclobutyl, which is unsubstituted or substituted with —$C_{1-6}$alkyl or 1-3 fluoro,
(6) cyclohexyl, which is unsubstituted or substituted with —$C_{1-6}$alkyl or 1-3 fluoro,
(7) phenyl, which is unsubstituted or substituted with 1-3 fluoro;
(8) spiropentyl, and
(9) tetrahydrofuranyl, which is unsubstituted or substituted with —$C_{1-6}$alkyl or 1-3 fluoro.
An embodiment of the present invention includes compounds wherein $R^5$ is —$C_{1-6}$alkyl, which is unsubstituted or substituted with fluoro, —$OC_{1-6}$alkyl, cyclopropyl, cyclobutyl, cyclohexyl, or phenyl.
An embodiment of the present invention includes compounds wherein $R^5$ is —$C_{1-6}$alkyl, which is unsubstituted or substituted with fluoro.
An embodiment of the present invention includes compounds wherein $R^5$ is selected from:
(1) 2,2-dimethylpropyl,
(2) 2,2-difluorobutyl,
(3) 3-methylbutyl,
(4) 3-fluoro-3-methylbutyl,
(5) neopentyl,
(6) 1-(methylcyclopentyl)methyl,
(7) 1-(fluorocyclopentyl)methyl,
(8) cyclopentyl-3,3,3-trifluoro-2,2-dimethylpropyl,
(9) 1-(cyclohexylmethyl), and
(10) (1-(trifluromethyl)cyclopropyl)methyl.
An embodiment of the present invention includes compounds wherein each of $R^8$, $R^9$, $R^{10}$ and $R^{11}$ is independently selected from:
(1) hydrogen,
(2) halogen,
(3) —$C_{1-6}$alkyl, which is unsubstituted or substituted with a hydroxy, or 1-3 fluoro,
(4) —$OC_{1-6}$alkyl, which is unsubstituted or substituted with a hydroxy, or 1-3 fluoro, and
(5) cyclopropyl.
An embodiment of the present invention includes compounds wherein each of $R^8$, $R^9$, $R^{10}$ and $R^{11}$ is independently selected from:
(1) hydrogen,
(2) fluoro,
(3) —$CH_3$,
(4) —$CF_3$, and
(5) —$OCH_3$, and
(6) cyclopropyl.

An embodiment of the present invention includes compounds wherein one of $R^8$, $R^9$, $R^{10}$ and $R^{11}$ is fluoro, —$CF_3$, or —$OCH_3$, and the other three of $R^8$, $R^9$, $R^{10}$ and $R^{11}$ are hydrogen.

An embodiment of the present invention includes compounds wherein each of $R^8$, $R^9$, $R^{10}$ and $R^{11}$ is hydrogen.

Certain embodiments of the present invention include a compound which is selected from the subject compounds of the Examples herein or a pharmaceutically acceptable salt thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Likewise, the present invention includes tautomeric forms of the compounds disclosed herein. Formula I shows the structure of the class of compounds without specific stereochemistry. At least some of the chemical names of compounds of the invention as set forth in this application may have been generated on an automated basis by use of commercially available chemical naming software programs, and have not been independently verified.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

As appreciated by those of skill in the art, halogen or halo as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl, and hexyl. Similarly, ($CH_2$-scycloalkyl-O—) indicates the presence of cyclopropoxy, cyclobutoxy, tetrahydrofuranyl, or tetrahydropyranyl ring. Substituents (such as $R^{1a}$, $R^{1b}$ and $R^{1c}$) may be absent if the valency of the group to which they are attached does not permit such substitution. A group which is designated as being independently substituted with substituents may be independently substituted with multiple numbers of such substituents.

The present invention also includes all pharmaceutically acceptable isotopic variations of a compound of the Formula I in which one or more atoms is replaced by atoms having the same atomic number, but an atomic mass or mass number different from the atomic mass or mass number usually found in nature. Such compounds are identical to those disclosed herein, but for the fact that one or more atoms are replaced by an atom having an atomic mass or mass number different from the atomic mass or mass number usually found in nature. Examples of isotopes suitable for inclusion in the compounds of the invention include isotopes of hydrogen such as $^2H$ and $^3H$, carbon such as $^{11}C$, $^{13}C$ and $^{14}C$, nitrogen such as $^{13}N$ and $^{15}N$, oxygen such as $^{15}O$, $^{17}O$ and $^{18}O$, phosphorus such as $^{32}P$, sulfur such as $^{35}S$, fluorine such as $^{18}F$, iodine such as $^{123}I$ and $^{125}I$, and chlorine such as $^{36}Cl$. Certain isotopically-labelled compounds of Formula I, for example those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. An embodiment of the present invention includes compounds that are substituted with a positron emitting isotope. An embodiment of the present invention includes compounds that are substituted with a $^{11}C$ isotope. An embodiment of the present invention includes compounds that are substituted with an $^{18}F$ isotope. In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Those skilled in the art will recognize those instances in which the compounds of the invention may form salts. In such instances, another embodiment provides pharmaceutically acceptable salts of the compounds of the invention. Thus, reference to a compound of the invention herein is understood to include reference to salts thereof, unless otherwise indicated. The term "pharmaceutically acceptable salts" refers to salts prepared from pharmaceutically acceptable non-toxic bases or acids including inorganic or organic bases and inorganic or organic acids. In addition, when a compound of the invention contains both a basic moiety, such as, but not limited to a pyridine or imidazole, and an acidic moiety, such as, but not limited to a carboxylic acid, zwitterions ("inner salts") may be formed and are included within the present invention. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates or solvates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids. It will be understood that, as used herein, references to the compounds of Formula I are meant to also include the pharmaceutically acceptable salts. Salts of the compounds of the invention may be formed by methods known to those of ordinary skill in the art, for example, by reacting a compound of the invention with an amount of acid or base, such as an equivalent amount, in a medium such as one in which the salt precipitates or in an aqueous medium followed by lyophilization.

Exemplifying the invention is the use of the compounds disclosed in the Examples and herein. Specific compounds within the present invention include a compound which is selected from the compounds disclosed in the following Examples and pharmaceutically acceptable salts thereof and individual enantiomers or diastereomers thereof.

As used herein, the term "M4 muscarinic acetylcholine receptor" refers to one of the five subtypes of the muscarinic acetylcholine receptor, which is from the superfamily of G-protein coupled receptors. The family of muscarinic receptors is described, for example, in *Pharmacol Ther,* 1993, 58:319-379; *Eur J Pharmacol,* 1996, 295:93-102, and *Mol Pharmacol,* 2002, 61:1297-1302. The muscarinic receptors are known to contain one or more allosteric sites, which may alter the affinity with which muscarinic ligands bind to the primary binding or orthosteric sites. See, e.g., S. Lazareno, et al., *Mol Pharmacol,* 2002, 62:6, 1491-1505.

As used herein, the terms "positive allosteric modulator" and "allosteric potentiator" are used interchangeably, and refer to a ligand which interacts with an allosteric site of a receptor to augment the response produced by the endogenous ligand at the orthosteric binding site. The compounds of the invention are allosteric modulators of the M4 muscarinic acetylcholine receptor, including as positive allosteric modulators of the M4 muscarinic acetylcholine receptor and silent allosteric modulators of the M4 muscarinic acetylcholine receptor. Some of the compounds of the invention are agonists of the M4 muscarinic acetylcholine receptor. Some of the compounds of the invention are allosteric modulators of the M1 muscarinic acetylcholine receptor, or may be agonists of the M1 muscarinic acetylcholine receptor. For example, a modulator or potentiator may directly or indirectly augment the response produced by the endogenous ligand (such as acetylcholine or xanomeline) at the orthosteric site of the M4 muscarinic acetylcholine receptor in an animal, in particular, a human.

The actions of ligands at allosteric receptor sites may also be understood according to the "allosteric ternary complex model," as known by those skilled in the art. The allosteric ternary complex model is described with respect to the family of muscarinic receptors in Birdsall et al, *Life Sciences,* 2001, 68:2517-2524. For a general description of the role of allosteric binding sites, see Christopoulos, *Nature Reviews: Drug Discovery,* 2002, 1:198-210.

It is believed that the compounds of the invention bind to an allosteric binding site that is distinct from the orthosteric acetylcholine site of the M4 muscarinic acetylcholine receptor, thereby augmenting the response produced by the endogenous ligand acetylcholine at the orthosteric site of the M4 muscarinic acetylcholine receptor. It is also believed that the compounds of the invention bind to an allosteric site which is distinct from the xanomeline site of the M4 muscarinic acetylcholine receptor, thereby augmenting the response produced by the endogenous ligand xanomeline at the orthosteric site of the M4 muscarinic acetylcholine receptor.

The present invention is also directed to the use of the compounds disclosed herein as modulators of M4 muscarinic acetylcholine receptor activity. The subject compounds and pharmaceutically acceptable salts thereof are useful in a method of M4 modulating muscarinic acetylcholine receptor activity in a subject such as a mammal comprising the administration of an amount of the compound. In addition to primates, especially humans, a variety of other mammals may be administered with a compound of the present invention. The present invention is directed to a compound of the present invention or a pharmaceutically acceptable salt thereof that could be useful in therapy. The present invention may further be directed to a use of a compound of the present invention or a pharmaceutically acceptable salt thereof for the manufacture of a medicament for modulating M4 muscarinic acetylcholine receptor activity or treating the disorders and diseases noted herein in humans and animals.

A subject administered with a compound of the present invention, or a pharmaceutically acceptable salt thereof, is generally a mammal, such as a human being, male or female. The amount of compound administered to the subject is an amount sufficient to modulate the M4 muscarinic acetylcholine receptor in the subject. In an embodiment, the amount of compound can be an "effective amount" or "therapeutically effective amount", wherein the subject compound or pharmaceutical composition is administered in an amount that will elicit the biological or medical response of a tissue, system, animal or human that is being sought by the researcher, veterinarian, medical doctor or other clinician, or otherwise inhibiting the noted disease and thus producing the desired therapeutic, ameliorative, inhibitory or preventative effect. An effective amount does not necessarily include considerations of toxicity and safety related to the administration of the compound. It is recognized that one skilled in the art may affect neurological and psychiatric disorders associated with M4 muscarinic acetylcholine receptor modulation by treating a subject presently afflicted with the disorders, or by prophylactically treating a subject likely to be afflicted with the disorders, with an effective amount of a compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a subject that is predisposed to such disease or disorder. The terms "administration of" and "administering" a compound should be understood to mean providing a compound of the invention or a prodrug of a compound of the invention to the subject. The term "dysfunction" refers to abnormality or impairment in the function of the noted system.

The term "composition" as used herein is intended to encompass a product comprising the specified ingredients in the specified amounts, as well as any product which results, directly or indirectly, from combination of the specified ingredients in the specified amounts. Such term is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The utility of the compounds in accordance with the present invention as modulators of M4 muscarinic acetylcholine receptors may be readily determined without undue experimentation by methodology well known in the art, including monitoring the mobilization of intracellular Ca++, determining the levels of intracellular cAMP, or quantiting the exchange of GDP for [35S]γGTP.

In a typical experiment the M4 muscarinic acetylcholine receptor modulating activity of the compounds of the present invention was determined in accordance with the following experimental method. CHO-K1 cells stably transfected with human M4 receptor and chimeric G-protein Gαqi5 (Coward P, et al., Analytical Biochemistry, 270:242-248 (1999)) are thawed from liquid $N_2$ storage, resuspended in growth medium, plated in black, clear bottom 384 well plates, and incubated 16-20 hours at 37° C., 5% $CO_2$. On the day of assay, growth medium is removed, the cells are washed 2 times with wash buffer, and cells are incubated in dye loading buffer at 37° C., 5% $CO_2$ for ~1 hour. Following dye loading the cell plates are placed in a FLIPR Tetra instrument and while monitoring dye fluorescence (excitation 470-495 nM/emission 515-575 nM), 10 uL of test substance at increasing concentrations is added, and fluorescence values are recorded for 4 min. Next, 10 uL of acetylcholine is added (final concentration calculated so as to achieve 20% of the maximum acetycholine response), and the fluorescence reading is continued for 3.5 min. In some cases, a third addition of acetylcholine (final concentration calculated to achieve 70% of the maximal acetylcholine response) is performed. The resulting dose response curves are fit to a 4 parameter logistic equation and the final result is determined as the inflection point (IP) of the curve The intrinsic M4 muscarinic acetylcholine receptor modulating activity of a compound which may be used in the present invention may be determined by these assays.

All of the final compounds of the following examples had activity in the human FLIPR-based M4 PAM assay with an IP of about 5 nM to 1000 nM against the human M4 muscarinic acetylcholine receptor. Additional data is provided in the following Examples. Such a result is indicative of the intrinsic activity of the compounds in use as a modulating the human M4 muscarinic acetylcholine receptor. In general, one of ordinary skill in the art would appreciate that a substance is considered to effectively modulate the human M4 muscarinic acetylcholine receptor if it has an IP of less than about 50 μM, or more specifically less than about 15000 nM.

The M4 muscarinic acetylcholine receptor has been implicated in a wide range of biological functions. This has suggested a potential role for these receptors in a variety of disease processes in humans or other species. The compounds of the present invention could therefore potentially have utility in treating, preventing, ameliorating, controlling or reducing the risk of a variety of neurological and psychiatric disorders associated with M4 muscarinic acetylcholine receptors, including one or more of the following conditions or diseases, and other diseases related to general M4 muscarinic acetylcholine receptor system dysfunction.

Potential conditions or disorders for which the compounds of the invention may be useful further include one or more of the following conditions or diseases: Alzheimer's disease (including mild Alzheimer's disease, moderate Alzheimer's disease and severe Alzheimer's disease), olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, cognitive disorders (including mild cognitive impairment), glaucoma, amyloidosis, type II diabetes, diabetes-associated amyloidogenesis, scrapie, bovine spongiform encephalitis, traumatic brain injury, Creutzfeld-Jakob disease, schizophrenia, sleep disorders, pain disorders (including acute pain, inflammatory pain and neuropathic pain), pulmonary hypertension, chronic obstructive pulmonary disease (COPD), asthma, urinary incontinence, glaucoma, schizophrenia, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, autism, atherosclerosis, tolerance and/or dependence to opioid treatment of pain, and for treatment of withdrawal syndrome of e.g., alcohol, opioids, and cocaine, Huntington's disease, drug-induced dyskinesias.

Potential conditions or disorders for which the compounds of the invention may be useful further include one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Levodopa induced dyskinesia, other drug induced dyskinesia (e.g. tardive dyskinesias), Huntington's disease, Pick's disease, Creutzfeldt-Jacob disease, perinatal hypoxia, other general medical conditions or substance abuse); delirium, amnestic disorders or age related cognitive decline; delusional disorder, shared psychotic disorder, catastrophic schizophrenia, postpartum psychosis, psychotic depression, psychotic break, tardive psychosis, myxedematous psychosis, occupational psychosis, menstrual psychosis, secondary psychotic disorder, bipolar I disorder with psychotic features, and substance-induced psychotic disorder; major depressive disorder, affective disorder, bipolar disorder, electrolyte disorder, neurological disorder, hypoglycemia, AIDS, lupus, and post-traumatic stress disorder; brain tumor, dementia with Lewy bodies, multiple sclerosis, sarcoidosis, Lyme disease, syphilis, Alzheimer's disease, Parkinson's disease, and anti-NMDA receptor encephalitis. Thus, in another specific embodiment, the present invention provides a method for treating schizophrenia or psychosis comprising administering to a patient in need thereof an effective amount of a compound of the present invention. At present, the text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

Potential conditions or disorders for which the compounds of the invention may be useful further include one or more of the following conditions or diseases: mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; affective neurosis; depressive neurosis; anxiety neurosis; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; idiopathic and drug-induced Parkinson's disease; muscular spasms and disorders associated with muscular spasticity including tremors, epilepsy, convulsions, seizure disorders, absence seizures, complex partial and generalized seizures; Lennox-Gastaut syndrome; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; dissociative disorders including multiple personality syndromes and psychogenic amnesias; substance-related disorders, substance use, substance abuse, substance seeking, substance reinstatement, all types of psychological and physical addictions and addictive behaviors, reward-related behaviors (including substance-induced delirium, persisting dementia, persisting amnestic disorder, psychotic disorder or anxiety disorder; tolerance, addictive feeding, addictive feeding behaviors, binge/purge feeding behaviors, dependence, withdrawal or relapse from substances including alcohol, amphetamines, cannabis, cocaine, hallucinogens, inhalants, morphine, nicotine, opioids, phencyclidine, sedatives, hypnotics or anxiolytics); appetite, taste, eating or drinking disorders; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); neurodegenerative disorders including nosological entities such as disinhibition-dementia-parkinsonism-amyotrophy complex; pallido-ponto-nigral degeneration; epilepsy; seizure disorders; attention deficit/hyperactivity disorder (ADHD); conduct disorder; migraine (including migraine headache); headache; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; gastric dyskinesia; gastric ulcers; Kallman's syndrome (anosmia); asthma; cancer; conditions associated with visceral pain such as irritable bowel syndrome, and angina; eating disorders; urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache.

Potential sleep conditions or disorders for which the compounds of the invention may be useful include enhancing sleep quality; improving sleep quality; augmenting sleep maintenance; increasing the value which is calculated from the time that a subject sleeps divided by the time that a subject is attempting to sleep; decreasing sleep latency or onset (the time it takes to fall asleep); decreasing difficulties in falling asleep; increasing sleep continuity; decreasing the number of awakenings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing daytime alertness; reducing daytime drowsiness; treating or reducing excessive daytime sleepiness; insomnia; hypersomnia; narcolepsy; interrupted sleep; sleep apnea; wakefulness; nocturnal myoclonus; REM sleep interruptions; jet-lag; shift workers' sleep disturbances; dyssomnias; night terror; insomnias associated with depression, emotional/mood disorders, as well as sleep walking and enuresis, and sleep disorders which accompany aging; Alzheimer's sundowning; conditions associated with circadian rhythmicity as well as mental and physical disorders associated with travel across time zones and with rotating shift-work schedules; conditions due to drugs which cause reductions in REM sleep as a side effect; syndromes which are manifested by non-restorative sleep and muscle pain or sleep apnea which is associated with respiratory disturbances during sleep; and conditions which result from a diminished quality of sleep.

Pain disorders for which the compounds of the invention may be useful include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (eg, postmastectomy syndrome, postthoracotomy syndrome, stump pain); bone and joint pain (osteoarthritis), repetitive motion pain, dental pain, cancer pain, myofascial pain (muscular injury, fibromyalgia); perioperative pain (general surgery, gynecological), chronic pain, dysmennorhea, as well as pain associated with angina, and inflammatory pain of varied origins (e.g. osteoarthritis, rheumatoid arthritis, rheumatic disease, teno-synovitis and gout), headache, migraine and cluster headache, headache, primary hyperalgesia, secondary hyperalgesia, primary allodynia, secondary allodynia, or other pain caused by central sensitization.

The subject compounds could further be of potential use in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to subjects (animals and human) in need of such treatment in dosages that will provide optimal pharmaceutical efficacy. The selected dosage depends upon the desired therapeutic effect, on the route of administration, and on the duration of the treatment. The dose will vary from subject to subject depending upon the nature and severity of disease, the subject's weight, special diets then being followed by a subject, concurrent medication, and other factors which those skilled in the art will recognize. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Generally, dosage levels of between 0.0001 to 10 mg/kg of body weight daily are administered to the subject, e.g., humans and elderly humans, to obtain effective modulation of M4 muscarinic acetylcholine receptors. The dosage range will generally be about 0.5 mg to 1.0 g per subject per day which may be administered in single or multiple doses. In one embodiment, the dosage range will be about 0.5 mg to 500 mg per subject per day; in another embodiment about 0.5 mg to 200 mg per subject per day; and in yet another embodiment about 5 mg to 50 mg per subject per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 30 mg, 50 mg, 80 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the subject to be treated. The compounds may be administered on a regimen of 1 to 4 times per day, such as once or twice per day. The compounds may be administered before bedtime. For example, the compounds may be administered about 1 hour prior to bedtime, about 30 minutes prior to bedtime or immediately before bedtime.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is contemplated. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is contemplated. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be used in combination with one or more other drugs in the treatment of diseases or conditions for which the compounds of the present invention have utility, where the combination of the drugs together are safer or more effective than either drug alone. In a embodiment, the subject compound may be employed in combination with other compounds which are known in the art, either administered separately or in the same pharmaceutical compositions, including, but are not limited to: anti-Alzheimer's agents; beta-secretase inhibitors, such as verubecestat; alpha 7 nicotinic agonists, such as ABT089, SSR180711 and MEM63908; HT2a modulators, such as pimavaserin; ADAM 10 ligands or activators; gamma-secretase inhibitors, such as LY450139 and TAK 070; gamma-secretase inhibitors; gamma secretase modulators; tau phosphorylation inhibitors; glycine transport inhibitors; LXR β agonists; ApoE4 conformational modulators; NR2B antagonists; androgen receptor modulators; blockers of Δβ oligomer formation; 5-HT4 agonists, such as PRX-03140; 5-HT6 antagonists, such as GSK 742467, SGS-518, FK-962, SL-65.0155, SRA-333 and xaliproden; 5-HT1a antagonists, such as lecozotan; p25/CDK5 inhibitors; NK1/NK3 receptor antagonists; COX-2 inhibitors; HMG-CoA reductase inhibitors; NSAID's including ibuprofen; vitamin E; anti-amyloid antibodies (including anti-amyloid humanized monoclonal antibodies), such as bapineuzumab, ACC001, CAD106, AZD3102, H12A11V1; anti-inflammatory compounds such as (R)-flurbiprofen, nitroflurbiprofen, ND-1251, VP-025, HT-0712 and EHT-202; PPAR gamma agonists, such as pioglitazone and rosiglitazone; CB-1 receptor antagonists or CB-1 receptor inverse agonists, such as AVE1625; antibiotics such as doxycycline and rifampin; CB-1 receptor antagonists or CB-1 receptor inverse agonists; antibiotics such as doxycycline and rifampin; N-methyl-D-aspartate (NMDA) receptor antagonists, such as memantine, neramexane and EVT101; recombinant growth hormone; growth hormone secretagogues such as ibutamoren, ibutamoren mesylate, and capromorelin; histamine H3 receptor antagonists such as ABT-834, ABT 829, GSK 189254 and CEP16795; AMPA agonists or AMPA modulators, such as CX-717, LY 451395, LY404187 and S-18986; neuronal nicotinic agonists; muscarinic antagonists (e.g., M1 agonists (such as acetylcholine, oxotremorine, carbachol, or McNa343), or $M_2$ antagonists (such as atropine, dicycloverine, tolterodine, oxybutynin, ipratropium, methoctramine, tripitamine, or gallamine)); cholinesterase inhibitors (e.g., acetyl- and/or butyrylchlolinesterase inhibitors such as donepezil (Aricept®), (±)-2,3-dihydro-5,6-dimethoxy-2-[[1-(phenylmethyl)-4-piperidinyl]methyl]-1H-inden-1-one hydrochloride), tacrine, phenserine, ladostigil, ABT-089, galantamine (Razadyne®), and rivastigimine (Exelon®); N-methyl-D-aspartate receptor antagonists (e.g., Namenda® (memantine HCl, available from Forest Pharmaceuticals, Inc.); combinations of cholinesterase inhibitors and N-methyl-D-aspartate receptor antagonists; anti-inflammatory agents that can reduce neuroinflammation; glycogen synthase kinase beta inhibitors; promoters of alpha secretase activity; PDE IV inhibitors, including MEM1414, HT0712 and AVE8112; PDE-10 inhibitors; Tau kinase inhibitors (e.g., GSK3beta inhibitors, cdk5 inhibitors, or ERK inhibitors); GSK30 inhibitors, including AZD1080, SAR502250 and CEP16805; neuronal nicotinic agonists; selective M1 agonists; HDAC inhibitors; and microtubule affinity regulating kinase (MARK) ligands; Tau aggregation inhibitors (e.g., Rember®); RAGE inhibitors (e.g., TTP 488 (PF-4494700)); anti-Abeta vaccine; APP ligands; agents that upregulate insulin, cholesterol lowering agents such as HMG-CoA reductase inhibitors (for example, statins such as Atorvastatin, Fluvastatin, Lovastatin, Mevastatin, Pitavastatin, Pravastatin, Rosuvastatin, Simvastatin) and/or cholesterol absorption inhibitors (such as Ezetimibe), or combinations of HMG-CoA reductase inhibitors and cholesterol absorption inhibitors (such as, for example, Vytorin®); fibrates (such as, for example, clofibrate, Clofibride, Etofibrate, and Aluminium Clofibrate); combinations of fibrates and cholesterol lowering agents and/or cholesterol absorption inhibitors; nicotinic receptor agonists; niacin; combinations of niacin and cholesterol absorption inhibitors and/or cholesterol lowering agents (e.g., Simcor® (niacin/simvastatin, available from Abbott Laboratories, Inc.); LXR agonists; LRP mimics; H3 receptor antagonists; histone deacetylase inhibitors; hsp90 inhibitors; 5-HT4 agonists (e.g., PRX-03140 (Epix Pharmaceuticals)); 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux such as gelsolin; Metal-protein attenuating compound (e.g., PBT2); and GPR3 modulators; and antihistamines such as Dimebolin (e.g., Dimebon®, Pfizer); or other drugs that affect receptors or enzymes that either increase the efficacy, safety, convenience, or reduce unwanted side effects or toxicity of the compounds of the present invention.

Examples of combinations of the compounds include combinations with agents for the treatment of schizophrenia, for example in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, aiprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproelone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisuipride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, frihexyphenidyl, thioridazine, thiothixene, trifluoperazine or ziprasidone.

Examples of combinations of the compounds include combinations with agents for the treatment of pain, for example non-steroidal anti-inflammatory agents, such as aspirin, diclofenac, duflunisal, fenoprofen, flurbiprofen, ibuprofen, indomethacin, ketoprofen, ketorolac, naproxen, oxaprozin, piroxicam, sulindac and tolmetin; COX-2 inhibitors, such as celecoxib, rofecoxib, valdecoxib, 406381 and 644784; CB-2 agonists, such as 842166 and SAB378; VR-1 antagonists, such as AMG517, 705498, 782443, PAC20030, V114380 and A425619; bradykinin B1 receptor antagonists, such as SSR240612 and NVPSAA164; sodium channel blockers and antagonists, such as VX409 and SPI860; nitric oxide synthase (NOS) inhibitors (including iNOS and nNOS inhibitors), such as SD6010 and 274150; glycine site antagonists, including lacosamide; neuronal nicotinic agonists, such as ABT 894; NMDA antagonists, such as AZD4282; potassium channel openers; AMPA/kainate receptor antagonists; calcium channel blockers, such as ziconotide and NMED160; GABA-A receptor IO modulators (e.g., a GABA-A receptor agonist); matrix metalloprotease (MMP) inhibitors; thrombolytic agents; opioid analgesics such as codeine, fentanyl, hydromorphone, levorphanol, meperidine, methadone, morphine, oxycodone, oxymorphone, pentazocine, propoxyphene; neutrophil inhibitory factor (NIF); pramipexole, ropinirole; anticholinergics; amantadine; monoamine oxidase B15 ("MAO-B") inhibitors; 5HT receptor agonists or antagonists; mGlu5 antagonists, such as AZD9272; alpha agonists, such as AGNXX/YY; neuronal nicotinic agonists, such as ABT894; NMDA receptor agonists or antagonists, such as AZD4282; NKI antagonists; selective serotonin reuptake inhibitors ("SSRI") and/or selective serotonin and norepinephrine reuptake inhibitors ("SSNRI"), such as duloxetine; tricyclic antidepressant drugs, norepinephrine modulators; lithium; valproate; gabapentin; pregabalin; rizatriptan; zolmitriptan; naratriptan and sumatriptan.

The compounds of the present invention may be administered in combination with compounds useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, orexin antagonists, alpha-1 antagonists, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, filorexant, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, suvorexant, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. The subject or patient to whom the compounds of the present invention is administered is generally a human being, male or female, but may also encompass other mammals, such as dogs, cats, mice, rats, cattle, horses, sheep, rabbits, monkeys, chimpanzees or other apes or primates, for which treatment of the above noted disorders is desired.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. Pharmaceutical compositions of the present compounds in the form of a sterile injectable aqueous or oleagenous suspension may be formulated by known techniques for depo administration and thereby provide a sustained action over a longer period. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art or as illustrated herein. The following abbreviations are used herein: Me: methyl; Et: ethyl; t-Bu: tert-butyl; Ar: aryl; Ph: phenyl; BINAP: 2,2'-bis(diphenylphosphino)-1,1'-binaphthyl; Bn: benzyl; Ac: acetyl; Boc: tert-butyloxy carbonyl; BSA: bovine serum albumin; CbzCl: benzylchloroformate; CDI: carbonyl diimidazole; DAST: diethylaminosulfur trifluoride;

DCM: dichloromethane; DCE: dichloroethane; DEA: diethylamine; DEAD: diethylazodicarboxylate; DIAD: diisopropyl azodicarboxylate; DIBAL: diisobutylaluminium hydride; DIPEA: N,N-diisopropylethylamine; DMAP: 4-dimethylaminopyridine; DMF: N,N-dimethylformamide; DMSO: dimethylsulfoxide; dppf: 1,1'-bis(diphenylphosphino)ferrocene; $CH_2Cl_2$: dichloromethane; EDC: N-(3-Dimethylaminopropyl)-N'-ethylcarbodiimide; $Et_3N$: triethylamine; EtOAc: ethyl acetate; EtOH: ethanol; HATU: (1-[bis(dimethylamino)methylene]-1H-1,2,3-triazolo[4,5-b]pyridinium 3-oxid hexafluorophosphate); HCl: hydrogen chloride; HOAt: 1-hydroxy-7-aza-benzotriazole; HOBT: hydroxybenzotriazole hydrate; HPLC: high performance liquid chromatography; Hunig's base: N,N-diisopropylethylamine; LDA: diisopropylamine; mCPBA: meta-chloroperbenzoic acid; MeOH: methanol; $MgSO_4$: magnesium sulfate; Ms: methanesulfonyl; MTBE: methyl tert-butyl ether; $NaHCO_3$: sodium bicarbonate; NaOH: sodium hydroxide; NCS: N-chlorosuccinimide; NMM: N-methylmorpholine; $PtO_2$: platinum oxide; PyClu: 1-(chloro-1-pyrrolidinylmethylene)-pyrrolidinium hexafluorophosphate; rt: room temperature; $SOCl_2$: thionyl chloride; T3P: 2,4,6-tripropyl-1,3,5,2,4,6-trioxatriphosphorinane-2,4,6-trioxide; TBAF: tetra-n-butylammonium fluoride; TFA: trifluoroacetic acid; TFAA: trifluoroacetic anhydride; THF: tetrahydrofuran; TIPS: triisopropylsilyl; TLC: thin layer chromatography; Ts: toluenesulfonyl; X-Phos: 2-(dicyclohexyl-phosphino)-2',4',6'-triisopropylbiphenyl.

The compounds of the present invention can be prepared in a variety of fashions. The preparation of the various starting materials used herein is within the skill of a person versed in the art. In some cases the final product may be further modified, for example, by manipulation of substituents. These manipulations may include, but are not limited to, reduction, oxidation, alkylation, acylation, and hydrolysis reactions which are commonly known to those skilled in the art. The following examples are provided so that the invention might be more fully understood. These examples are illustrative only and should not be construed as limiting the invention in any way. Because the schemes are an illustration, the invention should not be construed as being limited by the chemical reactions and conditions expressed. In some cases the order of carrying out the foregoing reaction schemes may be varied to facilitate the reaction or to avoid unwanted reaction products. Absolute stereochemistry of separated stereoisomers in the examples and intermediates was not determined unless stated otherwise in an example.

SCHEME 1

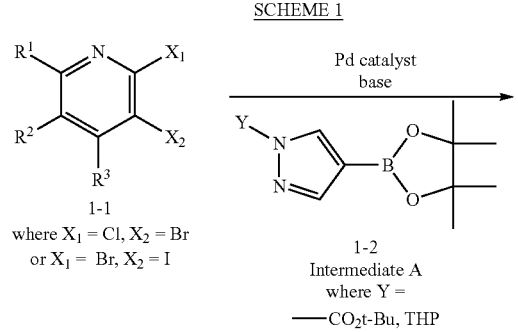

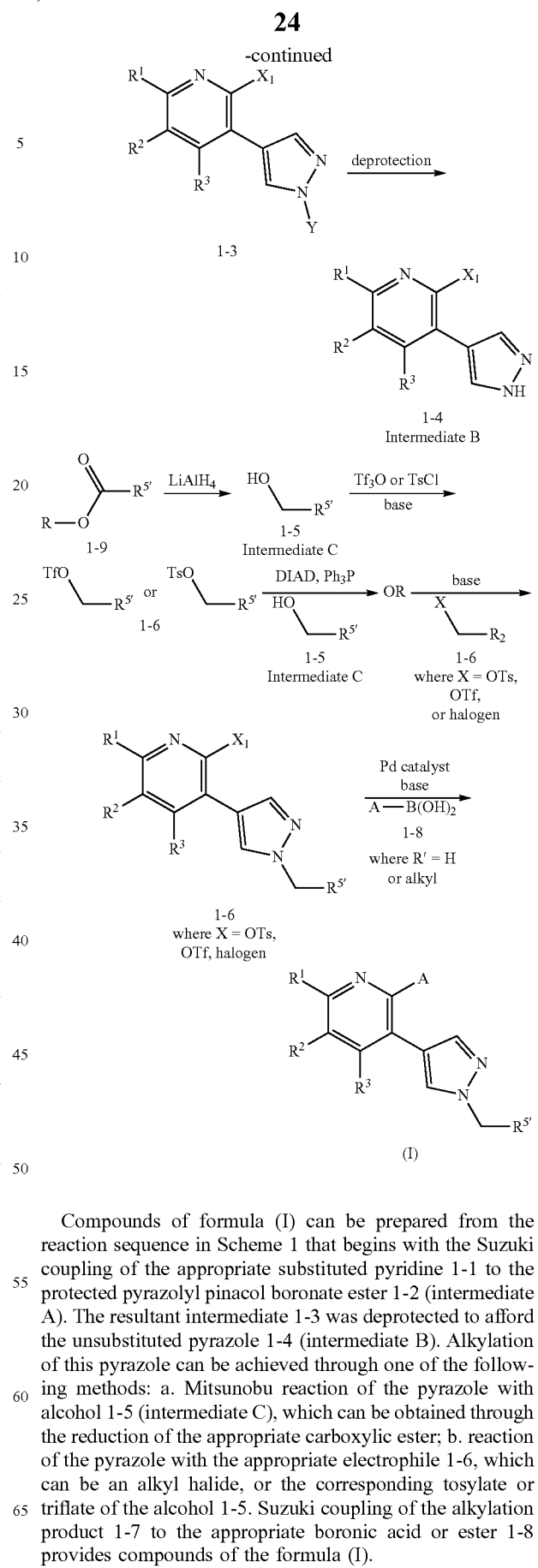

Compounds of formula (I) can be prepared from the reaction sequence in Scheme 1 that begins with the Suzuki coupling of the appropriate substituted pyridine 1-1 to the protected pyrazolyl pinacol boronate ester 1-2 (intermediate A). The resultant intermediate 1-3 was deprotected to afford the unsubstituted pyrazole 1-4 (intermediate B). Alkylation of this pyrazole can be achieved through one of the following methods: a. Mitsunobu reaction of the pyrazole with alcohol 1-5 (intermediate C), which can be obtained through the reduction of the appropriate carboxylic ester; b. reaction of the pyrazole with the appropriate electrophile 1-6, which can be an alkyl halide, or the corresponding tosylate or triflate of the alcohol 1-5. Suzuki coupling of the alkylation product 1-7 to the appropriate boronic acid or ester 1-8 provides compounds of the formula (I).

SCHEME 2

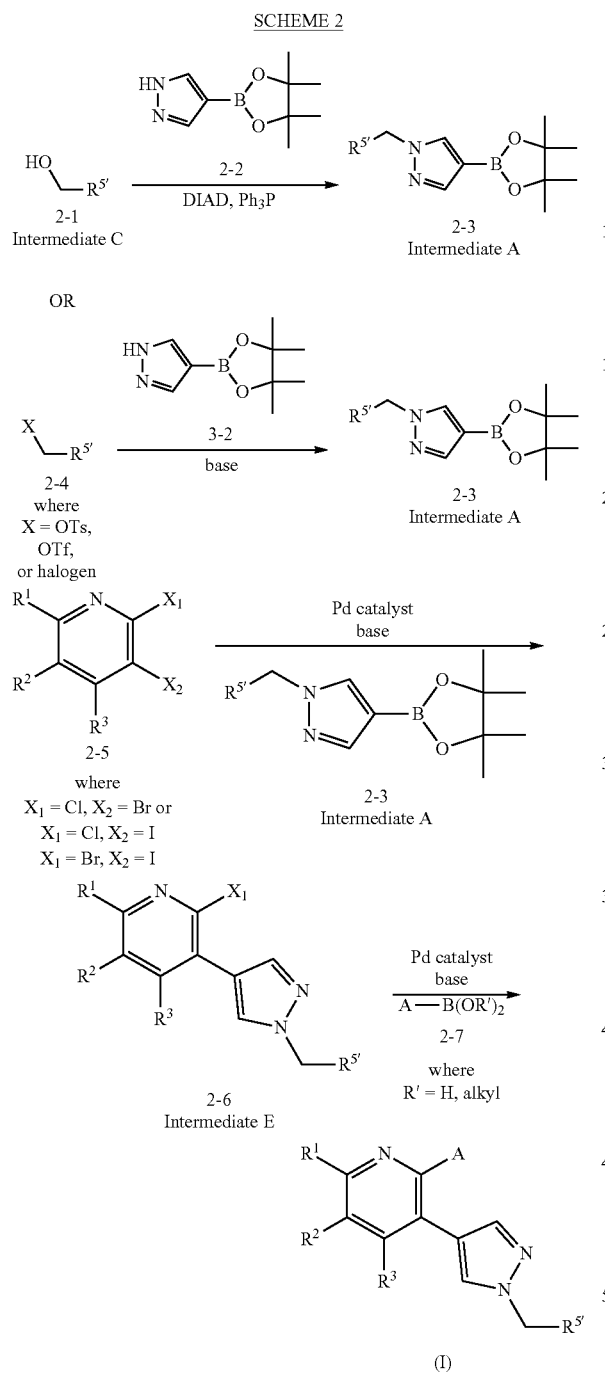

SCHEME 3

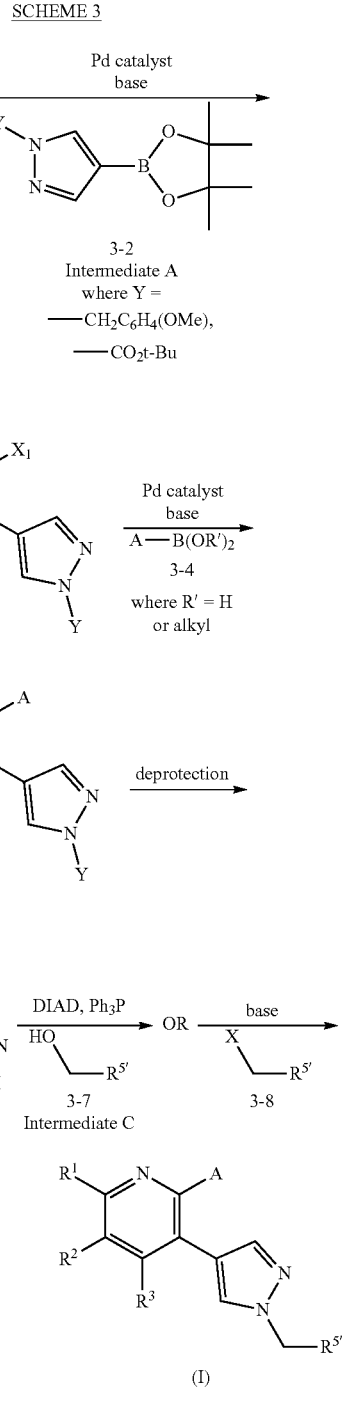

Compounds of formula (I) can be prepared from the reaction sequence in Scheme 2 that begins with the pinacol boronate ester 2-3 (intermediate A). This boronate ester can be prepared either through Mitsunobu reaction of the alcohol 2-1 with 4-(4,4,5,5-tetramethyl-1,3,2-dioxaborolan-2-yl)-1H-pyrazole 2-2, or through alkylation of 2-2 with the electrophile 2-4. Suzuki coupling of the appropriate substituted pyridine 2-5 with the pinacol boronate ester 2-3, followed by another Suzuki coupling of the resultant product 2-6 (Intermediate E) with another known or prepared boronic acid or ester 2-7 provides compounds of the formula (I).

Compounds of formula (I) can be prepared from the reaction sequence in Scheme 3 that begins with the Suzuki coupling of the appropriate substituted pyridine 3-1 with the pinacol boronate ester 3-2 (intermediate A), followed by another Suzuki coupling of the resultant product 3-3 with a known or prepared boronic acid or ester 3-4 to afford the pyrazole 3-5. Deprotection of the pyrazole, followed by either a Mitsunobu reaction with alcohol 3-7 (intermediate C) in the presence of diisopropyl azodicarboxylate (or its equivalent) and triphenylphosphine (or its equivalent), or an alkylation with 3-8, provides compounds of the formula (I).

SCHEME 4

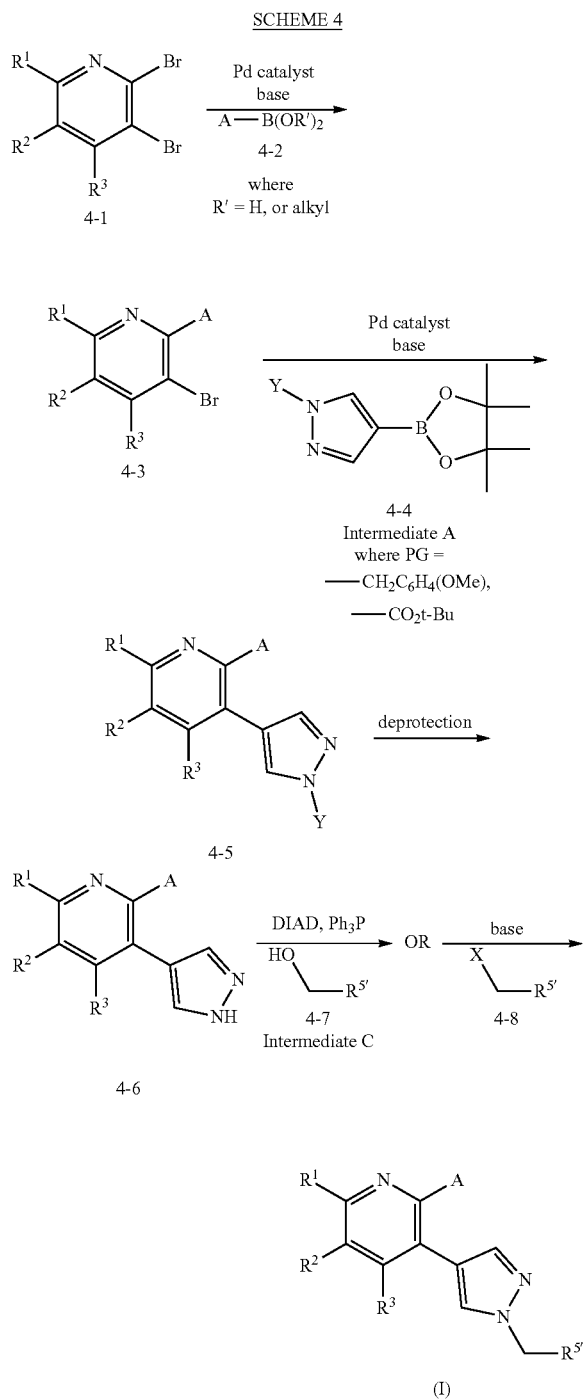

4-1 → 4-2 (A—B(OR')₂, where R' = H, or alkyl), Pd catalyst, base 4-3 → 4-4 Intermediate A where PG = —CH₂C₆H₄(OMe), —CO₂t-Bu 4-5 → deprotection → 4-6

4-6 → (DIAD, Ph₃P, HO—R⁵′ 4-7 Intermediate C) OR (base, X—R⁵′ 4-8) → (I)

Compounds of formula (I) can be prepared from the reaction sequence in Scheme 4 that begins with the Suzuki coupling of the 2,3-dibromo pyridine 4-1 with a known or prepared boronic ester or acid 4-2 to afford the intermediate 4-3. Suzuki coupling of this intermediate with the pinacol boronate ester 4-4 (intermediate A), provides the pyrazole 4-5. Deprotection of the pyrazole, followed by either a Mitsunobu reaction with alcohol 4-7 (intermediate C) in the presence of diisopropyl azodicarboxylate (or its equivalent) and triphenylphosphine (or its equivalent), or an alkylation with 4-8, provides compounds of the formula (I).

Intermediate A1

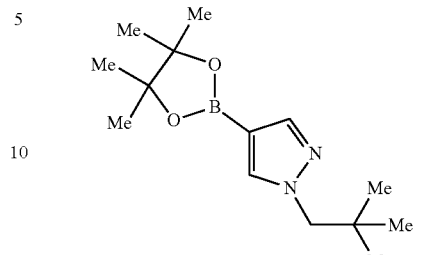

1-neopentyl-4-(4,4,5,5-tetramethyl-1,3,2-dioxaborolan-2-yl)-1H-pyrazole

To a N,N-dimethylformamide (8 mL) solution of 4-(4,4,5,5-tetramethyl-1,3,2-dioxaborolan-2-yl)-1H-pyrazole (3.67 g, 18.9 mmol) was added 1-iodo-2,2-dimethylpropane (2.50 g, 12.6 mmol) and cesium carbonate (10.28 g, 31.6 mmol). The reaction mixture was stirred at 90° C. for 16 hours and quenched with water (5 mL). The aqueous layer was extracted with ethyl acetate (20 mL×2). The combined organic layers were washed with brine (20 mL×2), dried (sodium sulfate), filtered and concentrated in vacuum to afford the crude product. Purification by column chromatography over silica gel, eluting with petroleum ether/tetrahydrofuran, afforded the title compound. LC/MS=265 [M+1]. ¹H-NMR (CDCl₃, 400 MHz) δ 7.70 (s, 1H), 7.57 (s, 1H), 3.84 (s, 2H), 1.25 (s, 12H), 0.89 (s, 9H).

Intermediate A2

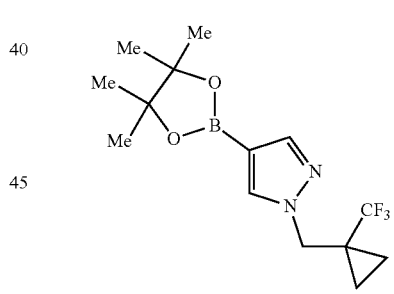

4-(4,4,5,5-tetramethyl-1,3,2-dioxaborolan-2-yl)-1-((1-(trifluoromethyl)cyclopropyl)methyl)-1H-pyrazole To a tetrahydrofuran (22 mL) solution of triphenylphosphine (4.60 g, 17.5 mmol), (1-(trifluoromethyl)cyclopropyl)methanol (2.46 g, 17.5 mmol), and 4-(4,4,5,5-tetramethyl-1,3,2-dioxaborolan-2-yl)-1H-pyrazole (1.7 g, 8.76 mmol) at 0° C. was added a tetrahydrofuran (22 mL) solution of diisopropyl azodicarboxylate (3.41 mL, 17.5 mmol) dropwise. The reaction mixture was allowed to warm to room temperature and stirred for 12 hours. It was concentrated in vacuo, and the residue was sonicated with hexanes (20 mL) to extract the desired product.
Concentration of the hexanes washings afforded the title compound. LC/MS=317 [M+1]. ¹H-NMR (CDCl₃, 400

MHz) δ 7.79 (s, 1H), 7.75 (s, 1H), 4.42 (s, 2H), 1.32 (s, 12H), 1.05-1.11 (m, 2H), 0.93-0.98 (m, 2H).

Intermediate A3

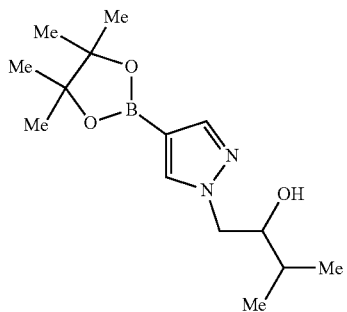 [SMILES: CC(C)C(O)Cn1cc(B2OC(C)(C)C(C)(C)O2)cn1]

3-methyl-1-(4-(4,4,5,5-tetramethyl-1,3,2-dioxaborolan-2-yl)-1H-pyrazol-1-yl)butan-2-ol To a N,N-dimethylformamide (15 mL) solution of 4-(4,4,5,5-tetramethyl-1,3,2-dioxaborolan-2-yl)-1H-pyrazole (250 mg, 1.29 mmol) was added cesium carbonate (1260 mg, 3.87 mmol), followed by a N,N-dimethylformamide (2 mL) solution of 2-isopropyloxirane (222 mg, 2.58 mmol). The reaction mixture was irradiated with microwaves at 120° C. for 45 minutes. It was cooled to room temperature and diluted with water (15 mL). The aqueous layer was extracted with ethyl acetate (25 mL×3). The combined organic extracts were washed with brine (15 mL×2), dried (sodium sulfate), filtered, and concentrated in vacuo to afford the crude product. Purification by column chromatography over silica gel, eluting with petroleum ether/ethyl acetate, afforded the title compound. LC/MS=281 [M+1]. $^1$H-NMR (CD$_3$OD, 400 MHz) δ 7.84 (s, 1H), 7.67 (s, 1H), 4.23-4.27 (m, 1H), 4.02-4.07 (m, 2H), 1.60-1.69 (m, 1H), 1.31 (s, 12H), 0.98 (d, J=6.0 Hz, 6H).

INTERMEDIATE B1

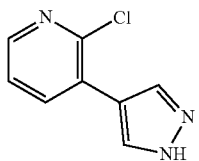 [SMILES: Clc1ncccc1-c1cn[nH]c1]

2-chloro-3-(1H-pyrazol-4-yl)pyridine

Step 1: tert-butyl 4-(2-chloropyridin-3-yl)-1H-pyrazole-1-carboxylate

A mixture of 2-chloro-3-iodopyridine (8.30 g, 34.7 mmol), tert-butyl 4-(4,4,5,5-tetramethyl-1,3,2-dioxaborolan-2-yl)-1H-pyrazole-1-carboxylate (9.99 g, 34.0 mmol), [1,1'-bis(di-tert-butylphosphino)ferrocene]dichloropalladium(II) (2.26 g, 3.47 mmol) and sodium carbonate (7.35 g, 69.3 mmol) was charged with dioxane (120 mL), and the reaction mixture was heated to 65° C. for 1 hour. The reaction mixture was diluted with ethyl acetate (500 mL) and washed with water (200 mL). The aqueous layer was extracted with ethyl acetate (300 mL). The combined organic extracts were washed with brine (200 mL), dried (magnesium sulfate), filtered, and concentrated in vacuo to afford the title compound, which was used in the subsequent reaction without further purification. LC/MS=280 [M+1].

Step 2: 2-chloro-3-(1H-pyrazol-4-yl)pyridine

To a dichloromethane (40 mL) solution of tert-butyl 4-(2-chloropyridin-3-yl)-1H-pyrazole-1-carboxylate (crude from the prior step) was added trifluoroacetic acid (20 mL, 260 mmol). The reaction mixture was stirred at room temperature for 1 hour. It was then concentrated in vacuo, quenched with saturated aqueous sodium hydrogen carbonate solution (200 mL), and extracted with dichloromethane (200 mL×2). The combined organic extracts were dried (magnesium sulfate), filtered, and concentrated in vacuo to afford the crude product. Purification by column chromatography over silica gel, eluting with dichloromethane/ethyl acetate, afforded the title compound. LC/MS=180 [M+1]. $^1$H-NMR (CDCl$_3$, 400 MHz) δ 8.32 (dd, J=1.8, 4.8 Hz, 1H), 8.02 (br s, 2H), 7.82 (dd, J=2.0, 7.7 Hz, 1H), 7.29 (dd, J=4.6, 7.7 Hz, 1H).

The following examples in Table B were prepared similarly as INTERMEDIATE B1 with the appropriate 2-chloro-3-bromopyridine or 2-chloro-3-iodopyridine in step 1.

TABLE B

| Ex | Structure | Name | MS M + 1) |
|----|-----------|------|-----------|
| B2 | ![structure] | 2-chloro-6-methyl-3-(1H-pyrazol-4-yl)pyridine | 194 |
| B3 | ![structure] | 6-chloro-5-(1H-pyrazol-4-yl)picolinonitrile | 205 |

Intermediate B4

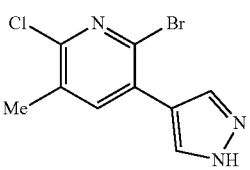 [SMILES: Cc1cc(-c2cn[nH]c2)c(Br)nc1Cl]

2-bromo-6-chloro-5-methyl-3-(1H-pyrazol-4-yl)pyridine

Step 1: 2-bromo-6-chloro-5-methyl-3-(1-(tetrahydro-2H-pyran-2-yl)-1H-pyrazol-4-yl)pyridine To a round-bottom flask were added 2-bromo-6-chloro-3-iodo-5-methylpyridine (2.00 g, 6.02 mmol), 1-(tetrahydro- 2H-pyran-2-yl)-4-(4,4,5,5-tetramethyl-1,3,2-dioxaborolan-2-yl)-1H-pyrazole (1.84 g, 6.62 mmol), [1,1'-bis(diphenylphosphino)ferrocene]dichloro palladium(II) (440 mg, 0.602 mmol), potassium carbonate (2.50 g, 18.1 mmol), dioxane (50 mL) and water (4 mL). The reaction mixture was stirred at 50° C. for 18 hours. It was filtered and concentrated in vacuo. Purification by column chromatography over silica gel, eluting with petroleum ether/ethyl acetate, afforded the title compound. LC/MS=356 [M+1]. $^1$H-NMR (CDCl$_3$, 400 MHz) δ 8.05 (s, 1H), 7.82 (s, 1H), 7.55 (s, 1H), 5.44 (t, J=6.0 Hz, 1H), 4.07-4.10 (m, 1H), 3.71-3.78 (m, 1H), 2.35 (s, 3H), 2.11-2.13 (m, 2H), 1.69-1.72 (m, 4H).

Step 2: 2-bromo-6-chloro-5-methyl-3-(1H-pyrazol-4-yl)pyridine

To a round-bottom flask were added 2-bromo-6-chloro-5-methyl-3-(1-(tetrahydro-2H-pyran-2-yl)-1H-pyrazol-4-yl)pyridine (600 mg, 1.68 mmol) and a 4.0 N ethyl acetate solution of hydrogen chloride (10.0 mL, 40 mmol). The reaction mixture was stirred at 25° C. for 1.5 hours. It was adjusted to pH 8-9 with saturated aqueous sodium hydrogencarbonate solution. The aqueous layer was extracted with dichloromethane (15 mL×3). The mixture was dried (sodium sulfate), filtered, and concentrated in vacuo. Purification by column chromatography over silica gel, eluting with petroleum ether/ethyl acetate, afforded the title compound. LC/MS=272 [M+1]. $^1$H-NMR (CD$_3$OD, 400 MHz) δ 8.36 (s, 2H), 7.91 (s, 1H), 2.40 (s, 3H).

Intermediate C1

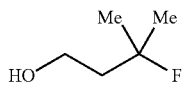

3-fluoro-3-methylbutan-1-ol

Step 1: ethyl 3-fluoro-3-methylbutanoate

To a dichloromethane (15 mL) solution of ethyl 3-hydroxy-3-methylbutanoate (750 mg, 5.1 mmol) at −78° C. was added bis(2-methoxyethyl)aminosulfur trifluoride (1.25 g, 5.6 mmol). The reaction mixture was then allowed to warm up to room temperature and stirred for 4 hours. It was quenched with saturated aqueous sodium hydrogen carbonate solution (10 mL), and the aqueous layer was extracted with dichloromethane (10 mL). The combined organic extracts were washed with saturated aqueous ammonium chloride (10 mL), dried (magnesium sulfate), filtered and concentrated in vacuo to afford the title compound, which was used in the subsequent reaction without further purification. $^1$H-NMR (CDCl$_3$, 400 MHz) δ 4.16 (q, J=7.1 Hz, 2H), 2.66 (d, J=15.9 Hz, 2H), 1.49 (d, J=21.8 Hz, 6H), 1.28 (t, J=7.1 Hz, 3H).

Step 2: 3-fluoro-3-methylbutan-1-ol

To a diethyl ether (15 mL) solution of ethyl 3-fluoro-3-methylbutanoate (crude from the prior step) at −78° C. was added lithium aluminum hydride (251 mg, 6.6 mmol). The reaction mixture was stirred at −78° C. for 5 minutes, then allowed to warm up to room temperature and stirred for 1 hour. It was cooled down to −78° C., and quenched with saturated water (250 μL), 2.5 M aqueous sodium hydroxide solution (250 μL), and water (750 μL). The reaction mixture was then warmed up to room temperature for 15 minutes and diluted with diethyl ether (30 mL). It was filtered, and the residue was washed with diethyl ether (10 mL). The combined filtrate was washed with brine (15 mL), dried (magnesium sulfate), filtered and concentrated in vacuo to afford the title compound, which was used in the subsequent reaction without further purification. $^1$H-NMR (CDCl$_3$, 400 MHz) δ 3.84 (t, J=6.0 Hz, 2H), 1.92 (td, J=6.4, 20.8 Hz, 2H), 1.42 (d, J=21.8 Hz, 6H).

Intermediate C2

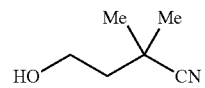

4-hydroxy-2,2-dimethylbutanenitrile

Step 1: (2-bromoethoxy)(tert-butyl)diphenylsilane

To a dichloromethane (60 mL) solution of 2-bromoethanol (2.5 g, 20.0 mmol) and imidazole (3.40 g, 50.0 mmol) at 0° C. was added tert-butylchlorodiphenylsilane (6.60 g, 24.0 mmol). The reaction mixture was stirred at 0° C. for 30 minutes, then warmed up to 17° C. and stirred for 16 hours. It was diluted with dichloromethane (50 mL), washed with water (50 mL), 1.0 M hydrochloric acid (50 mL), water (50 mL), dried (sodium sulfate), filtered, and concentrated in vacuo to afford the crude product. Purification by column chromatography over silica gel, eluting with petroleum ether/ethyl acetate, afforded the title compound. $^1$H-NMR (CD$_3$OD, 400 MHz) δ 7.58-7.75 (m, 4H), 7.26-7.48 (m, 6H), 3.89 (t, J=5.6 Hz, 2H), 3.45 (t, J=5.6 Hz, 2H), 1.03 (s, 9H).

Step 2: 4-((tert-butyldiphenylsilyl)oxy)-2,2-dimethylbutanenitrile

To a tetrahydrofuran (25 mL) solution of isobutyronitrile (0.499 g, 7.22 mmol) at −78° C. was added 2.0 M solution of lithium diisopropylamide (3.61 mL, 7.22 mmol) dropwise under an atmosphere of nitrogen. The reaction mixture was stirred at −78° C. for 30 minutes. Then a tetrahydrofuran (5 mL) solution of (2-bromoethoxy)(tert-butyl)diphenylsilane (2.50 g, 6.88 mmol) was added in 5 min. The reaction mixture was stirred at −78° C. for 1 hour, then at −18° C. for 18 hours. Saturated aqueous ammonium chloride (20 mL) was added to the reaction mixture to quench the reaction. The aqueous layer was extracted with ethyl acetate (50 mL). The combined organic extracts were washed with brine, dried (sodium sulfate), filtered, and concentrated in vacuo to afford the crude product. Purification by column chromatography over silica gel, eluting with petroleum ether/ethyl acetate, afforded the title compound. $^1$H-NMR (CD$_3$OD, 400 MHz) δ 7.58-7.75 (m, 4H), 7.26-7.48 (m, 6H), 3.78 (t, J=5.6 Hz, 2H), 1.77 (t, J=5.6 Hz, 2H), 1.34 (s, 6H), 1.03 (s, 9H).

Step 3: 4-hydroxy-2,2-dimethylbutanenitrile

To a tetrahydrofuran (2.0 mL) solution of 4-((tert-butyldiphenylsilyl)oxy)-2,2-dimethylbutanenitrile (0.70 g, 1.99 mmol) at 0° C. was added a 1.0 M tetrahydrofuran solution of tetrabutylammonium fluoride (3.0 mL, 3.0 mmol). The reaction mixture was then warmed up to 18° C. and stirred for 16 hours to afford the title compound, which was used in the subsequent reaction without further purification.

Intermediate C3

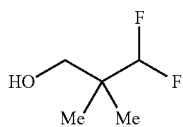

3,3-difluoro-2,2-dimethylpropan-1-ol

Step 1: methyl 3-((tert-butyldiphenylsilyl)oxy)-2,2-dimethylpropanoate

To a N,N-dimethylformamide (50 mL) solution of methyl 3-hydroxy-2,2-dimethylpropanoate (5.00 g, 37.8 mmol) and imidazole (5.15 g, 76 mmol) was added tert-butylchlorodiphenylsilane (11.4 g, 41.6 mmol). The reaction mixture was stirred at 25° C. under an atmosphere of nitrogen for 16 hours. It was diluted with water (15 mL) and extracted with ethyl acetate (100 mL×2). The combined organic extracts were washed with brine (15 mL×2), dried (sodium sulfate), filtered and concentrated in vacuo. Purification by column chromatography over silica gel, eluting with petroleum ether/ethyl acetate, afforded the title compound. $^1$H-NMR (CDCl$_3$, 400 MHz) δ 7.46-7.67 (m, 4H), 7.38-7.42 (m, 6H), 3.69 (s, 3H), 3.65 (s, 2H), 1.21 (s, 6H), 1.04 (s, 9H).

Step 2: 3-((tert-butyldiphenylsilyl)oxy)-2,2-dimethylpropan-1-ol

To a tetrahydrofuran (10 mL) solution of methyl 3-((tert-butyldiphenylsilyl)oxy)-2,2-dimethylpropanoate (4 g, 10.79 mmol) at 0° C. was added lithium borohydride (0.269 g, 13.0 mmol). The reaction mixture was stirred at 25° C. for 12 hours. It was quenched with water (10 mL) and extracted with ethyl acetate (20 mL×3). The combined organic extracts were washed with brine (30 mL×2), filtered, and concentrated in vacuo to afford the title compound as the crude product. It was used in the subsequent reaction without further purification. $^1$H-NMR (CDCl$_3$, 400 MHz) δ 7.65-7.66 (m, 4H), 7.39-7.41 (m, 6H), 3.50 (s, 2H), 3.46 (s, 2H), 1.05 (s, 9H), 0.88 (s, 6H).

Step 3: 3-((tert-butyldiphenylsilyl)oxy)-2,2-dimethylpropanal

To an ethyl acetate (20 mL) solution of 3-((tert-butyldiphenylsilyl)oxy)-2,2-dimethylpropan-1-ol (3.50 g, 10.2 mmol) was added 2-iodoxybenzoic acid (2.86 g, 10.2 mmol) under an atmosphere of nitrogen. The reaction mixture was stirred at 80° C. for 12 hours. Water (10 mL) was added to the reaction mixture, and the aqueous layer was extracted with ethyl acetate (50 mL×3). The combined organic extracts were washed with brine (50 mL×2), filtered, and concentrated in vacuo to afford the title compound as the crude product. It was used in the subsequent reaction without further purification. $^1$H-NMR (CDCl$_3$, 400 MHz) δ 9.75 (s, 1H), 7.62-7.68 (m, 4H), 7.39-7.40 (m, 6H), 3.62 (s, 2H), 1.06 (s, 6H), 1.03 (s, 9H).

Step 4: tert-butyl(3,3-difluoro-2,2-dimethylpropoxy)diphenylsilane

To a dichloromethane (20 mL) solution of 3-((tert-butyldiphenylsilyl)oxy)-2,2-dimethylpropanal (3.30 g, 9.69 mmol) at −78° C. was added (diethylamino)sulfur trifluoride (3.12 g, 19.4 mmol). The reaction mixture was stirred at 0° C. for 2 hours and quenched with saturated aqueous sodium hydrogencarbonate (15 mL), The aqueous layer was extracted with ethyl acetate (50 mL×3). The combined organic extracts were washed with brine (50 mL×2), filtered, and concentrated in vacuo. Purification by column chromatography over silica gel, eluting with petroleum ether/ethyl acetate, afforded the title compound. $^1$H-NMR (CDCl$_3$, 400 MHz) δ 7.62-7.78 (m, 4H), 7.27-7.47 (m, 6H), 5.35 (t, J=112.4 Hz, 1H), 3.49 (s, 2H), 1.05 (s, 9H), 0.99 (s, 6H).

Step 5: 3,3-difluoro-2,2-dimethylpropan-1-ol

To a tetrahydrofuran (15 mL) solution of tert-butyl(3,3-difluoro-2,2-dimethylpropoxy)diphenylsilane (1.50 g, 4.14 mmol) at 0° C. was added a 1.0 M tetrahydrofuran solution of tetrabutylammonium fluoride (6.21 mL, 6.21 mmol). The reaction mixture was stirred at 20° C. under an atmosphere of nitrogen for 16 hours. It was diluted with water (15 mL), and the aqueous layer was extracted with ethyl acetate (25 mL×3). The combined organic extracts were dried (sodium sulfate), filtered, and concentrated in vacuo. Purification by column chromatography over silica gel, eluting with petroleum ether/ethyl acetate, afforded the title compound. $^1$H-NMR (CDCl$_3$, 400 MHz) δ 5.69 (t, J=114 Hz, 1H), 3.52 (s, 2H), 0.99 (s, 6H).

Intermediate C4

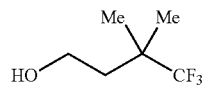

4,4,4-trifluoro-3,3-dimethylbutan-1-ol

In a round-bottom flask, a tetrahydrofuran (2 mL) solution of 4,4,4-trifluoro-3,3-dimethylbutanoic acid (150 mg, 0.882 mmol) at 0° C. was charged with lithium aluminium hydride (33.5 mg, 0.882 mmol) in one portion under an atmosphere of nitrogen. The reaction mixture stirred at 0° C. for 2 hours. The reaction mixture was quenched with ethyl acetate (0.5 mL). It was dried (sodium sulfate) and concentrated in vacuo to afford the title compound as the crude product, which was used in the subsequent reaction without further purification. $^1$H-NMR (CDCl$_3$, 400 MHz) δ 3.76 (t, J=7.2 Hz, 2H), 1.78 (t, J=7.2 Hz, 2H), 1.14 (s, 6H).

The following examples in Table C were prepared similarly as INTERMEDIATE C4 with the appropriate carboxylic acid, ester or aldehyde.

TABLE C

| Ex | Structure | Name |
|---|---|---|
| C5 | 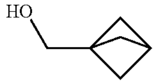 | bicyclo[1.1.1]pentan-1-ylmethanol |
| C6 | 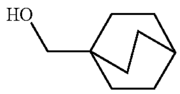 | bicyclo[2.2.2]octan-1-ylmethanol |
| C7 | 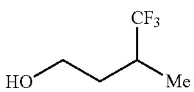 | 4,4,4-trifluoro-3-methylbutan-1-ol |
| C8 | 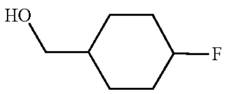 | (4-fluorocyclohexyl)methanol |
| C9 | 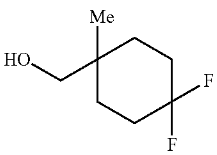 [SMILES: CC1(CO)CCC(F)(F)CC1] | (4,4-difluoro-1-methylcyclohexyl)methanol |
| C10 | 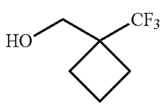 | (1-(trifluoromethyl)cyclobutyl)methanol |
| C11 | 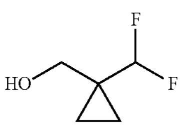 | (1-(difluoromethyl)cyclopropyl)methanol |
| C12 | 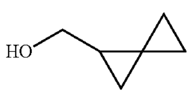 | spiro[2.2]pentan-1-ylmethanol |
| C13 | 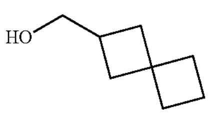 | spiro[3.3]heptan-2-ylmethanol |
| C14 | 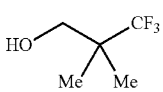 | 3,3,3-trifluoro-2,2-dimethylpropan-1-ol |

Intermediate C15

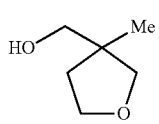

(3-methyltetrahydrofuran-3-yl)methanol

Step 1: benzyl tetrahydrofuran-3-carboxylate

To a mixture of tetrahydrofuran-3-carboxylic acid (25 g, 215 mmol), benzyl bromide (38.4 mL, 323 mmol), and potassium carbonate (89 g, 646 mmol) was charged N,N-dimethylformamide (200 mL). It was stirred at 80° C. for 24 hours, cooled down and diluted with water (600 mL). The aqueous layer was extracted with ethyl acetate (200 mL×3), and the combined organic extracts were dried (magnesium sulfate), filtered, and concentrated in vacuo. Purification by column chromatography over silica gel, eluting with hexanes/ethyl acetate, afforded the title compound. $^1$H-NMR (CDCl$_3$, 500 MHz) δ 7.28-7.42 (m, 5H), 5.15 (s, 2H), 3.92-4.02 (m, 2H), 3.89 (dt, J=6.4, 8.0 Hz, 1H), 3.78-3.84 (m, 1H), 3.07-3.20 (m, 1H), 2.23 (tdd, J=6.2, 7.7, 12.5 Hz, 1H), 2.09-2.18 (m, 1H).

Step 2: benzyl 3-methyltetrahydrofuran-3-carboxylate

To a 1.0 M tetrahydrofuran solution of lithium bis(trimethylsilyl)amide (160 mL, 160 mmol) at −78° C. was added a tetrahydrofuran (100 mL) solution of benzyl tetrahydrofuran-3-carboxylate (11.0 g, 53.3 mmol) slowly. After addition, the reaction mixture was stirred at −78° C. for 30 minutes before iodomethane (16.7 mL, 267 mmol) was added. The reaction mixture was slowly warmed to room temperature and stirred for 14 hours. It was diluted with water (200 mL), and the aqueous layer was extracted with ethyl acetate (200 mL×3). The combined organic extracts were dried (magnesium sulfate), filtered, and concentrated in vacuo. Purification by column chromatography over silica gel, eluting with hexanes/ethyl acetate, afforded the title compound. $^1$H-NMR (CDCl$_3$, 500 MHz) δ 7.15-7.25 (m, 5H), 5.01 (d, J=12.8 Hz, 1H), 4.99 (d, J=12.7 Hz, 1H), 3.96 (d, J=8.8 Hz, 1H), 3.75 (t, J=7.1 Hz, 2H), 3.40 (d, J=8.7 Hz, 1H), 2.33 (td, J=7.1, 12.7 Hz, 1H), 1.62 (td, J=7.2, 12.6 Hz, 1H), 1.23 (s, 3H).

Step 3: (3-methyltetrahydrofuran-3-yl)methanol

To a tetrahydrofuran (30 mL) solution of benzyl 3-methyltetrahydrofuran-3-carboxylate (8.4 g, 38.1 mmol) at −78° C. was added a 2.3 M tetrahydrofuran solution of lithium aluminium hydride (33.2 mL, 76 mmol). After addition, the reaction mixture was slowly warmed to room temperature and stirred for 48 hours. It was quenched with water at −78° C. The aqueous layer was extracted with ethyl acetate (200 mL×3), and the combined organic extracts were dried (magnesium sulfate), filtered, and concentrated in vacuo. Purification by column chromatography over silica gel, eluting with hexanes/ethyl acetate, afforded the title compound. $^1$H-NMR (CDCl$_3$, 500 MHz) δ 3.79-3.92 (m, 2H), 3.70 (d, J=8.6 Hz, 1H), 3.46 (s, 2H), 3.36 (d, J=8.6 Hz, 1H), 2.25 (s br, 1H), 1.78-1.88 (m, 1H), 1.60 (ddd, J=6.0, 8.1, 12.4 Hz, 1H), 1.10 (s, 3H).

Intermediate C16

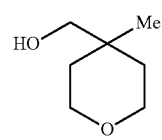

(4-methyltetrahydro-2H-pyran-4-yl)methanol

The title compound was made by following the procedures described for INTERMEDIATE C15, substituting methyl tetrahydro-2H-pyran-4-carboxylate for benzyl tetrahydrofuran-3-carboxylate in Step 2.

Intermediate D1

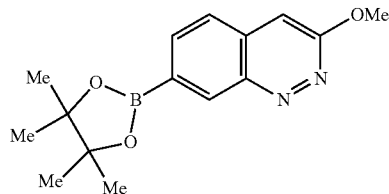 [SMILES: COc1cc2ccc(B3OC(C)(C)C(C)(C)O3)cc2nn1]

3-methoxy-7-(4,4,5,5-tetramethyl-1,3,2-dioxaborolan-2-yl)cinnoline

A mixture of 7-bromo-3-methoxycinnoline (3.00 g, 12.6 mmol), bis(pinacolato) diboron (3.19 g, 12.6 mmol), and potassium acetate (3.69 g, 37.6 mmol) was charged with tetrahydrofuran (20 mL) and degassed. [1,1'-Bis(di-tert-butylphosphino)ferrocene]dichloropalladium(II) (0.41 g, 0.63 mmol) was added, and the reaction mixture was heated to 60° C. for 2 hours. The reaction mixture was cooled down to room temperature, diluted with water (75 mL), and extracted with ethyl acetate (100 mL×2). The combined organic extracts were washed with brine (50 mL), dried (magnesium sulfate), filtered, and concentrated in vacuo to afford the crude product. Purification by column chromatography over silica gel, eluting with dichloromethane/ethyl acetate, gave the purified fractions. They were concentrated in vacuo, and the residual solid was washed by diethyl ether and hexanes to afford the title compound. $^1$H-NMR (CDCl$_3$, 400 MHz) δ 8.87 (d, J=0.7 Hz, 1H), 7.92 (dd, J=1.0, 8.4 Hz, 1H), 7.65 (d, J=8.4 Hz, 1H), 7.22 (s, 1H), 4.31 (s, 3H), 1.40 (s, 12H).

Intermediate D2

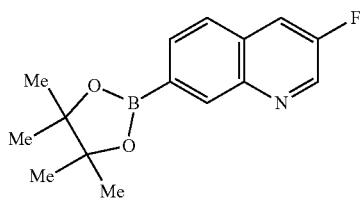 [SMILES: CC1(C)OB(c2ccc3cc(F)cnc3c2)OC1(C)C]

3-fluoro-7-(4,4,5,5-tetramethyl-1,3,2-dioxaborolan-2-yl)quinoline

Step 1: (2-amino-4-bromophenyl)methanol

To a tetrahydrofuran (30 mL) solution of methyl 2-amino-4-bromobenzoate (3.00 g, 13.0 mmol) at 0° C. was added lithium borohydride (0.710 g, 32.6 mmol). The reaction mixture was stirred at 10° C. for 16 hours. It was poured into water (50 mL) and extracted with ethyl acetate (200 mL). The combined organic extracts were dried (sodium sulfate), filtered and concentrated in vacuo to afford the title compound as the crude product. It was used in the subsequent reaction without further purification.

Step 2: 2-amino-4-bromobenzaldehyde

To a dichloromethane (20 mL) solution of (2-amino-4-bromophenyl)methanol (0.30 g, 1.50 mmol) was added manganese (IV) oxide (0.645 g, 7.42 mmol). The reaction mixture was stirred at 15° C. for 16 hours, filtered and concentrated in vacuo to afford the title compound as the crude product. It was used in the subsequent reaction without further purification.

Step 3: 2-(7-bromoquinolin-3-yl)isoindoline-1,3-dione

To a mixture of 2-(2,2-diethoxyethyl)isoindoline-1,3-dione (139 mg, 0.528 mmol), 2-amino-4-bromobenzaldehyde (88 mg, 0.44 mmol) and p-toluenesulfonic acid (84 mg, 0.44 mmol) was charged toluene (5 mL), and the reaction mixture was stirred at 120° C. for 16 hours. It was cooled to room temperature, filtered and concentrated in vacuo to afford the crude product. It was dissolved in dichloromethane (30 mL) and washed with saturated aqueous sodium hydrogencarbonate (10 mL). The combined organic extracts were dried (sodium sulfate), filtered, and concentrated in vacuo. Purification by column chromatography over silica gel, eluting with petroleum ether/ethyl acetate, afforded the title compound. LC/MS=353 [M+1]. $^1$H-NMR (CD$_3$OD, 400 MHz) δ 9.08 (d, J=2.0 Hz, 1H), 8.37 (s, 1H), 8.31 (s, 1H), 8.03 (dd, J=2.8, 5.2 Hz, 2H), 7.87 (dd, J=2.8, 5.2 Hz, 2H), 7.76-7.81 (m, 1H), 7.69-7.74 (m, 1H).

Step 4: 7-bromoquinolin-3-amine

To a mixture of 2-(7-bromoquinolin-3-yl)isoindoline-1,3-dione (100 mg, 0.283 mmol) and hydrazine (1.0 mL, 31.9 mmol) was charged ethanol (15 mL), and the reaction mixture was stirred at 100° C. for 16 hours. The reaction mixture was cooled to room temperature and concentrated in vacuo. Purification by column chromatography over silica gel, eluting with petroleum ether/ethyl acetate, afforded the title compound. LC/MS=223 [M+1]. $^1$H-NMR (CDCl$_3$, 400 MHz) δ 8.48 (d, J=2.4 Hz, 1H), 8.11 (s, 1H), 7.49 (dd, J=1.6, 8.8 Hz, 1H), 7.45 (d, J=8.8 Hz, 1H), 7.19 (d, J=2.4 Hz, 1H), 3.93 (br s, 2H).

Step 5: 7-bromo-3-fluoroquinoline

To 7-bromoquinolin-3-amine (50 mg, 0.224 mmol) was charged boron trifluoride dihydrate (0.5 mL, 7.88 mmol), followed by sodium nitrite (17.0 mg, 0.247 mmol). The reaction mixture was stirred at 100° C. for 16 hours. It was cooled to room temperature, and saturated aqueous sodium carbonate was added until pH reached 10. The aqueous layer was extracted with ethyl acetate (20 mL), and the combined organic extracts were dried (magnesium sulfate), filtered, and concentrated in vacuo to afford the crude product. Purification by column chromatography over silica gel, eluting with petroleum ether/tetrahydrofuran, gave the purified fractions. LC/MS=226 [M+1]. $^1$H-NMR (CDCl$_3$, 400 MHz) δ 8.96 (d, J=2.4 Hz, 1H), 8.30 (dd, J=2.4, 9.2 Hz, 1H), 8.27 (s, 1H), 7.95 (d, J=8.4 Hz, 1H), 7.80 (d, J=8.4 Hz, 1H).

Step 6: 3-fluoro-7-(4,4,5,5-tetramethyl-1,3,2-dioxaborolan-2-yl)quinoline

The title compound was made by following the procedures described for INTERMEDIATE D1, substituting 7-bromo-3-fluoroquinoline for 7-bromo-3-methoxycinnoline. LC/MS=274 [M+1].

Intermediate D3 Intermediate D4

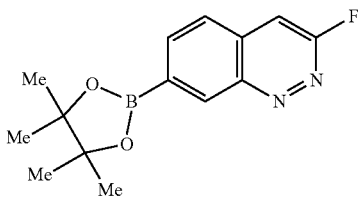

3-chloro-7-(4,4,5,5-tetramethyl-1,3,2-dioxaborolan-2-yl)cinnoline

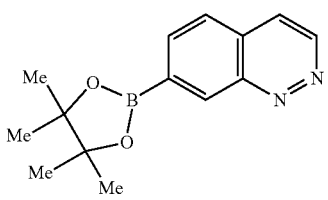

7-(4,4,5,5-tetramethyl-1,3,2-dioxaborolan-2-yl)cinnoline

The title compounds were obtained as a mixture by following the procedures described for INTERMEDIATE D1, substituting 7-bromo-3-chlorocinnoline for 7-bromo-3-methoxycinnoline. LC/MS=209, 175 [hydrolysis product+1].

Intermediate E1

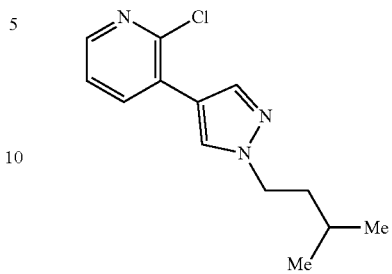

2-chloro-3-(1-isopentyl-1H-pyrazol-4-yl)pyridine

A mixture of 3-bromo-2-chloropyridine (3.64 g, 18.9 mmol), 1-isopentyl-4-(4,4,5,5-tetramethyl-1,3,2-dioxaborolan-2-yl)-1H-pyrazole (5.00 g, 18.9 mmol), tetrakis (triphenylphosphine)palladium(0) (656 mg, 0.57 mmol), and a 2.0 M aqueous solution of sodium carbonate (19.0 mL, 38.0 mmol) was charged with dioxane (180 mL). The reaction mixture was degassed and heated to 80° C. for 3 days. The reaction mixture was filtered, and the filtrate was charged with water (200 mL). The aqueous layer was extracted with ethyl acetate (300 mL×2), and the combined organic extracts were washed with brine (100 mL), dried (magnesium sulfate), filtered and concentrated in vacuo. Purification by column chromatography over silica gel, eluting with dichloromethane/ethyl acetate, afforded the title compound. LC/MS=250 [M+1]. $^1$H-NMR (CDCl$_3$, 400 MHz) δ 8.28 (dd, J=1.9, 4.7 Hz, 1H), 7.90 (s, 1H), 7.81 (s, 1H), 7.80 (dd, J=1.9, 7.7 Hz, 1H), 7.24-7.28 (m, 1H), 4.20 (t, J=7.5 Hz, 2H), 1.82 (q, J=7.3 Hz, 2H), 1.58-1.69 (m, 1H), 0.98 (d, J=6.6 Hz, 6H).

The following examples in Table E were prepared similarly as INTERMEDIATE E1 with the appropriate bromoarene and pinacol boronate ester (INTERMEDIATE A).

TABLE E

| Ex | Structure | Name | MS (M + 1) |
|---|---|---|---|
| E2 | 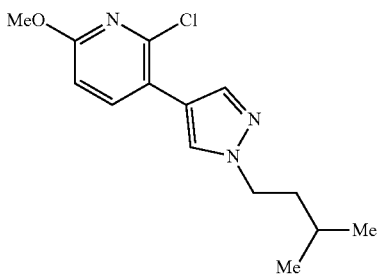 [SMILES: COc1ccc(-c2cnn(CCC(C)C)c2)c(Cl)n1] | 2-chloro-3-(1-isopentyl-1H-pyrazol-4-yl)-6-methoxypyridine | 280 |

TABLE E-continued

| Ex | Name | MS (M + 1) |
|---|---|---|
| E3 | 2-chloro-3-(1-isopentyl-1H-pyrazol-4-yl)-6-(trifluoromethyl)pyridine | 318 |
| E4 | 2-chloro-3-(1-isopentyl-1H-pyrazol-4-yl)-4-methylpyridine | 264 |
| E5 | 2-chloro-3-(1-isopentyl-1H-pyrazol-4-yl)-4-methoxypyridine | 280 |
| E6 | 2,5-dichloro-3-(1-isopentyl-1H-pyrazol-4-yl)pyridine | 284 |
| E7 | 6-chloro-5-(1-isopentyl-1H-pyrazol-4-yl)pyridin-3-amine | 265 |

TABLE E-continued

| Ex | Structure | Name | MS (M + 1) |
|---|---|---|---|
| E8 | 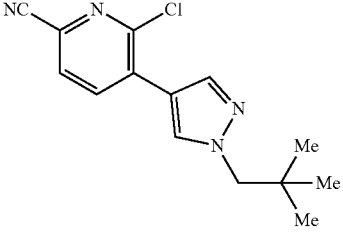 [SMILES: CC(C)(C)Cn1cc(-c2ccc(C#N)nc2Cl)cn1] | 6-chloro-5-(1-neopentyl-1H-pyrazol-4-yl)picolinonitrile | 275 |
| E9 | 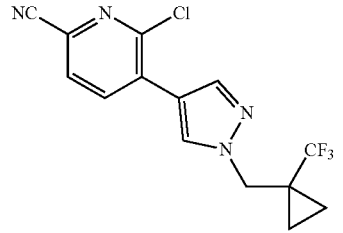 [SMILES: N#Cc1ccc(-c2cnn(CC3(C(F)(F)F)CC3)c2)c(Cl)n1] | 6-chloro-5-(1-((1-(trifluoromethyl)cyclopropyl)methyl)-1H-pyrazol-4-yl)picolinonitrile | 327 |
| E10 | 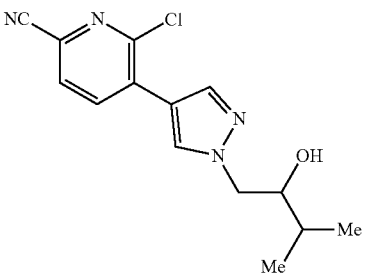 [SMILES: CC(C)C(O)Cn1cc(-c2ccc(C#N)nc2Cl)cn1] | 6-chloro-5-(1-(2-hydroxy-3-methylbutyl)-1H-pyrazol-4-yl)picolinonitrile | 291 |
| E11 | 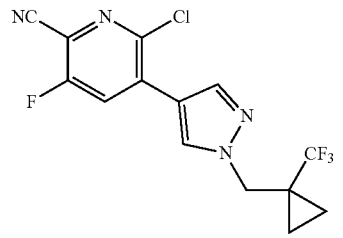 [SMILES: N#Cc1nc(Cl)c(-c2cnn(CC3(C(F)(F)F)CC3)c2)cc1F] | 6-chloro-3-fluoro-5-(1-((1-(trifluoromethyl)cyclopropyl)methyl)-1H-pyrazol-4-yl)picolinonitrile | 345 |
| E12 | 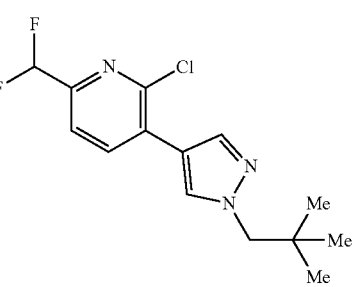 | 2-chloro-6-(difluoromethyl)-3-(1-neopentyl-1H-pyrazol-4-yl)pyridine | 300 |
| E13 | 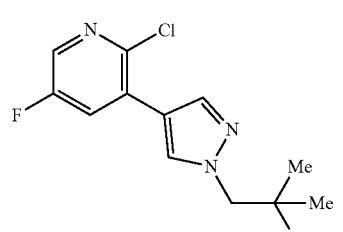 | 2-chloro-5-fluoro-3-(1-neopentyl-1H-pyrazol-4-yl)pyridine | 268 |

TABLE E-continued

| Ex | Structure | Name | MS (M + 1) |
|---|---|---|---|
| E14 | 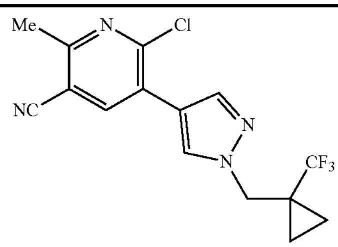 | 6-chloro-2-methyl-5-(1-((1-(trifluoromethyl)cyclopropyl)methyl)-1H-pyrazol-4-yl)nicotinonitrile | 341 |

Intermediate F1

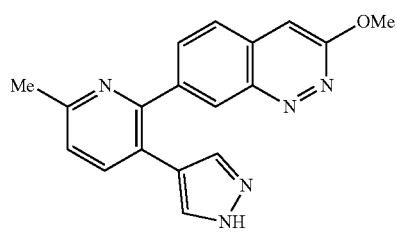 [SMILES: COc1cc2ccc(-c3nc(C#N)ccc3-c3cn[nH]c3)cc2nn1]

3-methoxy-7-(6-methyl-3-(1H-pyrazol-4-yl)pyridin-2-yl)cinnoline

Step 1: tert-butyl 4-(2-chloro-6-methylpyridin-3-yl)-1H-pyrazole-1-carboxylate To a dichloromethane (58.5 mL) suspension of 2-chloro-6-methyl-3-(1H-pyrazol-4-yl)pyridine (INTERMEDIATE B2, 2.83 g, 14.6 mmol) was added N,N-diisopropylethylamine (8.12 mL, 46.5 mmol), followed by di-tert-butyl dicarbonate (4.06 g, 18.6 mmol). The reaction mixture was stirred at room temperature for 12 hours. It was diluted with dichloromethane (200 mL), washed with saturated aqueous sodium hydrogencarbonate (50 mL×2), dried (sodium sulfate), filtered, and concentrated in vacuo to afford the crude product. Purification by column chromatography over silica gel, eluting with hexanes/ethyl acetate, afforded the title compound. LC/MS=294 [M+1].

Step 2: 3-methoxy-7-(6-methyl-3-(1H-pyrazol-4-yl)pyridin-2-yl)cinnoline

In a sealed tube, a 1,4-dioxane (36 mL) solution of tert-butyl 4-(2-chloro-6-methylpyridin-3-yl)-1H-pyrazole-1-carboxylate (3.08 g, 10.5 mmol) was charged with water (6 mL), followed by potassium phosphate (5.56 g, 26.2 mmol) and 3-methoxy-7-(4,4,5,5-tetramethyl-1,3,2-dioxaborolan-2-yl)cinnoline (INTERMEDIATE D1, 3.30 g, 11.5 mmol). The reaction mixture was sparged with nitrogen for 10 minutes, then [1,1'-bis(diphenylphosphino) ferrocene] dichloropalladium(II), complex with dichloromethane (0.428 g, 0.524 mmol) was added. The reaction mixture was degassed three times, the tube was capped, and the reaction mixture was heated to 100° C. for 12 hours. It was diluted with ethyl acetate (200 mL), washed with water (40 mL×3), dried (sodium sulfate), filtered and concentrated in vacuo to afford the crude product. Purification by column chromatography over silica gel, eluting with hexanes/ethyl acetate, afforded the title compound. LC/MS=318 [M+1]. $^1$H-NMR (DMSO-$d_6$, 500 MHz) δ 12.84 (s, 1H), 8.29 (s, 1H), 7.87 (dd, J=8.3, 11.3 Hz, 2H), 7.66-7.72 (m, 2H), 7.60 (s, 1H), 7.34 (d, J=7.9 Hz, 1H), 7.23 (s, 1H), 4.18 (s, 3H), 2.56 (s, 3H).

The following examples in Table F1 were prepared similarly as INTERMEDIATE F1 with the appropriate INTERMEDIATE B and boronic acid or pinacol boronate ester INTERMEDIATE D.

TABLE F1

| Ex | Structure | Name | MS (M + 1) |
|---|---|---|---|
| F2 | 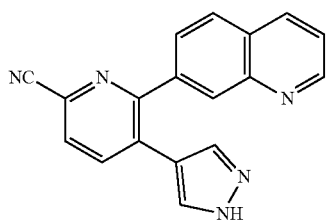 | 5-(1H-pyrazol-4-yl)-6-(quinolin-7-yl)picolinonitrile | 298 |

TABLE F1-continued

| Ex | Structure | Name | MS (M + 1) |
|---|---|---|---|
| F3 | 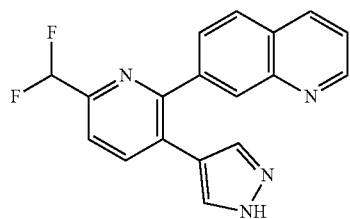 [SMILES: FC(F)c1ccc(-c2cn[nH]c2)c(-c2ccc3cccnc3c2)n1] | 6-(3-methoxycinnolin-7-yl)-5-(1H-pyrazol-4-yl)picolinonitrile | 329 |

Intermediate F4

7-(6-(difluoromethyl)-3-(1H-pyrazol-4-yl)pyridin-2-yl)quinoline

Step 1: 2-chloro-6-(difluoromethyl)-3-(1-(tetrahydro-2H-pyran-2-yl)-1H-pyrazol-4-yl)pyridine To a 10-mL flask were charged 3-bromo-2-chloro-6-(difluoromethyl)pyridine (480 mg, 1.98 mmol), sodium carbonate (525 mg, 4.95 mmol), [1,1'-bis(diphenylphosphino)ferrocene]dichloropalladium(II) (217 mg, 0.297 mmol), 1-(tetrahydro-2H-pyran-2-yl)-4-(4,4,5,5-tetramethyl-1,3,2-dioxaborolan-2-yl)-1H-pyrazole (661 mg, 2.38 mmol), 1,4-dioxane (3 mL) and water (0.6 mL). The resulting reaction mixture was stirred under an atmosphere of nitrogen at 50° C. for 6 hours. It was diluted with water (15 mL), and the aqueous layer was extracted with ethyl acetate (30 mL×3). The combined organic extracts were dried (sodium sulfate), filtered and concentrated in vacuo. Purification by column chromatography over silica gel, eluting with petroleum ether/ethyl acetate, afforded the title compound. LC/MS=314 [M+1]. $^1$H-NMR (CDCl$_3$, 400 MHz) δ 8.14 (s, 1H), 7.94 (d, J=8.0 Hz, 1H), 7.92 (s, 1H), 7.59 (d, J=8.0 Hz, 1H), 6.60 (t, J=55.4 Hz, 1H), 5.45 (t, J=6.0 Hz, 1H), 4.11 (d, J=12.0 Hz, 1H), 3.74 (dt, J=2.7, 10.8 Hz, 1H), 2.13-2.16 (m, 2H), 1.64-1.74 (m, 4H).

Step 2: 7-(6-(difluoromethyl)-3-(1-(tetrahydro-2H-pyran-2-yl)-1H-pyrazol-4-yl)pyridin-2-yl)quinoline To a 10-mL flask were added 2-chloro-6-(difluoromethyl)-3-(1-(tetrahydro-2H-pyran-2-yl)-1H-pyrazol-4-yl)pyridine (60 mg, 0.191 mmol), potassium phosphate trihydrate (153 mg, 0.574 mmol), [1,1'-bis(di-tert-butylphosphino)ferrocene]dichloropalladium(II) (12.5 mg, 0.019 mmol), 7-(4,4,5,5-tetramethyl-1,3,2-dioxaborolan-2-yl)quinoline (53.7 mg, 0.210 mmol), 1,4-dioxane (1 mL) and water (0.3 mL). The resulting reaction mixture was stirred at 70° C. for 12 hours. It was diluted with water (6 mL), and the aqueous layer was extracted with ethyl acetate (10 mL×3). The combined organic extracts were washed with brine (10 mL), dried (sodium sulfate), filtered and concentrated in vacuo. Purification by column chromatography over silica gel, eluting with petroleum ether/ethyl acetate, afforded the title compound. LC/MS=407 [M+1]. $^1$H-NMR (CDCl$_3$, 400 MHz) δ 8.91 (d, J=2.8 Hz, 1H), 8.25 (s, 1H), 8.16 (d, J=8.4 Hz, 1H), 7.94 (d, J=8.0 Hz, 1H), 7.79 (d, J=8.4 Hz, 1H), 7.68 (d, J=8.0 Hz, 1H), 7.58 (d, J=7.2 Hz, 1H), 7.40 (t, J=9.2 Hz, 1H), 7.35 (s, 1H), 6.70 (t, J=55.4 Hz, 1H), 5.24 (t, J=5.8 Hz, 1H), 3.90 (d, J=11.6 Hz, 1H), 3.57 (dt, J=3.8, 8.2 Hz, 1H), 1.85-2.00 (m, 3H), 1.50-1.75 (m, 3H).

Step 3: 7-(6-(difluoromethyl)-3-(1H-pyrazol-4-yl)pyridin-2-yl)quinoline

In a 50-mL flask, 7-(6-(difluoromethyl)-3-(1-(tetrahydro-2H-pyran-2-yl)-1H-pyrazol-4-yl)pyridin-2-yl)quinoline (55 mg, 0.135 mmol) was charged with a 4.0 M dioxane solution of hydrogen chloride (20 mL, 80 mmol). The reaction mixture was stirred for 1 hour. It was concentrated in vacuo to afford the title compound as the crude hydrochloride salt, which was used in the subsequent reaction without further purification. LC/MS=323 [M+1]. $^1$H-NMR (CD$_3$OD, 400 MHz) δ 9.26-9.29 (m, 2H), 8.43 (s, 1H), 8.38 (d, J=8.8 Hz, 1H), 8.25 (d, J=8.0 Hz, 1H), 8.17 (t, 1H), 8.06 (dd, J=1.2, 8.4 Hz, 1H), 7.88 (d, J=8.0 Hz, 1H), 7.55-7.70 (m, 2H), 6.84 (t, J=55.2 Hz, 1H).

The following examples in Table F were prepared similarly as INTERMEDIATE F4 with the appropriate INTERMEDIATE B and boronic acid or pinacol boronate ester INTERMEDIATE D.

TABLE F

| Ex | Structure | Name | MS (M + 1) |
|---|---|---|---|
| F5 | 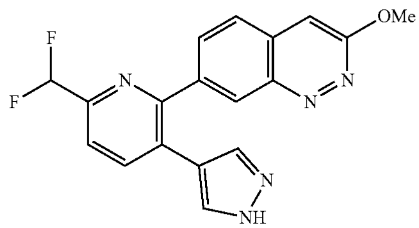 [SMILES: COc1cc2ccc(-c3nc(C(F)F)ccc3-c3cn[nH]c3)cc2nn1] | 7-(6-(difluoromethyl)-3-(1H-pyrazol-4-yl)pyridin-2-yl)-3-methoxycinnoline | 298 |
| F6 | 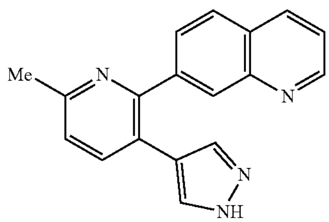 | 7-(6-methyl-3-(1H-pyrazol-4-yl)pyridin-2-yl)quinoline | 287 |

Intermediate F6

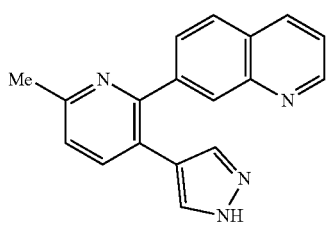

7-(6-methyl-3-(1H-pyrazol-4-yl)pyridin-2-yl)quinoline

Alternatively, intermediate F6 can also be synthesized as follows:

Step 1: 7-(3-bromo-6-methylpyridin-2-yl)quinoline

To a mixture of 2,3-dibromo-6-methylpyridine (3.95 g, 15.7 mmol), quinolin-7-ylboronic acid (2.80 g, 16.2 mmol), tetrakis(triphenylphosphine)palladium(0) (910 mg, 0.787 mmol) and triphenylphosphine (413 mg, 1.57 mmol) was charged tetrahydrofuran (32 mL) and a 2.0 M aqueous solution of potassium carbonate (23.6 mL, 47.2 mmol). The reaction mixture was degassed with nitrogen and heated to 80° C. for 12 hours. The reaction mixture was cooled to room temperature, diluted with ethyl acetate (20 mL), washed with brine (10 mL), dried (sodium sulfate), filtered and concentrated in vacuo. Purification by column chromatography over silica gel, eluting with hexanes/ethyl acetate, afforded the title compound. LC/MS=299 [M+1].

Step 2: tert-butyl 4-(6-methyl-2-(quinolin-7-yl)pyridin-3-yl)-1H-pyrazole-1-carboxylate To a mixture of 7-(3-bromo-6-methylpyridin-2-yl)quinoline (200 mg, 0.669 mmol), tert-butyl 4-(4,4,5,5-tetramethyl-1,3,2-dioxaborolan-2-yl)-1H-pyrazole-1-carboxylate (197 mg, 0.669 mmol), [1,1'-bis(diphenylphosphino)ferrocene]dichloropalladium(II), complex with dichloromethane (27.3 mg, 0.033 mmol) and potassium phosphate (426 mg, 2.01 mmol) was charged dioxane (3.0 mL) and water (0.4 mL). The reaction mixture was heated at 100° C. for 2 hours, cooled to room temperature, filtered and concentrated in vacuo. Purification by column chromatography over silica gel, eluting with hexanes/ethyl acetate, afforded the title compound. LC/MS=387 [M+1].

Step 3: 7-(6-methyl-3-(1H-pyrazol-4-yl)pyridin-2-yl)quinoline

To a dichloromethane (3.3 mL) solution of tert-butyl 4-(6-methyl-2-(quinolin-7-yl)pyridin-3-yl)-1H-pyrazole-1-carboxylate (153 mg, 0.396 mmol) was charged trifluoroacetic acid (0.66 mL). The reaction mixture was stirred for 0.5 hour. It was concentrated in vacuo to afford the title compound as the crude hydrochloride salt, which was used in the subsequent reaction without further purification. LC/MS=287 [M+1].

Intermediate F7

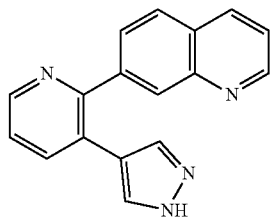 [SMILES: c1cnc(-c2ccc3cccnc3c2)c(-c2cn[nH]c2)c1]

7-(3-(1H-pyrazol-4-yl)pyridin-2-yl)quinoline

Step 1: 2-chloro-3-(1-(4-methoxybenzyl)-1H-pyrazol-4-yl)pyridine

To a mixture of 2-chloro-3-iodopyridine (0.80 g, 3.3 mmol), 1-(4-methoxybenzyl)-4-(4,4,5,5-tetramethyl-1,3,2-dioxaborolan-2-yl)-1H-pyrazole (1.0 g, 3.2 mmol), and

[1,1'-bis(di-tert-butylphosphino)ferrocene]dichloropalladium(II) (104 mg, 0.159 mmol) was charged tetrahydrofuran (5 mL), followed by a 2.0 M aqueous solution of sodium carbonate (1.6 mL, 3.2 mmol). The reaction mixture was stirred at 50° C. for 1 hour and 40° C. for 18 hours. The reaction mixture was charged with additional [1,1'-bis(di-tert-butylphosphino)ferrocene]dichloropalladium(II) (104 mg, 0.159 mmol) and heated to 65° C. for 2 hours. It was cooled to room temperature and charged with water (20 mL). The aqueous layer was extracted with ethyl acetate (25 mL×2), and the combined organic extracts were washed with brine (10 mL), dried (magnesium sulfate), filtered, and concentrated in vacuo. Purification by column chromatography over silica gel, eluting with dichloromethane/ethyl acetate, afforded the title compound. LC/MS=300 [M+1].

Step 2: 7-(3-(1-(4-methoxybenzyl)-1H-pyrazol-4-yl)pyridin-2-yl)quinoline

To a mixture of 2-chloro-3-(1-(4-methoxybenzyl)-1H-pyrazol-4-yl)pyridine (590 mg, 2.0 mmol), 7-(4,4,5,5-tetramethyl-1,3,2-dioxaborolan-2-yl)quinoline (530 mg, 2.1 mmol), and [1,1'-bis(di-tert-butylphosphino)ferrocene]dichloropalladium(II) (130 mg, 0.20 mmol) was charged dioxane (10 mL), followed by a 2.0 M aqueous solution of sodium carbonate (0.99 mL, 2.0 mmol). The reaction mixture was degassed and heated to 75° C. for 2 hours. It was cooled to room temperature and charged with water (30 mL). The aqueous layer was extracted with ethyl acetate (50 mL×2), and the combined organic extracts were washed with brine (20 mL), dried (magnesium sulfate), filtered, and concentrated in vacuo. Purification by column chromatography over silica gel, eluting with dichloromethane/ethyl acetate, afforded the title compound. LC/MS=393 [M+1]. $^1$H-NMR (CDCl$_3$, 400 MHz) δ 8.94 (d, J=3.9 Hz, 1H), 8.63 (ddd, J=1.1, 1.6, 4.7 Hz, 1H), 8.20 (s, 1H), 8.15 (d, J=8.4 Hz, 1H), 7.79 (ddd, J=1.1, 1.6, 7.8 Hz, 1H), 7.73 (d, J=8.4 Hz, 1H), 7.55 (td, J=1.3, 8.4 Hz, 1H), 7.43 (ddd, J=0.9, 4.2, 8.2 Hz, 1H), 7.40 (s, 1H), 7.32 (ddd, J=1.0, 4.7, 7.8 Hz, 1H), 6.96 (d, J=8.6 Hz, 2H), 6.86 (s, 1H), 6.71 (d, J=8.0 Hz, 2H), 5.05 (s, 2H), 3.77 (d, J=0.9 Hz, 3H).

Step 3: 7-(3-(1H-pyrazol-4-yl)pyridin-2-yl)quinoline

To 7-(3-(1-(4-methoxybenzyl)-1H-pyrazol-4-yl)pyridin-2-yl)quinoline (665 mg, 1.69 mmol) was charged with trifluoroacetic acid (10 mL), and the reaction mixture was heated to 65° C. for 5 hours. Solvent was removed in vacuo, and the residue was charged with saturated aqueous sodium hydrogencarbonate solution (50 mL). The aqueous layer was extracted with dichloromethane (50 mL×2), and the combined organic extracts were dried (magnesium sulfate), filtered, and concentrated in vacuo. Purification by column chromatography over silica gel, eluting with dichloromethane/ethyl acetate, afforded the title compound. LC/MS=273 [M+1]. $^1$H-NMR (CDCl$_3$, 400 MHz) δ 8.92 (dd, J=1.7, 4.2 Hz, 1H), 8.68 (dd, J=1.7, 4.8 Hz, 1H), 8.22 (s, 1H), 8.18 (d, J=7.9 Hz, 1H), 7.84 (dd, J=1.7, 7.8 Hz, 1H), 7.82 (d, J=8.5 Hz, 1H), 7.63 (dd, J=1.7, 8.4 Hz, 1H), 7.42 (dd, J=4.3, 8.3 Hz, 1H), 7.33-7.40 (m, 3H).

Example 1

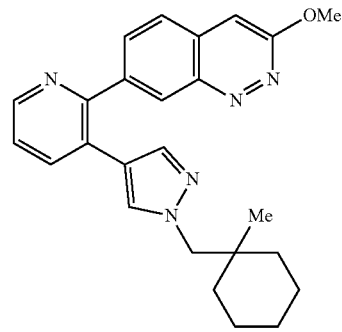 [SMILES: COc1cc2ccc(-c3ncccc3-c3cnn(CC4(C)CCCCC4)c3)cc2nn1]

3-methoxy-7-(3-{1-[(1-methylcyclohexyl)methyl]-1H-pyrazol-4-yl}pyridin-2-yl)cinnoline Step 1: (1-methylcyclohexyl)methyl 4-methylbenzenesulfonate To a pyridine (15 mL) solution of (1-methylcyclohexyl)methanol (1.00 g, 7.80 mmol) was added p-toluenesulfonyl chloride (1.49 g, 7.80 mmol). The reaction mixture was stirred at room temperature for 2 hours. Solvent was removed in vacuo, and the residue was charged with water (10 mL). The mixture was extracted with dichloromethane (25 mL×2), and the combined organic extracts were dried (magnesium sulfate), filtered and concentrated in vacuo to afford the crude product. Purification by column chromatography over silica gel, eluting with dichloromethane, afforded the title compound. $^1$H-NMR (CDCl$_3$, 400 MHz) δ 7.78 (d, J=8.1 Hz, 2H), 7.34 (d, J=8.1 Hz, 2H), 3.73 (s, 2H), 2.45 (s, 3H), 1.15-1.50 (m, 10H), 0.89 (s, 3H).

Step 2: 2-chloro-3-(1-((1-methylcyclohexyl)methyl)-1H-pyrazol-4-yl)pyridine

To a N,N-dimethylformamide solution (10 mL) of (1-methylcyclohexyl)methyl 4-methylbenzenesulfonate (1260 mg, 4.45 mmol) and 2-chloro-3-(1H-pyrazol-4-yl)pyridine (intermediate B1, 800 mg, 4.45 mmol) under nitrogen was added sodium hydride (60 wt %, 249 mg, 6.24 mmol). The reaction mixture was stirred at 70° C. for 7 hours and 80° C. for 24 hours. Water (40 mL) was added, and the reaction mixture was extracted with ethyl acetate (40 mL×2). The combined organic extracts were washed with water (40 mL), dried (magnesium sulfate), filtered and concentrated in vacuo to afford the crude product. Purification by column chromatography over silica gel, eluting with hexanes/ethyl acetate, afforded the title compound. LC/MS=290 [M+1]. $^1$H-NMR (CDCl$_3$, 400 MHz) δ 8.28 (dd, J=1.6, 4.6 Hz, 1H), 7.86 (s, 1H), 7.82 (d, J=1.7 Hz, 1H), 7.78 (s, 1H), 7.1-7.2 (m, 1H), 4.01 (s, 2H), 1.2-1.7 (m, 10H), 0.96 (s, 3H).

Step 3: 3-methoxy-7-(3-{1-[(1-methylcyclohexyl)methyl]-1H-pyrazol-4-yl}pyridin-2-yl)cinnoline To a tetrahydrofuran solution (0.43 mL) of 2-chloro-3-(1-((1-methylcyclohexyl)methyl)-1H-pyrazol-4-yl)pyridine (25 mg, 0.086 mmol) was added 3-methoxy-7-(4,4,5,5-tetramethyl-1,3,2-dioxaborolan-2-yl)cinnoline (intermediate D1, 25 mg, 0.087 mmol), [1,1'-bis(di-tert-butylphosphino)ferrocene]dichloropalladium(II) (2.8 mg, 4.3 µmol) and 1 M potassium phosphate solution in water (260 µL, 0.26 mmol). The reaction mixture was stirred at 120° C. for 12 hours. It was concentrated in vacuo, and the residue was purified by reverse phase HPLC (acetonitrile/water with 0.05% trifluoroacetic acid) to afford the title compound as the trifluoroacetate salt. LC/MS=414 [M+1]. $^1$H-NMR (DMSO-$d_6$, 500 MHz) δ 8.63 (d, J=4.7 Hz, 1H), 8.29 (s, 1H), 7.97 (d, J=7.8 Hz, 1H), 7.87 (d, J=8.7 Hz, 1H), 7.68-7.70 (m, 2H), 7.51 (dd, J=4.7, 7.9 Hz, 1H), 7.45 (s, 1H), 7.29 (s, 1H), 4.18 (s, 3H), 3.78 (s, 2H), 1.0-1.3 (m, 10H), 0.63 (s, 3H).

Example 2

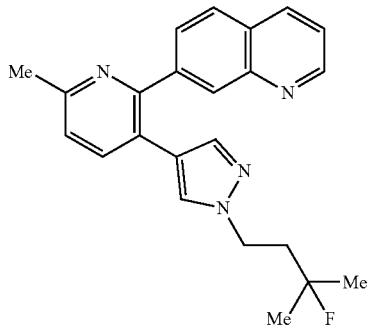

7-(3-(1-(3-fluoro-3-methylbutyl)-1H-pyrazol-4-yl)-6-methylpyridin-2-yl)quinoline Step 1: 3-fluoro-3-methylbutyl 4-methylbenzenesulfonate To a dichloromethane (5 mL) solution of 3-fluoro-3-methylbutan-1-ol (INTERMEDIATE C1, 0.594 g, 5.60 mmol) was added pyridine (1.36 mL, 16.8 mmol) and p-toluenesulfonyl chloride (1.60 g, 8.39 mmol). The reaction mixture was stirred at room temperature for 2 hours. Solvent was removed in vacuo, and the residue was charged with water (20 mL). The mixture was extracted with dichloromethane (20 mL×2), and the combined organic extracts were dried (magnesium sulfate), filtered and concentrated in vacuo to afford the crude product. Purification by column chromatography over silica gel, eluting with dichloromethane/hexanes, afforded the title compound. $^1$H-NMR (CDCl$_3$, 400 MHz) δ 7.79 (d, J=8.3 Hz, 2H), 7.36 (d, J=8.0 Hz, 2H), 4.18 (t, J=6.9 Hz, 2H), 2.46 (s, 3H), 2.01 (td, J=6.9, 19.6 Hz, 2H), 1.34 (d, J=21.5 Hz, 6H).

Step 2: 2-chloro-3-(1-(3-fluoro-3-methylbutyl)-1H-pyrazol-4-yl)-6-methylpyridine The title compound was made by following the procedures described in Step 2 for EXAMPLE 1, substituting 3-fluoro-3-methylbutyl 4-methylbenzenesulfonate for (1-methylcyclohexyl)methyl 4-methylbenzenesulfonate and 2-chloro-6-methyl-3-(1H-pyrazol-4-yl)pyridine (INTERMEDIATE B2) for 2-chloro-3-(1H-pyrazol-4-yl)pyridine. LC/MS=282 [M+1]. $^1$H-NMR (CDCl$_3$, 400 MHz) δ 7.88 (s, 1H), 7.80 (s, 1H), 7.67 (d, J=7.8 Hz, 1H), 7.11 (d, J=7.8 Hz, 1H), 4.34 (t, J=7.9 Hz, 2H), 2.55 (s, 3H), 2.28 (td, J=6.9, 19.8 Hz, 2H), 1.42 (d, J=21.4 Hz, 6H).

Step 3: 7-(3-(1-(3-fluoro-3-methylbutyl)-1H-pyrazol-4-yl)-6-methylpyridin-2-yl)quinoline The title compound was made by following the procedures described in Step 3 for EXAMPLE 1, substituting 2-chloro-3-(1-(3-fluoro-3-methylbutyl)-1H-pyrazol-4-yl)-6-methylpyridine for 2-chloro-3-(1-((1-methylcyclohexyl)methyl)-1H-pyrazol-4-yl)pyridine and 7-(4,4,5,5-tetramethyl-1,3,2-dioxaborolan-2-yl)quinoline for 3-methoxy-7-(4,4,5,5-tetramethyl-1,3,2-dioxaborolan-2-yl)cinnoline. LC/MS=375 [M+1]. $^1$H-NMR (DMSO-$d_6$, 500 MHz) δ 8.90 (d, J=2.5 Hz, 1H), 8.39 (d, J=8.4 Hz, 1H), 8.00 (s, 1H), 7.94 (d, J=8.4 Hz, 1H), 7.81 (d, J=8.0 Hz, 1H), 7.47-7.66 (m, 3H), 7.33 (d, J=8.0 Hz, 1H), 7.10 (s, 1H), 4.08 (t, J=7.6 Hz, 2H), 2.54 (s, 3H), 1.99 (td, J=7.6, 19.1 Hz, 2H), 1.21 (d, J=21.7 Hz, 6H).

The following examples in Table 1 were prepared using the procedures outlined in the synthesis of Example 2, with the appropriate electrophile in step 2 and the appropriate boronic acid or boronate ester in stem 5.

TABLE 1

| Ex | Structure | Name | MS (M + 1) |
|---|---|---|---|
| 3 | 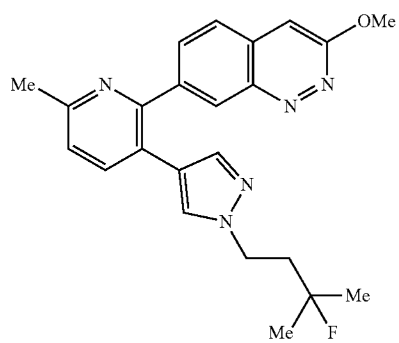 [SMILES: COc1cc2ccc(-c3nc(C)ccc3-c3cnn(CCC(C)(C)F)c3)cc2nn1] | 7-{3-[1-(3-fluoro-3-methylbutyl)-1H-pyrazol-4-yl]-6-methylpyridin-2-yl}-3-methoxycinnoline | 406 |

TABLE 1-continued

| Ex | Structure | Name | MS (M + 1) |
|---|---|---|---|
| 4 | 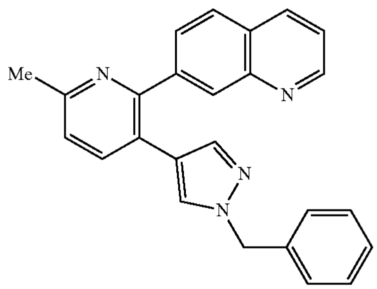 [SMILES: Cc1ccc(-c2cnn(Cc3ccccc3)c2)c(-c2ccc3cccnc3c2)n1] | 7-[3-(1-benzyl-1H-pyrazol-4-yl)-6-methylpyridin-2-yl]quinoline | 377 |
| 5 | 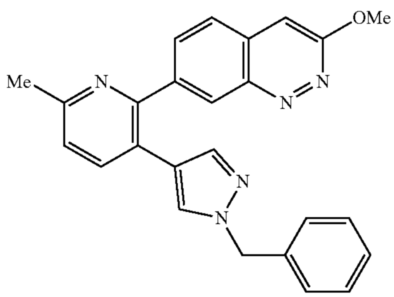 [SMILES: COc1cc2ccc(-c3nc(C)ccc3-c3cnn(Cc4ccccc4)c3)cc2nn1] | 7-[3-(1-benzyl-1H-pyrazol-4-yl)-6-methylpyridin-2-yl]-3-methoxycinnoline | 408 |
| 6 | 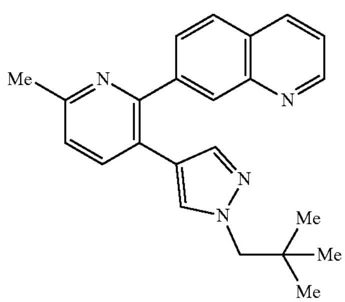 [SMILES: Cc1ccc(-c2cnn(CC(C)(C)C)c2)c(-c2ccc3cccnc3c2)n1] | 7-{3-[1-(2,2-dimethylpropyl)-1H-pyrazol-4-yl]-6-methylpyridin-2-yl}quinoline | 357 |
| 7 | 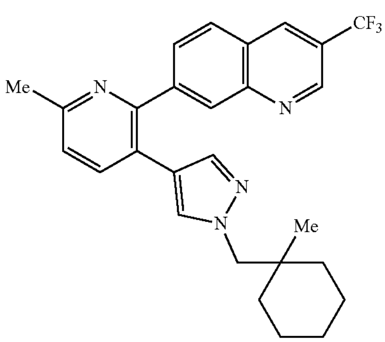 [SMILES: Cc1ccc(-c2cnn(CC3(C)CCCCC3)c2)c(-c2ccc3cc(C(F)(F)F)cnc3c2)n1] | 7-(6-methyl-3-{1-[(1-methylcyclohexyl)methyl]-1H-pyrazol-4-yl}pyridin-2-yl)-3-(trifluoromethyl)quinoline | 465 |
| 8 | 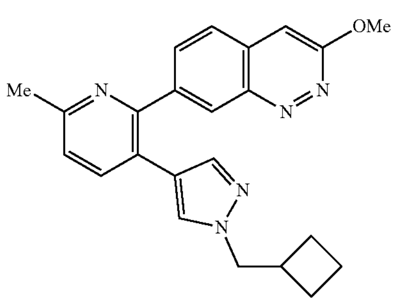 [SMILES: COc1cc2ccc(-c3nc(C)ccc3-c3cnn(CC4CCC4)c3)cc2nn1] | 7-{3-[1-(cyclobutylmethyl)-1H-pyrazol-4-yl]-6-methylpyridin-2-yl}-3-methoxycinnoline | 386 |

TABLE 1-continued

| Ex | Structure | Name | MS (M + 1) |
|---|---|---|---|
| 9 | 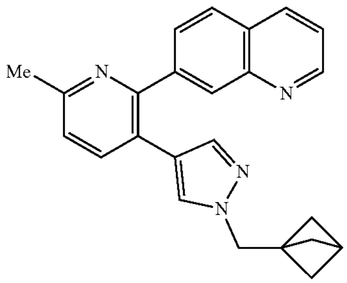 [SMILES: Cc1ccc(-c2cnn(CC34CC(C3)C4)c2)c(-c2ccc3cccnc3c2)n1] | 7-{3-[1-(bicyclo[1.1.1]pent-1-ylmethyl)-1H-pyrazol-4-yl]-6-methylpyridin-2-yl}quinoline | 367 |
| 10 | 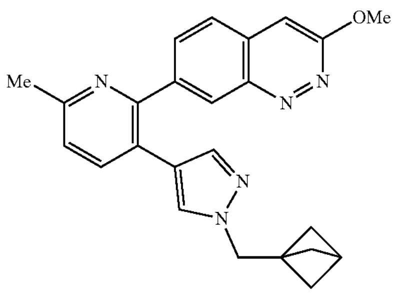 [SMILES: COc1cc2ccc(-c3nc(C)ccc3-c3cnn(CC45CC(C4)C5)c3)cc2nn1] | 7-{3-[1-(bicyclo[1.1.1]pent-1-ylmethyl)-1H-pyrazol-4-yl]-6-methylpyridin-2-yl}-3-methoxycinnoline | 398 |
| 11 | 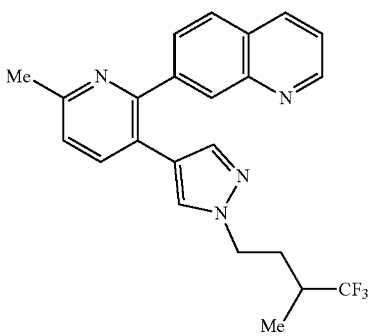 [SMILES: Cc1ccc(-c2cnn(CCC(C)C(F)(F)F)c2)c(-c2ccc3cccnc3c2)n1] | 7-{6-methyl-3-[1-(4,4,4-trifluoro-3-methylbutyl)-1H-pyrazol-4-yl]pyridin-2-yl}quinoline | 411 |
| 12 | 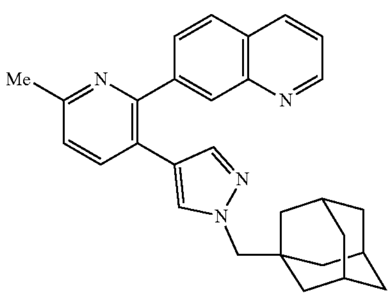 [SMILES: Cc1ccc(-c2cnn(CC34CC5CC(CC(C5)C3)C4)c2)c(-c2ccc3cccnc3c2)n1] | 7-(3-(1-(((3r,5r,7r)-adamantan-1-yl)methyl)-1H-pyrazol-4-yl)-6-methylpyridin-2-yl)quinoline | 435 |
| 13 | 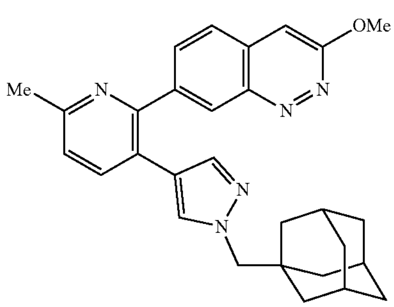 [SMILES: COc1cc2ccc(-c3nc(C)ccc3-c3cnn(CC45CC6CC(CC(C6)C4)C5)c3)cc2nn1] | 7-(3-(1-(((3r,5r,7r)-adamantan-1-yl)methyl)-1H-pyrazol-4-yl)-6-methylpyridin-2-yl)-3-methoxycinnoline | 466 |

TABLE 1-continued

| Ex | Structure | Name | MS (M + 1) |
|---|---|---|---|
| 14 | 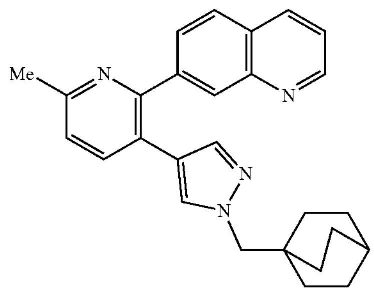 [SMILES: Cc1ccc(-c2cnn(CC34CCC(CC3)CC4)c2)c(-c2ccc3cccnc3c2)n1] | 7-{3-[1-(bicyclo[2.2.2]oct-1-ylmethyl)-1H-pyrazol-4-yl]-6-methylpyridin-2-yl}quinoline | 409 |
| 15 | 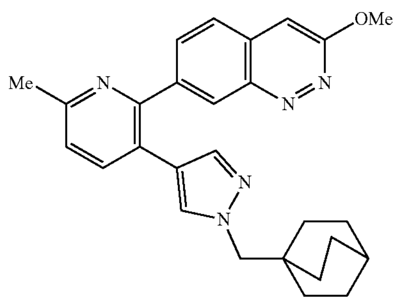 [SMILES: COc1cc2ccc(-c3nc(C)ccc3-c3cnn(CC45CCC(CC4)CC5)c3)cc2nn1] | 7-{3-[1-(bicyclo[2.2.2]oct-1-ylmethyl)-1H-pyrazol-4-yl]-6-methylpyridin-2-yl}-3-methoxycinnoline | 440 |
| 16 | 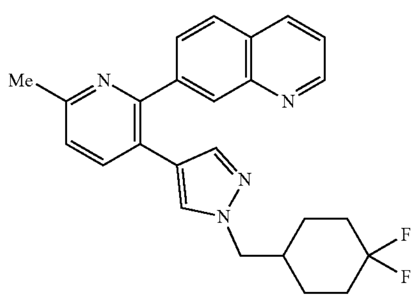 [SMILES: Cc1ccc(-c2cnn(CC3CCC(F)(F)CC3)c2)c(-c2ccc3cccnc3c2)n1] | 7-(3-{1-[(4,4-difluorocyclohexyl)methyl]-1H-pyrazol-4-yl}-6-methylpyridin-2-yl)quinoline | 419 |
| 17 | 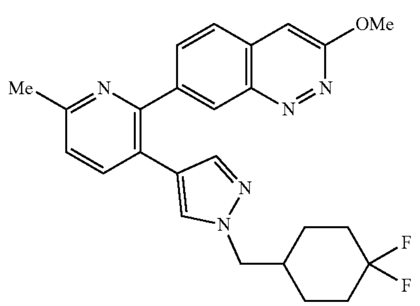 [SMILES: COc1cc2ccc(-c3nc(C)ccc3-c3cnn(CC4CCC(F)(F)CC4)c3)cc2nn1] | 7-(3-{1-[(4,4-difluorocyclohexyl)methyl]-1H-pyrazol-4-yl}-6-methylpyridin-2-yl)-3-methoxycinnoline | 450 |
| 18 | 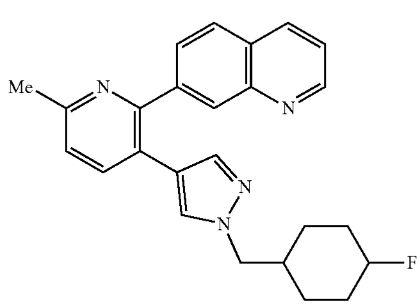 [SMILES: Cc1ccc(-c2cnn(CC3CCC(F)CC3)c2)c(-c2ccc3cccnc3c2)n1] | 7-(3-{1-[(4-fluorocyclohexyl)methyl]-1H-pyrazol-4-yl}-6-methylpyridin-2-yl)quinoline | 401 |

TABLE 1-continued

| Ex | Structure | Name | MS (M + 1) |
|----|-----------|------|------------|
| 19 | 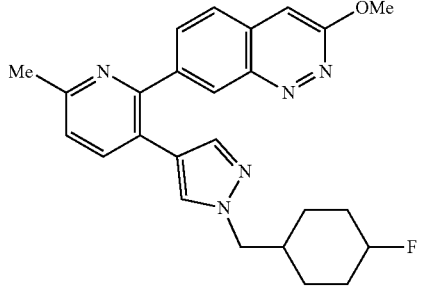 [SMILES: COc1cc2ccc(-c3nc(C)ccc3-c3cnn(CC4CCC(F)CC4)c3)cc2nn1] | 7-(3-{1-[(4-fluorocyclohexyl)methyl]-1H-pyrazol-4-yl}-6-methylpyridin-2-yl)-3-methoxycinnoline | 432 |
| 20 | 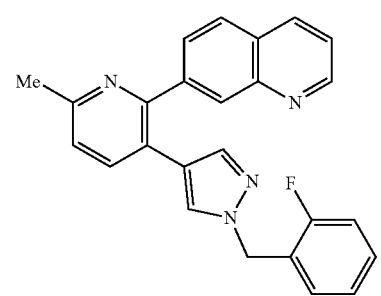 [SMILES: Cc1ccc(-c2cnn(Cc3ccccc3F)c2)c(-c2ccc3cccnc3c2)n1] | 7-{3-[1-(2-fluorobenzyl)-1H-pyrazol-4-yl]-6-methylpyridin-2-yl}quinoline | 395 |
| 21 | 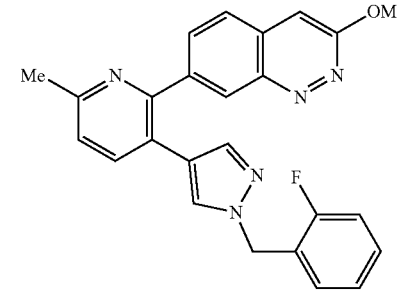 | 7-{3-[1-(2-fluorobenzyl)-1H-pyrazol-4-yl]-6-methylpyridin-2-yl}-3-methoxycinnoline | 426 |
| 22 | 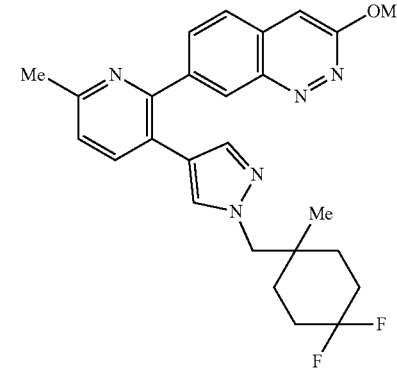 | 7-(3-{1-[(4,4-difluoro-1-methylcyclohexyl)methyl]-1H-pyrazol-4-yl}-6-methylpyridin-2-yl)-3-methoxycinnoline | 464 |
| 23 | 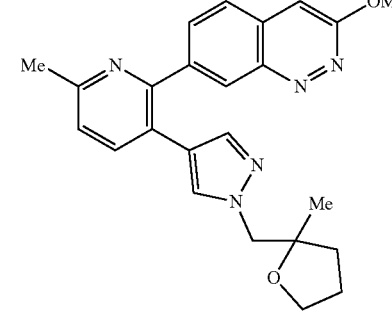 | 3-methoxy-7-(6-methyl-3-{1-[(2-methyltetrahydrofuran-2-yl)methyl]-1H-pyrazol-4-yl}pyridin-2-yl)cinnoline | 416 |

TABLE 1-continued

| Ex | Structure | Name | MS (M + 1) |
|---|---|---|---|
| 24 | 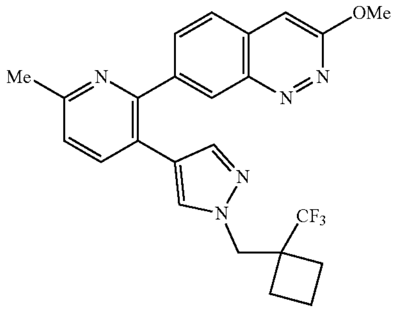 [SMILES: COc1cc2ccc(-c3nc(C)ccc3-c3cnn(CC4(C(F)(F)F)CCC4)c3)cc2nn1] | 3-methoxy-7-[6-methyl-3-(1-{[1-(trifluoromethyl)cyclobutyl]methyl}-1H-pyrazol-4-yl)pyridin-2-yl]cinnoline | 454 |
| 25 | 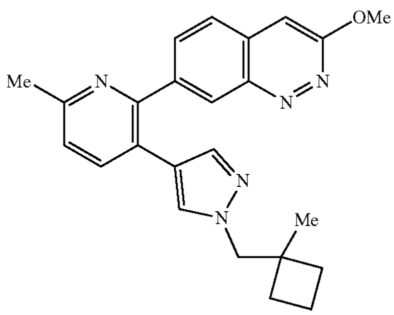 [SMILES: COc1cc2ccc(-c3nc(C)ccc3-c3cnn(CC4(C)CCC4)c3)cc2nn1] | 3-methoxy-7-(6-methyl-3-{1-[(1-methylcyclobutyl)methyl]-1H-pyrazol-4-yl}pyridin-2-yl)cinnoline | 400 |

Example 26

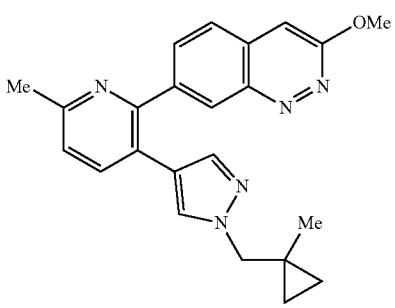 [SMILES: COc1cc2ccc(-c3nc(C)ccc3-c3cnn(CC4(C)CC4)c3)cc2nn1]

3-methoxy-7-(6-methyl-3-{1-[(1-methylcyclopropyl)methyl]-1H-pyrazol-4-yl}pyridin-2-yl)cinnoline

Step 1: 2-chloro-6-methyl-3-(1-((1-methylcyclopropyl)methyl)-1H-pyrazol-4-yl)pyridine To a toluene (10 mL) mixture of 2-chloro-6-methyl-3-(1H-pyrazol-4-yl)pyridine (INTERMEDIATE B2, 200 mg, 1.03 mmol), triphenylphosphine (542 mg, 2.07 mmol), and (1-methylcyclopropyl)methanol (178 mg, 2.07 mmol) at 0° C. was added diisopropyl azodicarboxylate (0.402 mL, 2.07 mmol). The reaction mixture was then warmed up to room temperature, stirred for 20 hours, and concentrated in vacuo to afford the crude product. Purification by column chromatography over silica gel, eluting with ethyl acetate/hexanes, afforded the title compound. LC/MS=262 [M+1].

Step 2: 3-methoxy-7-(6-methyl-3-{1-[(1-methylcyclopropyl)methyl]-1H-pyrazol-4-yl}pyridin-2-yl)cinnoline The title compound was made by following the procedures described in Step 3 for EXAMPLE 1, substituting 2-chloro-6-methyl-3-(1-((1-methylcyclopropyl)methyl)-1H-pyrazol-4-yl)pyridine for 2-chloro-3-(1-((1-methylcyclohexyl)methyl)-1H-pyrazol-4-yl)pyridine. LC/MS=386 [M+1]. $^1$H-NMR (CDCl$_3$, 400 MHz) δ 8.54 (s, 1H), 7.72 (d, J=7.9 Hz, 1H), 7.61 (d, J=1.0 Hz, 2H), 7.38 (s, 1H), 7.24 (d, J=8.0 Hz, 1H), 7.22 (d, J=0.9 Hz, 1H), 7.02 (s, 1H), 4.30 (s, 3H), 3.78 (s, 2H), 2.66 (s, 3H), 0.82 (s, 3H), 0.37 (t, J=4.6 Hz, 2H), 0.24 (t, J=4.6 Hz, 2H).

The following examples in Table 2 were prepared using the procedures outlined in the synthesis of Example 26, with the appropriate alcohol and intermediate (B3 instead of B2) in step 1 and the appropriate boronic acid or boronate ester in step 2.

TABLE 2

| Ex | Structure | Name | MS (M + 1) |
|---|---|---|---|
| 27 | 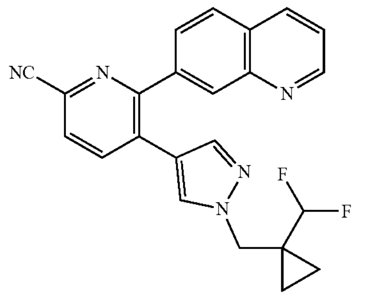 [SMILES: N#Cc1ccc(-c2cnn(CC3(C(F)F)CC3)c2)c(-c2ccc3cccnc3c2)n1] | 5-(1-{[1-(difluoromethyl)cyclopropyl]methyl}-1H-pyrazol-4-yl)-6-quinolin-7-ylpyridine-2-carbonitrile | 402 |
| 28 | 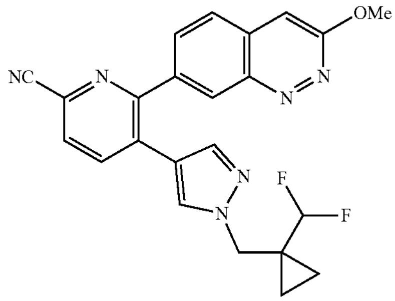 [SMILES: COc1cc2ccc(-c3nc(C#N)ccc3-c3cnn(CC4(C(F)F)CC4)c3)cc2nn1] | 5-(1-{[1-(difluoromethyl)cyclopropyl]methyl}-1H-pyrazol-4-yl)-6-(3-methoxycinnolin-7-yl)pyridine-2-carbonitrile | 433 |
| 29 | 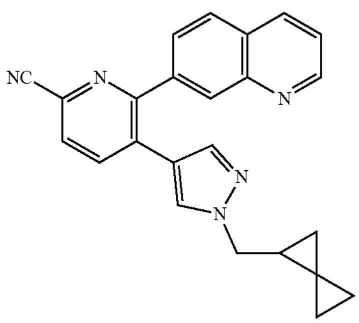 [SMILES: N#Cc1ccc(-c2cnn(CC3CC34CC4)c2)c(-c2ccc3cccnc3c2)n1] | 6-quinolin-7-yl-5-[1-(spiro[2.2]pent-1-ylmethyl)-1H-pyrazol-4-yl]pyridine-2-carbonitrile | 378 |

Example 30

7-{6-chloro-3-[1-(3-methoxy-3-methylbutyl)-1H-pyrazol-4-yl]-5-methylpyridin-2-yl}-3-methoxycinnoline

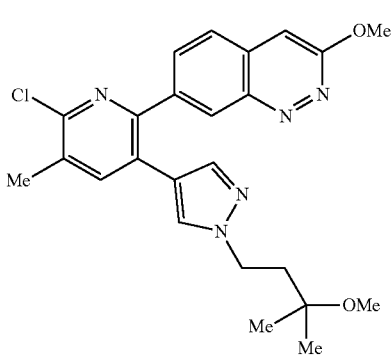

Step 1: 3-methoxy-3-methylbutyl 4-methylbenzenesulfonate

To a dichloromethane (80 mL) solution of 3-methoxy-3-methylbutan-1-ol (3000 mg, 25.4 mmol) and triethylamine (7700 mg, 76 mmol) was charged p-toluenesulfonyl chloride (5.32 g, 27.9 mmol). The reaction mixture was stirred at room temperature for 18 hours, and another batch of p-toluenesulfonyl chloride (2.00 g, 10.5 mmol) was added. The reaction mixture was stirred at room temperature for another 3 hours. Water (50 mL) was then added to the reaction mixture, which was extracted with dichloromethane (20 mL×3). The combined organic extracts were dried (sodium sulfate), filtered, and concentrated in vacuo to afford the crude product. Purification by column chromatography over silica gel, eluting with ethyl acetate/petroleum ether, afforded the title compound. $^1$H-NMR (CDCl$_3$, 400 MHz) δ 7.77 (d, J=8.4 Hz, 2H), 7.32 (d, J=8.8 Hz, 2H), 4.10 (t, J=7.4 Hz, 2H), 3.08 (s, 3H), 2.43 (s, 3H), 1.85 (t, J=7.4 Hz, 2H), 1.10 (s, 6H).

Step 2: 2-bromo-6-chloro-3-(1-(3-methoxy-3-methylbutyl)-1H-pyrazol-4-yl)-5-methylpyridine To a round-bottom flask containing a mixture of the hydrochloride salt of 2-bromo-6-chloro-5-methyl-3-(1H-pyrazol-4-yl)pyridine (INTERMEDIATE B4, 220 mg, 0.712 mmol) and cesium carbonate (696 mg, 2.14 mmol) was charged N,N-dimethylformamide (6.0 mL), followed by 3-methoxy-3-methylbutyl 4-methylbenzenesulfonate (233 mg, 0.854 mmol). The reaction mixture was stirred at 70° C. for 1.5 hours. Water (15 mL) was added to the reaction mixture, which was extracted with ethyl acetate (10 mL×3). The combined organic extracts were washed with brine (10 mL×2), dried (sodium sulfate), filtered, and concentrated in vacuo to afford the crude product. Purification by column chromatography over silica gel, eluting with ethyl acetate/petroleum ether, afforded the title compound. LC/MS=374 [M+1]. $^1$H-NMR (CDCl$_3$, 400 MHz) δ 7.87 (s, 1H), 7.75 (s, 1H), 7.54 (s, 1H), 4.25 (t, J=7.8 Hz, 2H), 3.22 (s, 3H), 2.35 (s, 3H), 2.12 (t, J=8.2 Hz, 2H), 1.22 (s, 6H).

Step 3: 7-{6-chloro-3-[1-(3-methoxy-3-methylbutyl)-1H-pyrazol-4-yl]-5-methylpyridin-2-yl}-3-methoxycinnoline To a Schlenk tube containing 2-bromo-6-chloro-3-(1-(3-methoxy-3-methylbutyl)-1H-pyrazol-4-yl)-5-methylpyridine (40 mg, 0.107 mmol), potassium phosphate (68.3 mg, 0.322 mmol), 3-methoxy-7-(4,4,5,5-tetramethyl-1,3,2-dioxaborolan-2-yl)cinnoline (30.7 mg, 0.107 mmol), and [1,1'-bis(di-tert-butylphosphino)ferrocene]dichloropalladium(II) (7.0 mg, 11 µmol) was added tetrahydrofuran (3.0 mL) and water (1.0 mL). The reaction mixture was stirred at room temperature for 18 hours, filtered, and concentrated in vacuo to afford the crude product. Purification by reverse phase HPLC (acetonitrile/water with 0.05% trifluoroacetic acid) afforded the title compound as the trifluoroacetate salt. LC/MS=452 [M+1]. $^1$H-NMR (CD$_3$OD, 400 MHz) δ 8.31 (s, 1H), 7.82-7.92 (m, 2H), 7.62-7.75 (m, 2H), 7.51 (s, 1H), 7.28 (s, 1H), 4.23 (s, 3H), 4.10 (t, J=8.0 Hz, 2H), 3.08 (s, 3H), 2.47 (s, 3H), 1.85 (t, J=8.0 Hz, 2H), 1.09 (s, 6H).

Example 31

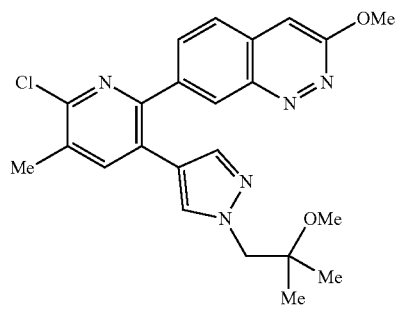 [SMILES: COc1cc2ccc(-c3nc(Cl)c(C)cc3-c3cnn(CC(C)(C)OC)c3)cc2nn1]

7-{6-chloro-3-[1-(2-methoxy-2-methylpropyl)-1H-pyrazol-4-yl]-5-methylpyridin-2-yl}-3-methoxycinnoline

Step 1: 1-(4-(2-bromo-6-chloro-5-methylpyridin-3-yl)-1H-pyrazol-1-yl)-2-methylpropan-2-ol To a round-bottom flask containing 2-bromo-6-chloro-5-methyl-3-(1H-pyrazol-4-yl)pyridine (INTERMEDIATE B4, 240 mg, 0.88 mmol) and cesium carbonate (861 mg, 2.64 mmol) was added acetonitrile (2.0 mL), followed by 2,2-dimethyloxirane (2.36 mL, 26.4 mmol). The reaction mixture was stirred at 80° C. for 2 hours. Water (10 mL) was added to the reaction mixture, which was extracted with ethyl acetate (10 mL×3). The combined organic extracts were dried (sodium sulfate), filtered, and concentrated in vacuo to afford the title compound as crude product. It was used in the subsequent reaction without further purification. LC/MS=346 [M+1]. $^1$H-NMR (CDCl$_3$, 400 MHz) δ 7.93 (s, 1H), 7.82 (s, 1H), 7.59 (s, 1H), 4.16 (s, 2H), 2.39 (s, 3H), 1.24 (s, 6H).

Step 2: 2-bromo-6-chloro-3-(1-(2-methoxy-2-methylpropyl)-1H-pyrazol-4-yl)-5-methylpyridine To a round bottom flask containing a tetrahydrofuran (10 mL) solution of 1-(4-(2-bromo-6-chloro-5-methylpyridin-3-yl)-1H-pyrazol-1-yl)-2-methylpropan-2-ol (360 mg, 1.045 mmol) were added sodium hydride (60 wt %, 41.8 mg, 1.045 mmol) and iodomethane (0.065 mL, 1.045 mmol). The reaction mixture was stirred at 26° C. for 2 hours, then quenched with water (10 mL) and extracted with ethyl acetate (6 mL×3). The combined organic layers were dried (sodium sulfate), filtered, and concentrated in vacuo to afford the crude product. Purification by column chromatography over silica gel, eluting with ethyl acetate/petroleum ether, afforded the title compound. $^1$H-NMR (CDCl$_3$, 400 MHz) δ 7.93 (s, 1H), 7.71 (s, 1H), 7.54 (s, 1H), 4.14 (s, 2H), 3.24 (s, 3H), 2.33 (s, 3H), 1.15 (s, 6H).

Step 3: 7-{6-chloro-3-[1-(2-methoxy-2-methylpropyl)-1H-pyrazol-4-yl]-5-methylpyridin-2-yl}-3-methoxycinnoline The title compound was made by following the procedures described in Step 3 for EXAMPLE 30, substituting 2-bromo-6-chloro-3-(1-(2-methoxy-2-methylpropyl)-1H-pyrazol-4-yl)-5-methylpyridine for 2-bromo-6-chloro-3-(1-(3-methoxy-3-methylbutyl)-1H-pyrazol-4-yl)-5-methylpyridine. LC/MS=438 [M+1]. $^1$H-NMR (CD$_3$OD, 400 MHz) δ 8.28 (s, 1H), 7.81-7.91 (m, 2H), 7.62-7.71 (m, 2H), 7.39 (s, 1H), 7.30 (s, 1H), 4.22 (s, 3H), 3.97 (s, 2H), 2.88 (s, 3H), 2.45 (s, 3H), 0.96 (s, 6H).

Example 32

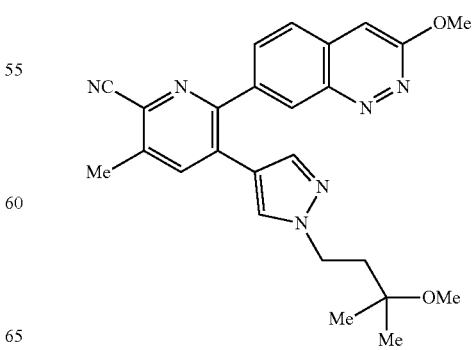

6-(3-methoxycinnolin-7-yl)-5-[1-(3-methoxy-3-methylbutyl)-1H-pyrazol-4-yl]-3-methylpyridine-2-carbonitrile In a microwave reaction vial, a mixture of 7-{6-chloro-3-[1-(3-methoxy-3-methylbutyl)-1H-pyrazol-4-yl]-5-methylpyridin-2-yl}-3-methoxycinnoline (EXAMPLE 30, 40 mg, 0.089 mmol), zinc (5.8 mg, 0.089 mmol), dicyanozinc (20.8 mg, 0.177 mmol) and bis(tri-tert-butylphosphine)palladium(0) (4.5 mg, 8.9 μmol) was charged with 1,4-dioxane (1.5 mL). The vial was capped and irradiated with microwaves at 140° C. for 25 minutes. The reaction mixture was diluted with ethyl acetate (5 mL), filtered through diatomaceous earth, and concentrated in vacuo to afford the crude product. Purification by reverse phase HPLC (acetonitrile/water with 0.05% trifluoroacetic acid) to afford the title compound as the trifluoroacetate salt. LC/MS=443 [M+1]. $^1$H-NMR (CD$_3$OD, 400 MHz) δ 8.32 (s, 1H), 8.02 (s, 1H), 7.88 (d, J=8.6 Hz, 1H), 7.70 (d, J=8.6 Hz, 1H), 7.65 (s, 1H), 7.56 (s, 1H), 7.32 (s, 1H), 4.23 (s, 3H), 4.05 (t, J=8.0 Hz, 2H), 3.08 (s, 3H), 2.61 (s, 3H), 1.85 (t, J=8.0 Hz, 2H), 1.09 (s, 6H).

Example 33

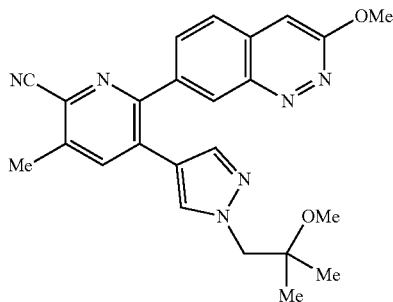

6-(3-methoxycinnolin-7-yl)-5-[1-(2-methoxy-2-methylpropyl)-1H-pyrazol-4-yl]-3-methylpyridine-2-carbonitrile The title compound was made by following the procedures described for EXAMPLE 32, substituting 7-{6-chloro-3-[1-(2-methoxy-2-methylpropyl)-1H-pyrazol-4-yl]-5-methylpyridin-2-yl}-3-methoxycinnoline (EXAMPLE 31) for 7-{6-chloro-3-[1-(3-methoxy-3-methylbutyl)-1H-pyrazol-4-yl]-5-methylpyridin-2-yl}-3-methoxycinnoline. LC/MS=429 [M+1]. $^1$H-NMR (CD$_3$OD, 400 MHz) δ 8.31 (s, 1H), 8.03 (s, 1H), 7.87 (d, J=8.8 Hz, 1H), 7.68 (d, J=8.4 Hz, 1H), 7.63 (s, 1H), 7.46 (s, 1H), 7.33 (s, 1H), 4.22 (s, 3H), 3.97 (s, 2H), 2.86 (s, 3H), 2.61 (s, 3H), 0.96 (s, 6H).

Example 34

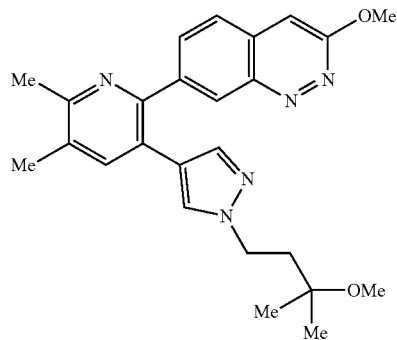 [SMILES: COc1cc2ccc(-c3nc(C#N)c(C)cc3-c3cnn(CCC(C)(C)OC)c3)cc2nn1]

3-methoxy-7-{3-[1-(3-methoxy-3-methylbutyl)-1H-pyrazol-4-yl]-5,6-dimethylpyridin-2-yl}cinnoline In a microwave reaction vial, a mixture of 7-{6-chloro-3-[1-(3-methoxy-3-methylbutyl)-1H-pyrazol-4-yl]-5-methylpyridin-2-yl}-3-methoxycinnoline (EXAMPLE 30, 20 mg, 0.044 mmol), tetrakis(triphenylphosphine)palladium(0) (5.1 mg, 4.4 μmol) and tetramethylstannane (31.7 mg, 0.177 mmol) was charged with N,N-dimethylformamide (1.5 mL). The vial was capped and irradiated with microwaves at 140° C. for 60 minutes. The reaction mixture was diluted with ethyl acetate (5 mL), filtered through diatomaceous earth, and concentrated in vacuo to afford the crude product. Purification by reverse phase HPLC (acetonitrile/water with 0.05% trifluoroacetic acid) to afford the title compound as the trifluoroacetate salt. LC/MS=432 [M+1]. $^1$H-NMR (CD$_3$OD, 400 MHz) δ 8.42 (s, 1H), 8.08 (s, 1H), 7.91 (d, J=8.4 Hz, 1H), 7.59-7.67 (m, 2H), 7.49 (s, 1H), 7.25 (s, 1H), 4.25 (s, 3H), 4.05 (t, J=8.0 Hz, 2H), 3.07 (s, 3H), 2.66 (s, 3H), 2.48 (s, 3H), 1.85 (t, J=8.0 Hz, 2H), 1.07 (s, 6H).

Example 35

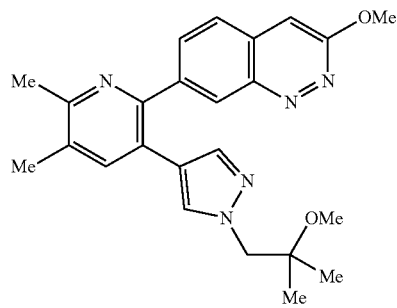 [SMILES: COc1cc2ccc(-c3nc(C)c(C)cc3-c3cnn(CC(C)(C)OC)c3)cc2nn1]

3-methoxy-7-{3-[1-(2-methoxy-2-methylpropyl)-1H-pyrazol-4-yl]-5,6-dimethylpyridin-2-yl}cinnoline The title compound was made by following the procedures described for EXAMPLE 34, substituting 7-{6-chloro-3-[1-(2-methoxy-2-methylpropyl)-1H-pyrazol-4-yl]-5-methylpyridin-2-yl}-3-methoxycinnoline (EXAMPLE 31) for 7-{6-chloro-3-[1-(3-methoxy-3-methylbutyl)-1H-pyrazol-4-yl]-5-methylpyridin-2-yl}-3-methoxycinnoline.

LC/MS=418 [M+1]. $^1$H-NMR (CD$_3$OD, 400 MHz) δ 8.58 (s, 1H), 8.51 (s, 1H), 7.99 (d, J=8.4 Hz, 1H), 7.60-7.70 (m, 2H), 7.48 (s, 1H), 7.32 (s, 1H), 4.26 (s, 3H), 3.98 (s, 2H), 2.87 (s, 3H), 2.77 (s, 3H), 2.58 (s, 3H), 0.94 (s, 6H).

Example 36

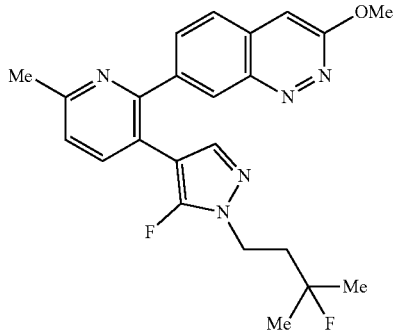 [SMILES: COc1cc2ccc(-c3nc(C)ccc3-c3cnn(CCC(C)(C)F)c3F)cc2nn1]

7-{3-[5-fluoro-1-(3-fluoro-3-methylbutyl)-1H-pyrazol-4-yl]-6-methylpyridin-2-yl}-3-methoxycinnoline Step 1: 2-chloro-3-(5-fluoro-1-(3-fluoro-3-methylbutyl)-1H-pyrazol-4-yl)-6-methylpyridine To an acetonitrile (6 mL) solution of 2-chloro-3-(1-(3-fluoro-3-methylbutyl)-1H-pyrazol-4-yl)-6-methylpyridine (EXAMPLE 2, step 2, 336 mg, 1.19 mmol) was added 1-chloromethyl-4-fluoro-1,4-diazoniabicyclo[2.2.2]octane bis(tetrafluoroborate) (633 mg, 1.79 mmol). The reaction mixture was stirred at 45° C. for 16 hours. Solvent was removed in vacuo to afford the crude product. Purification by column chromatography over silica gel, eluting with ethyl acetate/hexanes, afforded the title compound. LC/MS=300 [M+1].

Step 2: 7-{3-[5-fluoro-1-(3-fluoro-3-methylbutyl)-1H-pyrazol-4-yl]-6-methylpyridin-2-yl}-3-methoxycinnoline The title compound was made by following the procedures described in Step 3 for EXAMPLE 1, substituting 2-chloro-3-(5-fluoro-1-(3-fluoro-3-methylbutyl)-1H-pyrazol-4-yl)-6-methylpyridine for 2-chloro-3-(1-((1-methylcyclohexyl)methyl)-1H-pyrazol-4-yl)pyridine. LC/MS=424 [M+1]. $^1$H-NMR (DMSO-d$_6$, 500 MHz) δ 8.24 (s, 1H), 7.91 (d, J=8.7 Hz, 1H), 7.82 (d, J=7.9 Hz, 1H), 7.77 (d, J=8.7 Hz, 1H), 7.70 (s, 1H), 7.39-7.41 (m, 2H), 4.17 (s, 3H), 3.97 (t, J=7.5 Hz, 2H), 2.56 (s, 3H), 1.87 (td, J=7.7, 19.7 Hz, 2H), 1.20 (d, J=21.6 Hz, 6H).

Example 37

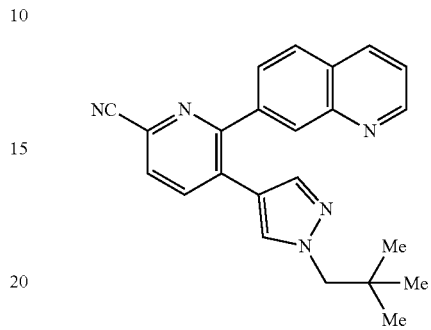

5-[1-(2,2-dimethylpropyl)-1H-pyrazol-4-yl]-6-quinolin-7-ylpyridine-2-carbonitrile To a 1,4-dioxane (4 mL)/water (1 mL) solution of 6-chloro-5-(1-neopentyl-1H-pyrazol-4-yl)picolinonitrile (INTERMEDIATE E8, 100 mg, 0.364 mmol) under nitrogen were added 7-(4,4,5,5-tetramethyl-1,3,2-dioxaborolan-2-yl)quinoline (111 mg, 0.437 mmol), [1,1'-bis(di-tert-butylphosphino)ferrocene]dichloropalladium(II) (5.3 mg, 7.3 μmol), and potassium phosphate trihydrate (242 mg, 0.910 mmol). The reaction mixture was stirred at 75° C. for 16 hours. Ethyl acetate (30 mL) and water (20 mL) were added to the reaction mixture. The organic layer was washed with brine (15 mL), dried (sodium sulfate), filtered, and concentrated in vacuo to afford the crude product. Purification by column chromatography over silica gel, eluting with petroleum ether/ethyl acetate, afforded the title compound. LC/MS=368 [M+1]. $^1$H-NMR (CD$_3$OD, 400 MHz) δ 8.85 (d, J=2.8 Hz, 1H), 8.40 (d, J=8.0 Hz, 1H), 8.15 (d, J=8.0 Hz, 1H), 8.08 (s, 1H), 7.99 (d, J=8.0 Hz, 1H), 7.90 (d, J=8.0 Hz, 1H), 7.58-7.65 (m, 2H), 7.40 (s, 1H), 7.22 (s, 1H), 3.73 (s, 2H), 0.68 (s, 9H).

The following examples in Table 3 were prepared using the procedures outlined in the synthesis of Example 37, with the appropriate INTERMEDIATE E and the appropriate boronic acid or boronate ester (INTERMEDIATE D).

TABLE 3

| Ex | Structure | Name | MS (M + 1) |
|---|---|---|---|
| 38 | 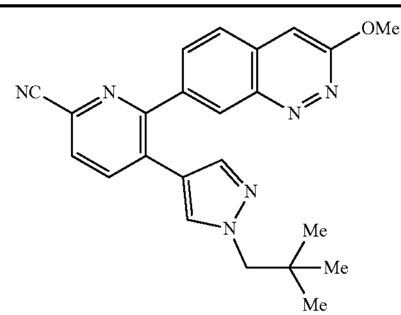 | 5-[1-(2,2-dimethylpropyl)-1H-pyrazol-4-yl]-6-(3-methoxycinnolin-7-yl)pyridine-2-carbonitrile | 399 |

TABLE 3-continued

| Ex | Structure | Name | MS (M + 1) |
|---|---|---|---|
| 39 | 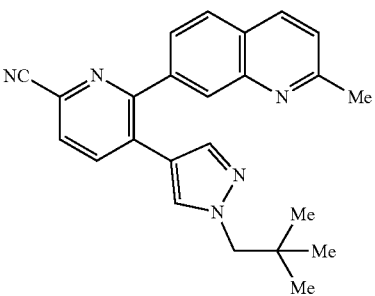 [SMILES: Cc1ccc2ccc(-c3nc(C#N)ccc3-c3cnn(CC(C)(C)C)c3)cc2n1] | 5-[1-(2,2-dimethylpropyl)-1H-pyrazol-4-yl]-6-(2-methylquinolin-7-yl)pyridine-2-carbonitrile | 382 |
| 40 | 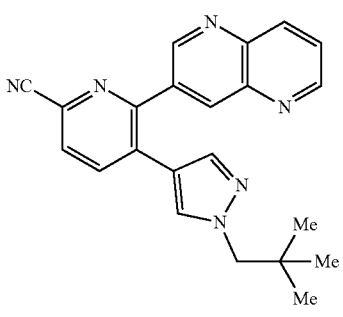 [SMILES: CC(C)(C)Cn1cc(-c2ccc(C#N)nc2-c2cnc3cccnc3c2)cn1] | 5-[1-(2,2-dimethylpropyl)-1H-pyrazol-4-yl]-6-(1,5-naphthyridin-3-yl)pyridine-2-carbonitrile | 369 |
| 41 | 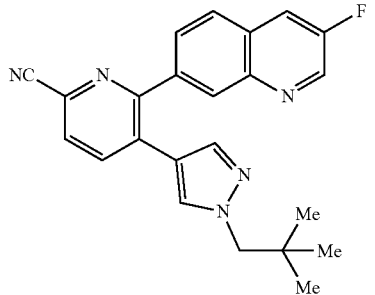 [SMILES: CC(C)(C)Cn1cc(-c2ccc(C#N)nc2-c2ccc3cc(F)cnc3c2)cn1] | 5-[1-(2,2-dimethylpropyl)-1H-pyrazol-4-yl]-6-(3-fluoroquinolin-7-yl)pyridine-2-carbonitrile | 386 |
| 42 | 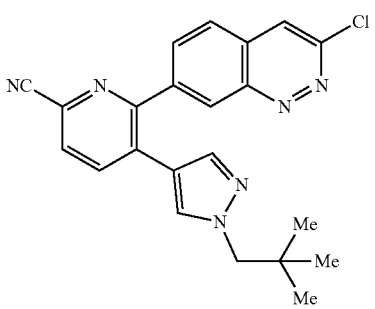 [SMILES: CC(C)(C)Cn1cc(-c2ccc(C#N)nc2-c2ccc3cc(Cl)nnc3c2)cn1] | 6-(3-chlorocinnolin-7-yl)-5-[1-(2,2-dimethylpropyl)-1H-pyrazol-4-yl]pyridine-2-carbonitrile | 403 |
| 43 | 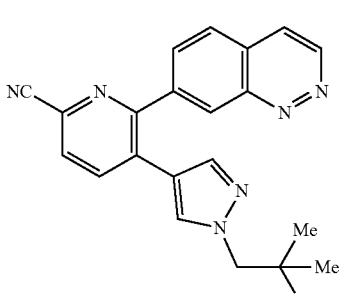 | 6-cinnolin-7-yl-5-[1-(2,2-dimethylpropyl)-1H-pyrazol-4-yl]pyridine-2-carbonitrile | 369 |

TABLE 3-continued

| Ex | Structure | Name | MS (M + 1) |
|---|---|---|---|
| 44 | 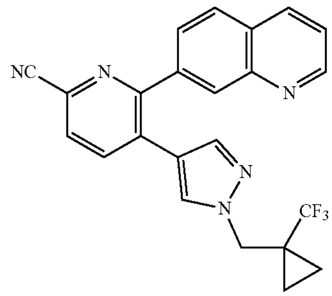 [SMILES: N#Cc1ccc(-c2cnn(CC3(C(F)(F)F)CC3)c2)c(-c2ccc3cccnc3c2)n1] | 6-quinolin-7-yl-5-(1-{[1-(trifluoromethyl)cyclopropyl]methyl}-1H-pyrazol-4-yl)pyridine-2-carbonitrile | 420 |
| 45 | 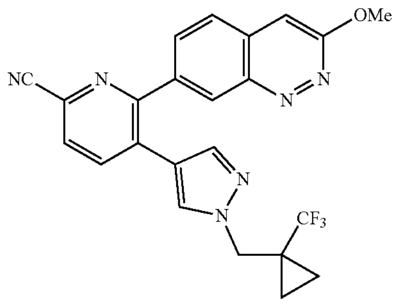 [SMILES: COc1cc2ccc(-c3nc(C#N)ccc3-c3cnn(CC4(C(F)(F)F)CC4)c3)cc2nn1] | 6-(3-methoxycinnolin-7-yl)-5-(1-{[1-(trifluoromethyl)cyclopropyl]methyl}-1H-pyrazol-4-yl)pyridine-2-carbonitrile | |
| 46 | 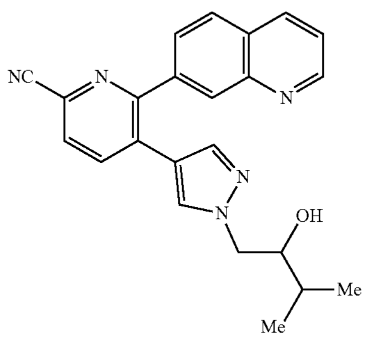 [SMILES: CC(C)C(O)Cn1cc(-c2ccc(C#N)nc2-c2ccc3cccnc3c2)cn1] | 5-[1-(2-hydroxy-3-methylbutyl)-1H-pyrazol-4-yl]-6-quinolin-7-ylpyridine-2-carbonitrile | 384 |
| 47 | 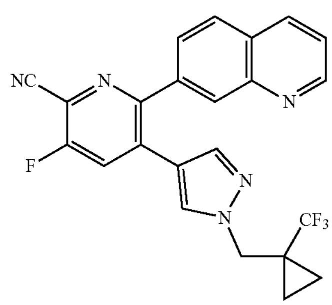 [SMILES: N#Cc1nc(-c2ccc3cccnc3c2)c(-c2cnn(CC3(C(F)(F)F)CC3)c2)cc1F] | 3-fluoro-6-quinolin-7-yl-5-(1-{[1-(trifluoromethyl)cyclopropyl]methyl}-1H-pyrazol-4-yl)pyridine-2-carbonitrile | 438 |
| 48 | 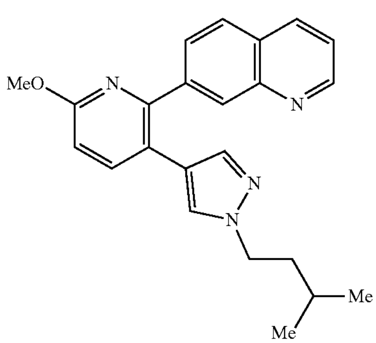 [SMILES: COc1ccc(-c2cnn(CCC(C)C)c2)c(-c2ccc3cccnc3c2)n1] | 7-{6-methoxy-3-[1-(3-methylbutyl)-1H-pyrazol-4-yl]pyridine-2-yl}quinoline | 373 |

TABLE 3-continued

| Ex | Structure | Name | MS (M + 1) |
|---|---|---|---|
| 49 | 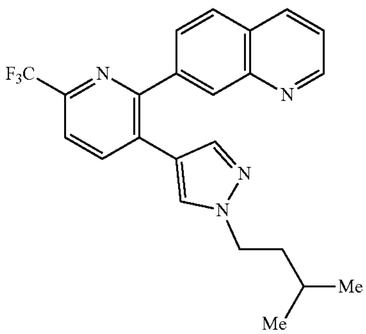 [SMILES: CC(C)CCn1cc(-c2ccc(C(F)(F)F)nc2-c2ccc3cccnc3c2)cn1] | 7-{3-[1-(3-methylbutyl)-1H-pyrazol-4-yl]-6-(trifluoromethyl)pyridin-2-yl}quinoline | 411 |
| 50 | 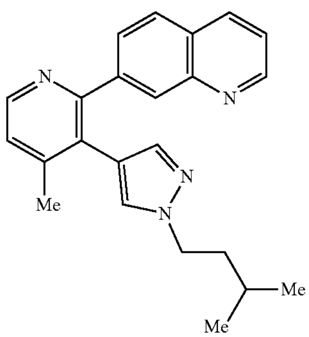 [SMILES: Cc1ccnc(-c2ccc3cccnc3c2)c1-c1cnn(CCC(C)C)c1] | 7-{4-methyl-3-[1-(3-methylbutyl)-1H-pyrazol-4-yl]pyridin-2-yl}quinoline | 357 |
| 51 | 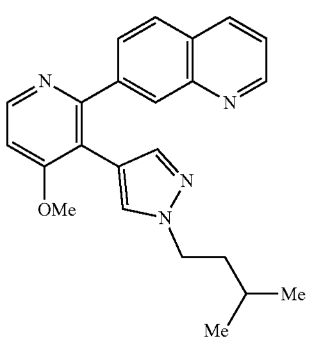 [SMILES: COc1ccnc(-c2ccc3cccnc3c2)c1-c1cnn(CCC(C)C)c1] | 7-{4-methoxy-3-[1-(3-methylbutyl)-1H-pyrazol-4-yl]pyridin-2-yl}quinoline | 373 |
| 52 | 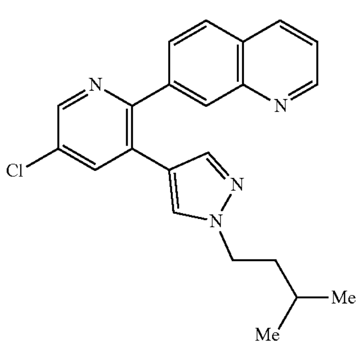 [SMILES: CC(C)CCn1cc(-c2cc(Cl)cnc2-c2ccc3cccnc3c2)cn1] | 7-{5-chloro-3-[1-(3-methylbutyl)-1H-pyrazol-4-yl]pyridin-2-yl}quinoline | 377 |

TABLE 3-continued

| Ex | Structure | Name | MS (M + 1) |
|---|---|---|---|
| 53 | 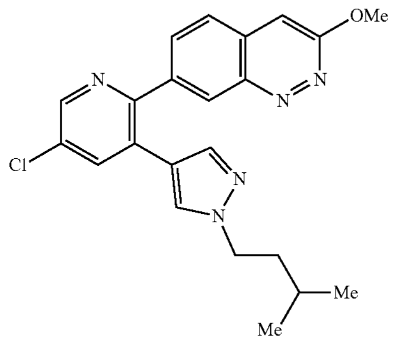 [SMILES: COc1cc2ccc(-c3ncc(Cl)cc3-c3cnn(CCC(C)C)c3)cc2nn1] | 7-{5-chloro-3-[1-(3-methylbutyl)-1H-pyrazol-4-yl]pyridin-2-yl}-3-methoxycinnoline | 408 |
| 54 | 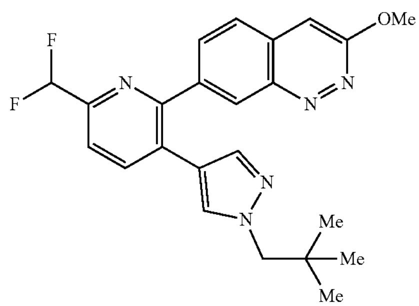 [SMILES: COc1cc2ccc(-c3nc(C(F)F)ccc3-c3cnn(CC(C)(C)C)c3)cc2nn1] | 7-{6-(difluoromethyl)-3-[1-(2,2-dimethylpropyl)-1H-pyrazol-4-yl]pyridin-2-yl}-3-methoxycinnoline | 424 |
| 55 | 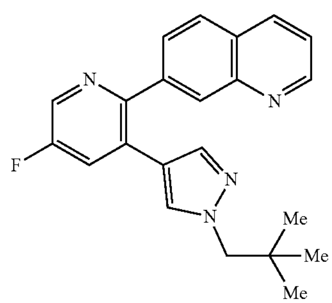 [SMILES: CC(C)(C)Cn1cc(-c2cc(F)cnc2-c2ccc3cccnc3c2)cn1] | 7-{3-[1-(2,2-dimethylpropyl)-1H-pyrazol-4-yl]-5-fluoropyridin-2-yl}quinoline | 361 |
| 56 | 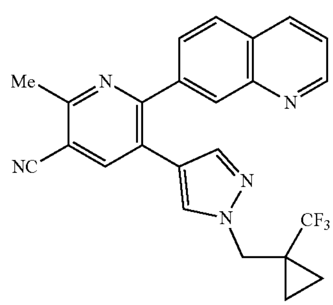 | 2-methyl-6-quinolin-7-yl-5-(1-{[1-(trifluoromethyl)cyclopropyl]methyl}-1H-pyrazol-4-yl)pyridine-3-carbonitrile | 434 |
| 57 | 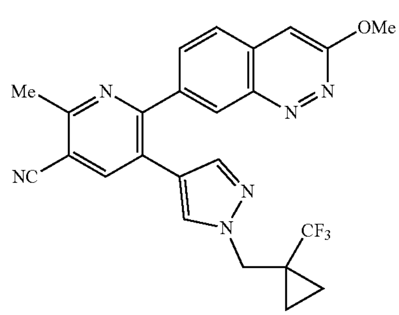 [SMILES: COc1cc2ccc(-c3nc(C)c(C#N)cc3-c3cnn(CC4(C(F)(F)F)CC4)c3)cc2nn1] | 6-(3-methoxycinnolin-7-yl)-2-methyl-5-(1-{[1-(trifluoromethyl)cyclopropyl]methyl}-1H-pyrazol-4-yl)pyridine-3-carbonitrile | 465 |

Example 58

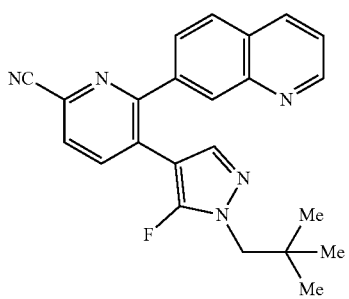

5-[1-(2,2-dimethylpropyl)-5-fluoro-1H-pyrazol-4-yl]-6-quinolin-7-ylpyridine-2-carbonitrile To an acetonitrile (8 mL) solution of 5-[1-(2,2-dimethylpropyl)-1H-pyrazol-4-yl]-6-quinolin-7-ylpyridine-2-carbonitrile (EXAMPLE 37, 260 mg, 0.71 mmol) was added 1-chloromethyl-4-fluoro-1,4-diazoniabicyclo[2.2.2]octane bis(tetrafluoroborate) (376 mg, 1.06 mmol). The mixture was stirred at 85° C. for 16 hours. The solvent was concentrated in vacuo, and the residue was dissolved in ethyl acetate (20 mL). The solution was washed with brine (15 mL), dried (sodium sulfate), filtered, and concentrated in vacuo to afford the crude product. Purification by reverse phase HPLC (acetonitrile/water with 0.05% trifluoroacetic acid) to afford the title compound as the trifluoroacetate salt. LC/MS=386 [M+1]. $^1$H-NMR (CD$_3$OD, 400 MHz) δ 9.04 (s, 1H), 8.74 (d, J=8.0 Hz, 1H), 8.16-8.23 (m, 3H), 8.01 (d, J=8.0 Hz, 1H), 7.87 (d, J=8.0 Hz, 1H), 7.81 (dd, J=4.0, 8.0 Hz, 1H), 7.47 (d, J=4.0 Hz, 1H), 3.70 (s, 2H), 0.76 (s, 9H).

Example 59

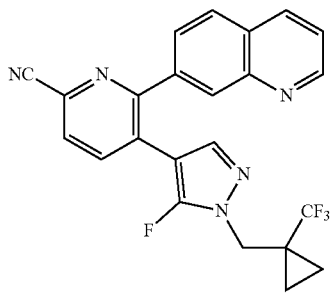 [SMILES: N#Cc1ccc(-c2cnn(CC3(C(F)(F)F)CC3)c2F)c(-c2ccc3cccnc3c2)n1]

5-(5-fluoro-1-{[1-(trifluoromethyl)cyclopropyl]methyl}-1H-pyrazol-4-yl)-6-quinolin-7-ylpyridine-2-carbonitrile The title compound was made by following the procedures described for EXAMPLE 58, substituting 6-quinolin-7-yl-5-(1-{[1-(trifluoromethyl)cyclopropyl]methyl}-1H-pyrazol-4-yl)pyridine-2-carbonitrile (EXAMPLE 44) for 5-[1-(2,2-dimethylpropyl)-1H-pyrazol-4-yl]-6-quinolin-7-ylpyridine-2-carbonitrile. LC/MS=438 [M+1]. $^1$H-NMR (CD$_3$OD, 400 MHz) δ 9.07 (d, J=4.0 Hz, 1H), 8.87 (d, J=8.0 Hz, 1H), 8.25 (s, 1H), 8.15-8.21 (m, 2H), 8.00 (d, J=8.0 Hz, 1H), 7.87-7.90 (m, 2H), 7.42 (d, J=2.8 Hz, 1H), 4.15 (s, 2H), 0.93 (d, J=5.6 Hz, 4H).

Example 60

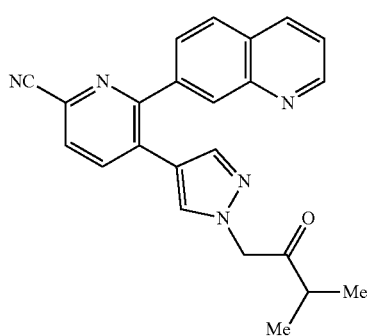 [SMILES: CC(C)C(=O)Cn1cc(-c2ccc(C#N)nc2-c2ccc3cccnc3c2)cn1]

5-[1-(3-methyl-2-oxobutyl)-1H-pyrazol-4-yl]-6-quinolin-7-ylpyridine-2-carbonitrile To a dichloromethane (5 mL) solution of 5-[1-(2-hydroxy-3-methylbutyl)-1H-pyrazol-4-yl]-6-quinolin-7-ylpyridine-2-carbonitrile (EXAMPLE 46, 15 mg, 0.039 mmol) was added 1,1,1-triacetoxy-1,1-dihydro-1,2-benziodoxol-3(1H)-one (20 mg, 0.047 mmol). The reaction mixture was stirred at 18° C. under nitrogen for 3 hours. It was diluted with dichloromethane (15 mL), filtered, and concentrated in vacuo. Purification by reverse phase HPLC (acetonitrile/water with 0.05% trifluoroacetic acid) to afford the title compound as the trifluoroacetate salt. LC/MS=382 [M+1]. $^1$H-NMR (CD$_3$OD, 400 MHz) δ 9.11 (d, J=4.4 Hz, 1H), 8.80 (d, J=4.4 Hz, 1H), 8.20-8.26 (m, 3H), 7.91-7.98 (m, 3H), 7.44 (s, 1H), 7.37 (s, 1H), 5.06 (s, 2H), 2.62-2.69 (m, 1H), 1.04 (d, J=6.8 Hz, 6H).

Example 61

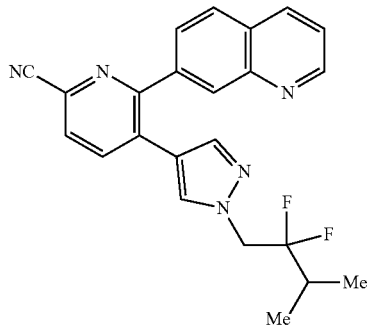 [SMILES: CC(C)C(F)(F)Cn1cc(-c2ccc(C#N)nc2-c2ccc3cccnc3c2)cn1]

5-[1-(2,2-difluoro-3-methylbutyl)-1H-pyrazol-4-yl]-6-quinolin-7-ylpyridine-2-carbonitrile To a dichloromethane (10 mL) solution of 5-[1-(3-methyl-2-oxobutyl)-1H-pyrazol-4-yl]-6-quinolin-7-ylpyridine-2-carbonitrile (EXAMPLE 60, 50 mg, 0.131 mmol) at 0° C. was added N,N-diethylaminosulfur trifluoride (0.052 mL, 0.39 mmol). The reaction mixture was stirred at 15° C. for 20 hours. It was mixture was cooled to 0° C., and saturated sodium bicarbonate (10 mL) was added. The aqueous layer was extracted with dichloromethane (15 mL×3). The combined organic extracts were dried (sodium sulfate), filtered, and concentrated in vacuo. Purification by reverse phase HPLC (acetonitrile/water with 0.05% trifluoroacetic acid) to afford the title compound as the trifluoroacetate salt. LC/MS=404 [M+1]. $^1$H-NMR (CDCl$_3$, 400 MHz) δ 8.93 (d, J=2.4 Hz, 1H), 8.15-8.20 (m, 2H), 8.17 (s, 1H), 7.92 (d, J=8.0 Hz, 1H), 7.83 (d, J=8.4 Hz, 1H), 7.72 (J=8.0 Hz, 1H), 7.58 (t, J=8.4 Hz, 1H), 7.37 (s, 1H), 7.12 (s, 1H), 4.31 (t, J=26.4 Hz, 2H), 1.72-1.83 (m, 1H), 0.94 (d, J=6.8 Hz, 1H).

Example 62

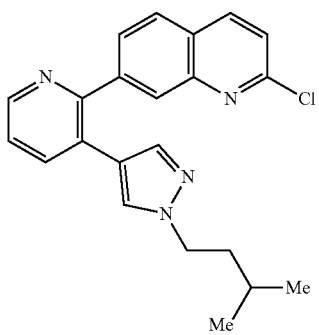 [SMILES: CC(C)CCn1cc(-c2cccnc2-c2ccc3ccc(Cl)nc3c2)cn1]

2-chloro-7-{3-[1-(3-methylbutyl)-1H-pyrazol-4-yl] pyridin-2-yl}quinoline

Step 1: 7-chloroquinolin-2(1H)-one

In a microwave vial, 2-bromo-7-chloroquinoline (2.0 g, 8.3 mmol) was suspended in water (10 mL)/acetic acid (10 mL). It was capped and irradiated with microwaves at 160° C. for 25 minutes. After cooling, the title compound was collected by filtration and used in the subsequent step without further purification. LC/MS=180 [M+1].

Step 2: 7-(4,4,5,5-tetramethyl-1,3,2-dioxaborolan-2-yl)quinolin-2(1H)-one

To a mixture of 7-chloroquinolin-2(1H)-one (1.22 g, 6.79 mmol), bis(pinacolato) diboron (3.45 g, 13.6 mmol), 2-(dicyclohexylphosphino)-2',4',6'-triisopropylbiphenyl (0.13 g, 0.27 mmol), tris(dibenzylideneacetone)dipalladium(0) (0.062 g, 0.068 mmol), and potassium acetate (2.00 g, 20.4 mmol) was charged dioxane (34 mL). The reaction mixture was sparged with nitrogen for 20 min and heated at 80° C. for 12 hours. It was charged with saturated aqueous sodium carbonate and extracted with ethyl acetate (30 mL×2). The combined organic extracts were dried (potassium carbonate) and concentrated in vacuo to afford the crude solid. It was triturated with hexanes, affording the title compound as a solid that was collected by filtration and used in the subsequent step without further purification. LC/MS=272 [M+1]. $^1$H-NMR (DMSO-d$_6$, 500 MHz) δ 11.72 (s, 1H), 7.92 (d, J=9.5 Hz, 1H), 7.61-7.69 (m, 2H), 7.42 (d, J=7.9 Hz, 1H), 6.55 (d, J=9.5 Hz, 1H), 1.32 (s, 12H).

Step 3: 7-(3-(1-isopentyl-1H-pyrazol-4-yl)pyridin-2-yl)quinolin-2(1H)-one

To a mixture of 2-chloro-3-(1-isopentyl-1H-pyrazol-4-yl) pyridine (INTERMEDIATE E1, 1.42 g, 5.70 mmol), 7-(4, 4,5,5-tetramethyl-1,3,2-dioxaborolan-2-yl)quinolin-2(1H)-one (1.55 g, 5.70 mmol), [1,1'-bis(di-tert-butylphosphino) ferrocene]dichloro palladium(II) (74 mg, 0.11 mmol), and a 1.0 M aqueous solution of potassium phosphate (17 mL, 17 mmol) was charged tetrahydrofuran (28.5 mL). The reaction mixture was sparged with nitrogen for 20 minutes and heated to reflux for 16 hours. After cooling to room temperature, the reaction mixture was charged with ethyl acetate (50 mL). The aqueous layer was extracted with ethyl acetate (50 mL), and the combined organic extracts were dried (potassium carbonate), filtered and concentrated in vacuo. The crude product was dissolved in a minimal amount of dichloromethane, and slow addition of hexanes (100 mL) precipitated a solid. The title compound was collected through filtration, which was used in the subsequent step without further purification. LC/MS=359 [M+1]. $^1$H-NMR (DMSO-d$_6$, 500 MHz) δ 11.74 (s, 1H), 8.55 (dd, J=1.5, 4.7 Hz, 1H), 7.89-7.97 (m, 2H), 7.61 (d, J=8.1 Hz, 1H), 7.44 (dd, J=4.7, 7.8 Hz, 1H), 7.36 (s, 2H), 7.30 (s, 1H), 7.09 (dd, J=1.5, 8.0 Hz, 1H), 6.52 (d, J=9.6 Hz, 1H), 3.98 (t, J=6.9 Hz, 2H), 1.51 (q, J=6.9 Hz, 2H), 1.20-1.29 (m, 1H), 0.76 (d, J=6.6 Hz, 6H).

Step 4: 2-chloro-7-{3-[1-(3-methylbutyl)-1H-pyrazol-4-yl]pyridin-2-yl}quinoline

To 7-(3-(1-isopentyl-1H-pyrazol-4-yl)pyridin-2-yl)quinolin-2(1H)-one (1.58 g, 4.41 mmol) was charged phosphorus oxychloride (15 mL, 160 mmol). The reaction mixture was heated to 95° C. for 2 hours. Excess phosphorus oxychloride was removed in vacuo. The residue was charged with ice water, and vigorous stirring afforded a suspension. The aqueous layer was extracted with ethyl acetate (100 mL×2). The combined organic extracts were dried (potassium carbonate) and concentrated in vacuo. Purification by column chromatography over silica gel, eluting with hexanes/ethyl acetate, afforded the title compound. LC/MS=377 [M+1]. $^1$H-NMR (DMSO-d$_6$, 500 MHz) δ 8.61 (dd, J=1.6, 4.7 Hz, 1H), 8.49 (d, J=8.6 Hz, 1H), 8.03 (d, J=8.4 Hz, 1H), 7.94 (dd, J=1.6, 7.8 Hz, 1H), 7.88 (s, 1H), 7.66 (dd, J=1.6, 8.4 Hz, 1H), 7.62 (d, J=8.6 Hz, 1H), 7.48 (dd, J=4.7, 7.8 Hz, 1H), 7.39 (s, 1H), 7.31 (s, 1H), 3.96 (t, J=6.9 Hz, 2H), 1.47 (q, J=6.9 Hz, 2H), 1.10-1.20 (m, 1H), 0.69 (d, J=6.6 Hz, 6H).

Example 63

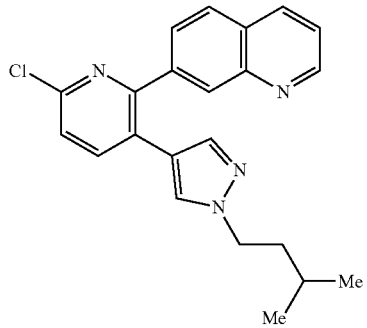 [SMILES: CC(C)CCn1cc(-c2ccc(Cl)nc2-c2ccc3cccnc3c2)cn1]

7-{6-chloro-3-[1-(3-methylbutyl)-1H-pyrazol-4-yl]pyridin-2-yl}quinoline

Step 1: 5-(1-isopentyl-1H-pyrazol-4-yl)-6-(quinolin-7-yl)pyridin-2(1H)-one

In a microwave reaction vial, 7-{6-methoxy-3-[1-(3-methylbutyl)-1H-pyrazol-4-yl]pyridin-2-yl}quinoline (EXAMPLE 48, 2.5 g, 6.71 mmol) was suspended in 2 N hydrochloric acid. The vial was capped and irradiated with microwaves at 140° C. for 40 minutes. The reaction mixture was concentrated in vacuo to afford the title compound as the crude product, which was used in the subsequent reaction without further purification. LC/MS=359 [M+1].

Step 2: 7-{6-chloro-3-[1-(3-methylbutyl)-1H-pyrazol-4-yl]pyridin-2-yl}quinoline To 5-(1-isopentyl-1H-pyrazol-4-yl)-6-(quinolin-7-yl)pyridin-2(1H)-one (50 mg, 0.139 mmol) was charged phosphorus oxychloride (0.175 mL, 1.87 mmol), followed by N,N-diisopropylethylamine (24 µL, 0.139 mmol). The reaction mixture was stirred at 90° C. for 3.5 hours. The reaction mixture was then cool to room temperature and poured into an ice bath. The aqueous layer was extracted with diethyl ether (10 mL×3). The combined organic extracts were washed with sodium hydrogencarbonate solution, brine, dried (sodium sulfate), filtered, and concentrated in vacuo to afford the crude product. Purification by reverse phase HPLC (acetonitrile/water with 0.05% trifluoroacetic acid) to afford the title compound as the trifluoroacetate salt. LC/MS=377 [M+1]. $^1$H-NMR (DMSO-d$_6$, 500 MHz) δ 8.96 (d, J=4.1 Hz, 1H), 8.48 (d, J=8.0 Hz, 1H), 7.94-8.09 (m, 3H), 7.57-7.67 (m, 3H), 7.46 (s, 1H), 7.28 (s, 1H), 3.96 (t, J=6.9 Hz, 2H), 1.47 (q, J=7.0 Hz, 2H), 1.12-1.28 (m, 1H), 0.70 (d, J=6.6 Hz, 6H).

Example 64

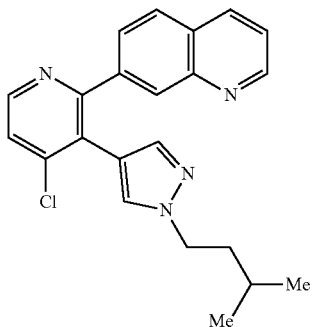 [SMILES: CC(C)CCn1cc(-c2c(Cl)ccnc2-c2ccc3cccnc3c2)cn1]

7-{4-chloro-3-[1-(3-methylbutyl)-1H-pyrazol-4-yl]pyridin-2-yl}quinoline

Step 1: 2-chloro-3-(1-isopentyl-1H-pyrazol-4-yl)pyridine 1-oxide

To a dichloromethane (40 mL) solution of 2-chloro-3-(1-isopentyl-1H-pyrazol-4-yl)pyridine (INTERMEDIATE E1, 1.0 g, 4.0 mmol) was added 3-chloroperbenzoic acid (3.59 g, 16.0 mmol). The reaction mixture was stirred at room temperature for 12 hours. Calcium hydroxide (2.37 g, 32.0 mmol) and methanol (40 mL) were then added, and the reaction mixture was stirred for 30 minutes. The reaction mixture was filtered through diatomaceous earth and concentrated in vacuo to afford the title compound as the crude product, which was used in the subsequent reaction without further purification. LC/MS=266 [M+1].

Step 2: 3-(1-isopentyl-1H-pyrazol-4-yl)-2-(quinolin-7-yl)pyridine 1-oxide

In a 5-mL vial, 2-chloro-3-(1-isopentyl-1H-pyrazol-4-yl)pyridine 1-oxide (25 mg, 0.094 mmol), 7-(4,4,5,5-tetramethyl-1,3,2-dioxaborolan-2-yl)quinoline (36 mg, 0.14 mmol), [1,1'-bis(di-tert-butylphosphino)ferrocene]dichloropalladium(II) (6.1 mg, 9.4 µmol), and a 1.0 M aqueous solution of potassium phosphate (0.28 mL, 0.28 mmol) was charged with tetrahydrofuran (0.94 mL). The vial was capped and irradiated with microwaves at 100° C. for 10 minutes. The reaction mixture were filtered through a liquid-liquid extraction column containing modified diatomaceous earth and concentrated in vacuo to afford the crude product. Purification by reverse phase HPLC (acetonitrile/water with 0.05% trifluoroacetic acid) afforded the title compound as the trifluoroacetate salt. LC/MS=359 [M+1]. $^1$H-NMR (DMSO-d$_6$, 500 MHz) δ 8.98 (d, J=3.1 Hz, 1H), 8.55 (d, J=8.0 Hz, 1H), 8.32 (d, J=5.6 Hz, 1H), 8.12 (d, J=8.4 Hz, 1H), 7.89 (s, 1H), 7.68 (dd, J=4.4, 8.3 Hz, 1H), 7.55-7.63 (m, 2H), 7.51 (dd, J=6.5, 8.0 Hz, 1H), 7.22 (s, 1H), 7.07 (s, 1H), 3.86 (t, J=6.9 Hz, 2H), 1.33 (q, J=6.9 Hz, 2H), 0.94-1.02 (m, 1H), 0.59 (d, J=6.6 Hz, 6H).

Step 3: 7-{4-chloro-3-[1-(3-methylbutyl)-1H-pyrazol-4-yl]pyridin-2-yl}quinoline To N,N-dimethylformamide (500 µL) at 0° C. was added phosphorus oxychloride (50 µL, 0.54 mmol). It was stirred for 10 minutes at 0° C. and allowed to warm up to room temperature. It was then added to a microwave vial containing a N,N-dimethylformamide (100 µL) solution of 3-(1-isopentyl-1H-pyrazol-4-yl)-2-(quinolin-7-yl)pyridine 1-oxide (25 mg, 0.070 mmol). LC/MS analysis of the reaction mixture showed both 7-{6-chloro-3-[1-(3-methylbutyl)-1H-pyrazol-4-yl]pyridin-2-yl}quinoline (EXAMPLE 63) and the title compound. The reaction mixture was quenched with water (50 µL), and purification by reverse phase HPLC (acetonitrile/water with 0.05% trifluoroacetic acid) afforded the title compound as the trifluoroacetate salt. LC/MS=377 [M+1]. $^1$H-NMR (DMSO-d$_6$, 500 MHz) δ 8.94 (d, J=3.9 Hz, 1H), 8.62 (d, J=5.2 Hz, 1H), 8.45 (d, J=7.8 Hz, 1H), 7.96 (s, 1H), 7.90 (d, J=8.5 Hz, 1H), 7.72 (d, J=5.2 Hz, 1H), 7.61 (dd, J=4.3, 8.2 Hz, 1H), 7.49-7.56 (m, 2H), 7.37 (s, 1H), 3.97 (t, J=6.7 Hz, 2H), 1.41 (q, J=6.8 Hz, 2H), 0.92-1.01 (m, 1H), 0.60 (d, J=6.6 Hz, 6H).

Example 65

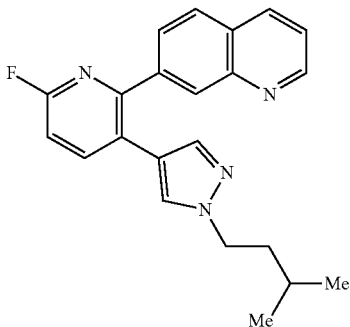 [SMILES: CC(C)CCn1cc(-c2ccc(F)nc2-c2ccc3cccnc3c2)cn1]

7-{6-fluoro-3-[1-(3-methylbutyl)-1H-pyrazol-4-yl]pyridin-2-yl}quinoline

To a sulfolane (1.3 mL) solution of 7-{6-chloro-3-[1-(3-methylbutyl)-1H-pyrazol-4-yl]pyridin-2-yl}quinoline (EXAMPLE 63, 50 mg, 0.133 mmol) was added cesium fluoride (403 mg, 2.65 mmol). The reaction mixture was heated to 200° C. for 16 hours, loaded onto a strong cation exchange cartridge, and eluted with ammonia in methanol. The filtrate was concentrated in vacuo, and purification of the crude product by reverse phase HPLC (acetonitrile/water with 0.05% trifluoroacetic acid) afforded the title compound as the trifluoroacetate salt. LC/MS=361 [M+1]. $^1$H-NMR (DMSO-$d_6$, 500 MHz) δ 8.95 (d, J=3.9 Hz, 1H), 8.47 (d, J=8.0 Hz, 1H), 8.12 (t, J=8.2 Hz, 1H), 8.04 (s, 1H), 7.99 (d, J=8.4 Hz, 1H), 7.55-7.68 (m, 2H), 7.46 (s, 1H), 7.22-7.34 (m, 2H), 3.96 (t, J=6.9 Hz, 2H), 1.48 (q, J=6.9 Hz, 2H), 1.11-1.31 (m, 1H), 0.70 (d, J=6.6 Hz, 6H).

Example 66

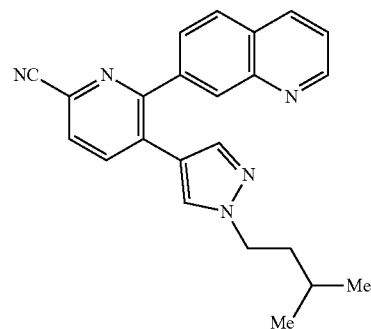 [SMILES: CC(C)CCn1cc(-c2ccc(C#N)nc2-c2ccc3cccnc3c2)cn1]

5-[1-(3-methylbutyl)-1H-pyrazol-4-yl]-6-quinolin-7-ylpyridine-2-carbonitrile

In a microwave vial, a N,N-dimethylacetamide (500 µL) solution of 7-{6-chloro-3-[1-(3-methylbutyl)-1H-pyrazol-4-yl]pyridin-2-yl}quinoline (EXAMPLE 63, 10 mg, 0.027 mmol) was charged with zinc cyanide (1.9 mg, 0.016 mmol), zinc (0.2 mg, 3 µmol), sulfuric acid (0.14 µL, 2.7 µmol), and bis(di-tert-butyl(4-dimethylaminophenyl)phosphine)dichloropalladium(II) (1.9 mg, 2.7 µmol). The reaction vial was capped and irradiated with microwaves at 150° C. for 10 minutes. The combined organic extracts were filtered through a liquid-liquid extraction column containing modified diatomaceous earth. Purification by reverse phase HPLC (acetonitrile/water with 0.05% trifluoroacetic acid) afforded the title compound as the trifluoroacetate salt. LC/MS=368 [M+1]. $^1$H-NMR (DMSO-$d_6$, 500 MHz) δ 8.99 (d, J=3.7 Hz, 1H), 8.51 (d, J=8.0 Hz, 1H), 8.24 (d, J=8.1 Hz, 1H), 8.03-8.14 (m, 3H), 7.65 (dd, J=4.3, 8.2 Hz, 1H), 7.62 (d, J=8.2 Hz, 1H), 7.51 (s, 1H), 7.33 (s, 1H), 3.96 (t, J=6.9 Hz, 2H), 1.46 (q, J=6.9 Hz, 2H), 1.15-1.23 (m, 1H), 0.70 (d, J=6.6 Hz, 6H).

Example 67

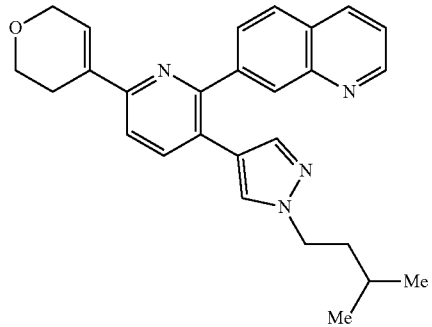 [SMILES: CC(C)CCn1cc(-c2ccc(C3=CCOCC3)nc2-c2ccc3cccnc3c2)cn1]

7-{6-(3,6-dihydro-2H-pyran-4-yl)-3-[1-(3-methylbutyl)-1H-pyrazol-4-yl]pyridin-2-yl}quinoline In a microwave vial, a mixture of 2-(3,6-dihydro-2H-pyran-4-yl)-4,4,5,5-tetramethyl-1,3,2-dioxaborolane (15 mg, 0.073 mmol), [1,1'-bis(di-tert-butylphosphino)ferrocene]dichloropalladium(II) (2.1 mg, 3.3 µmol), and a 5.0 M aqueous solution of potassium phosphate (40 µL, 0.20 mmol) was charged with a tetrahydrofuran (330 µL) solution of 7-{6-chloro-3-[1-(3-methylbutyl)-1H-pyrazol-4-yl]pyridin-2-yl}quinoline (EXAMPLE 63, 25 mg, 0.066 mmol). The reaction mixture was heated to 120° C. for 12 hours, filtered through a liquid-liquid extraction column containing modified diatomaceous earth and concentrated in vacuo to afford the crude product. Purification by reverse phase HPLC (acetonitrile/water with 0.05% trifluoroacetic acid) afforded the title compound as the trifluoroacetate salt. LC/MS=425 [M+1]. $^1$H-NMR (DMSO-$d_6$, 500 MHz) δ 9.00 (s, 1H), 8.57 (d, J=8.5 Hz, 1H), 7.99-8.15 (m, 2H), 7.94 (d, J=8.2 Hz, 1H), 7.60-7.74 (m, 3H), 7.45 (s, 1H), 7.27 (s, 1H), 6.85 (s, 1H), 4.29 (d, J=2.6 Hz, 1H), 3.91-4.06 (m, 3H), 3.84 (t, J=5.5 Hz, 1H), 2.58-2.63 (m, 2H), 1.49 (q, J=6.9 Hz, 2H), 1.15-1.32 (m, 2H), 0.72 (d, J=6.6 Hz, 6H).

Example 68

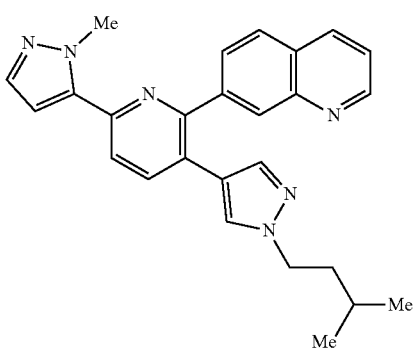 [SMILES: CC(C)CCn1cc(-c2ccc(-c3ccnn3C)nc2-c2ccc3cccnc3c2)cn1]

7-{3-[1-(3-methylbutyl)-1H-pyrazol-4-yl]-6-(1-methyl-1H-pyrazol-5-yl)pyridin-2-yl}quinoline The title compound was made by following the procedures described for EXAMPLE 67, substituting 1-methyl-5-(4,4,5,5-tetramethyl-1,3,2-dioxaborolan-2-yl)-1H-pyrazole for 2-(3,6-dihydro-2H-pyran-4-yl)-4,4,5,5-tetramethyl-1,3,2-dioxaborolane. LC/MS=423 [M+1]. ¹H-NMR (DMSO-d$_6$, 500 MHz) δ 9.00 (s, 1H), 8.56 (d, J=7.9 Hz, 1H), 8.17 (s, 1H), 8.06 (d, J=6.2 Hz, 1H), 8.05 (d, J=6.3 Hz, 1H), 7.89 (d, J=8.2 Hz, 1H), 7.72 (d, J=9.7 Hz, 1H), 7.68 (dd, J=4.3, 8.3 Hz, 1H), 7.49-7.54 (m, 2H), 7.32 (s, 1H), 6.92 (d, J=1.9 Hz, 1H), 4.20 (s, 3H), 3.98 (t, J=7.0 Hz, 2H), 1.50 (q, J=6.9 Hz, 2H), 1.19-1.31 (m, 1H), 0.73 (d, J=6.6 Hz, 6H).

Example 69

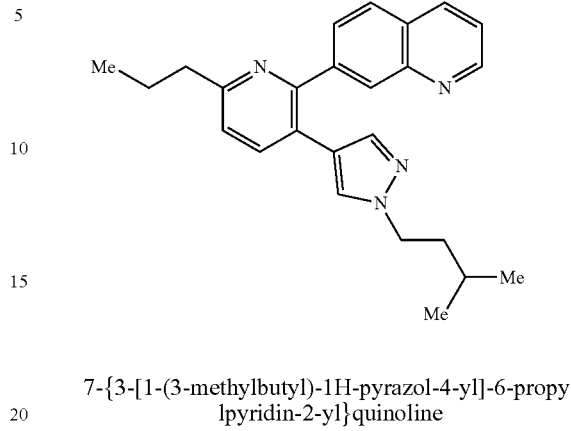

7-{3-[1-(3-methylbutyl)-1H-pyrazol-4-yl]-6-propylpyridin-2-yl}quinoline

To a tetrahydrofuran (330 µL) solution of 7-{6-chloro-3-[1-(3-methylbutyl)-1H-pyrazol-4-yl]pyridin-2-yl}quinoline (EXAMPLE 63, 25 mg, 0.066 mmol) was added propylzinc (II) bromide (0.37 mmol), followed by chloro(2-dicyclohexylphosphino-2',4',6'-triisopropyl-1,1'-biphenyl)[2-(2'-amino-1,1'-biphenyl)]palladium(II) (0.066 mmol). The reaction was heated to 130° C. for 2 hours, quenched with water, filtered through a liquid-liquid extraction column containing modified diatomaceous earth, and concentrated in vacuo to afford the crude product. Purification by reverse phase HPLC (acetonitrile/water with 0.05% trifluoroacetic acid) afforded the title compound as the trifluoroacetate salt. LC/MS=385 [M+1]. ¹H-NMR (DMSO-d$_6$, 500 MHz) δ 8.96 (d, J=2.9 Hz, 1H), 8.48 (d, J=8.2 Hz, 1H), 8.06 (s, 1H), 7.99 (d, J=8.5 Hz, 1H), 7.91 (br s, 1H), 7.58-7.65 (m, 2H), 7.38-7.45 (m, 2H), 7.24 (s, 1H), 3.95 (t, J=6.9 Hz, 2H), 2.80 (t, J=7.6 Hz, 2H), 1.76 (sextet, J=7.3 Hz, 2H), 1.47 (q, J=6.9 Hz, 2H), 1.13-1.27 (m, 1H), 0.97 (t, J=7.3 Hz, 3H), 0.70 (d, J=6.6 Hz, 6H).

The following examples in Table 4 were prepared using the procedures outlined in the synthesis of Example 69 with the appropriate substituted alkylzinc(II) bromide.

TABLE 4

| Ex | Structure | Name | MS (M + 1) |
|---|---|---|---|
| 70 | 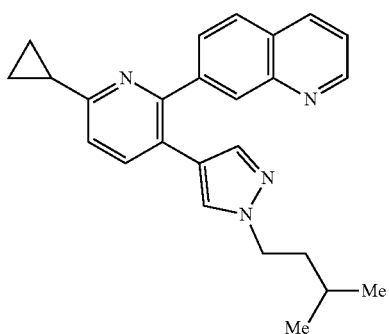 [SMILES: CC(C)CCn1cc(-c2ccc(C3CC3)nc2-c2ccc3cccnc3c2)cn1] | 7-{6-(cyclopropyl)-3-[1-(3-methylbutyl)-1H-pyrazol-4-yl]pyridin-2-yl}quinoline | 383 |

| Ex | Structure | Name | MS (M + 1) |
|---|---|---|---|
| 71 | 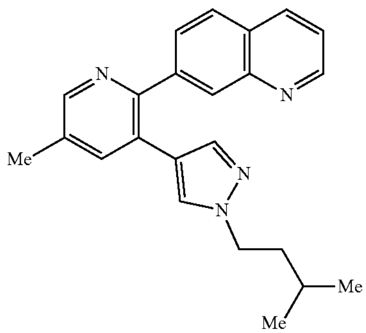 [SMILES: Cc1cnc(-c2ccc3cccnc3c2)c(-c2cnn(CCC(C)C)c2)c1] | 7-{5-methyl-3-[1-(3-methylbutyl)-1H-pyrazol-4-yl]pyridin-2-yl}quinoline | 357 |

Example 72

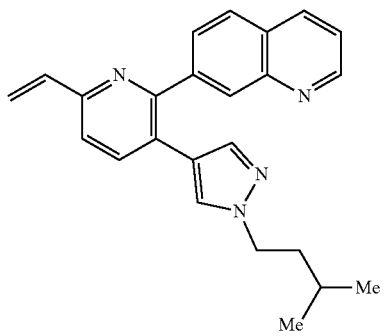 [SMILES: C=Cc1ccc(-c2cnn(CCC(C)C)c2)c(-c2ccc3cccnc3c2)n1]

7-{6-ethenyl-3-[1-(3-methylbutyl)-1H-pyrazol-4-yl]pyridin-2-yl}quinoline

In a microwave vial, a tetrahydrofuran (800 µL) solution of 7-{6-chloro-3-[1-(3-methylbutyl)-1H-pyrazol-4-yl]pyridin-2-yl}quinoline (EXAMPLE 63, 40 mg, 0.106 mmol) was charged with tetrakis(triphenylphosphine)palladium(0) (12 mg, 11 µmol) and tributyl(vinyl) stannane (37 mg, 0.117 mmol). The reaction vial was capped and irradiated with microwaves at 120° C. for 20 minutes. The reaction mixture was concentrated in vacuo to afford the crude product. Purification by reverse phase HPLC (acetonitrile/water with 0.05% trifluoroacetic acid) afforded the title compound as the trifluoroacetate salt. LC/MS=369 [M+1]. $^1$H-NMR (DMSO-d$_6$, 500 MHz) δ 8.98 (s, 1H), 8.52 (d, J=8.2 Hz, 1H), 8.07 (s, 1H), 8.01 (d, J=8.4 Hz, 1H), 7.96 (d, J=8.0 Hz, 1H), 7.85-7.93 (m, 1H), 7.61-7.69 (m, 2H), 7.41 (d, J=10.7 Hz, 1H), 7.25 (s, 1H), 6.89 (dd, J=10.9, 17.5 Hz, 1H), 6.28 (d, J=17.5 Hz, 1H), 5.52 (d, J=11.9 Hz, 1H), 3.95 (t, J=6.9 Hz, 2H), 1.47 (q, J=6.9 Hz, 2H), 1.16-1.28 (m, 1H), 0.70 (d, J=6.6 Hz, 6H).

Example 73

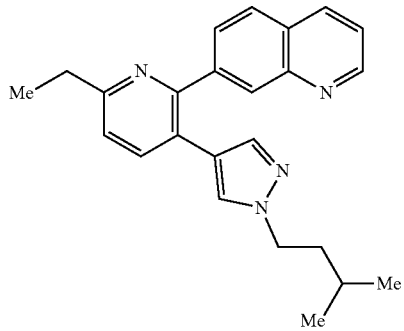 [SMILES: CCc1ccc(-c2cnn(CCC(C)C)c2)c(-c2ccc3cccnc3c2)n1]

7-{6-ethyl-3-[1-(3-methylbutyl)-1H-pyrazol-4-yl]pyridin-2-yl}quinoline

To an ethanol (270 µL) solution of 7-{6-ethenyl-3-[1-(3-methylbutyl)-1H-pyrazol-4-yl]pyridin-2-yl}quinoline (EXAMPLE 72, 20 mg, 0.054 mmol) was added palladium on charcoal (5.8 mg). It was stirred under hydrogen for 24 hours. The reaction mixture was concentrated in vacuo to afford the crude product. Purification by reverse phase HPLC (acetonitrile/water with 0.05% trifluoroacetic acid) afforded the title compound as the trifluoroacetate salt. LC/MS=371 [M+1]. $^1$H-NMR (DMSO-d$_6$, 500 MHz) δ 8.97 (s, 1H), 8.50 (d, J=8.3 Hz, 1H), 8.08 (s, 1H), 8.00 (d, J=8.5 Hz, 1H), 7.94 (d, J=7.5 Hz, 1H), 7.64 (dd, J=4.2, 8.2 Hz, 1H), 7.61 (d, J=8.5 Hz, 1H), 7.43 (d, J=8.4 Hz, 1H), 7.41 (s, 1H), 7.24 (s, 1H), 3.96 (t, J=6.9 Hz, 2H), 2.86 (q, J=7.6 Hz, 2H), 1.47 (q, J=6.9 Hz, 2H), 1.30 (t, J=7.6 Hz, 3H), 1.16-1.23 (m, 1H), 0.70 (d, J=6.6 Hz, 6H).

Example 74

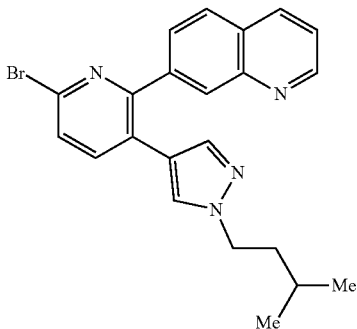 [SMILES: CC(C)CCn1cc(-c2ccc(Br)nc2-c2ccc3cccnc3c2)cn1]

7-{6-bromo-3-[1-(3-methylbutyl)-1H-pyrazol-4-yl]pyridin-2-yl}quinoline

To a N,N-dimethylformamide (0.28 mL) solution of 5-(1-isopentyl-1H-pyrazol-4-yl)-6-(quinolin-7-yl)pyridin-2(1H)-one (EXAMPLE 63, STEP 1, 20 mg, 0.056 mmol) was added phosphorus oxybromide (240 mg, 0.837 mmol). The reaction mixture was heated to 180° C. in a sealed microwave vial for 2 hours, quenched with water, and extracted with ethyl acetate. The combined organic extracts were filtered through a liquid-liquid extraction column containing modified diatomaceous earth. Purification by reverse phase HPLC (acetonitrile/water with 0.05% trifluoroacetic acid) afforded the title compound as the trifluoroacetate salt. LC/MS=421 [M+1]. $^1$H-NMR (DMSO-$d_6$, 500 MHz) δ 8.97 (d, J=3.8 Hz, 1H), 8.50 (d, J=8.0 Hz, 1H), 7.96-8.08 (m, 2H), 7.92 (d, J=8.2 Hz, 1H), 7.73 (d, J=8.2 Hz, 1H), 7.64 (dd, J=4.3, 8.2 Hz, 1H), 7.59 (d, J=8.4 Hz, 1H), 7.47 (s, 1H), 7.28 (s, 1H), 3.96 (t, J=6.9 Hz, 2H), 1.47 (q, J=6.9 Hz, 2H), 1.15-1.24 (m, 1H), 0.70 (d, J=6.6 Hz, 6H).

Example 75

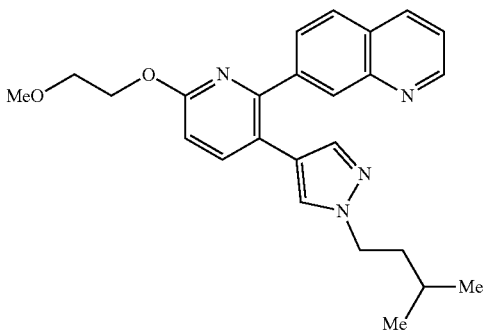 [SMILES: COCCOc1ccc(-c2cnn(CCC(C)C)c2)c(-c2ccc3cccnc3c2)n1]

7-{6-(2-methoxyethoxy)-3-[1-(3-methylbutyl)-1H-pyrazol-4-yl]pyridin-2-yl}quinoline In a microwave vial, a tetrahydrofuran (450 μL) solution of 5-(1-isopentyl-1H-pyrazol-4-yl)-6-(quinolin-7-yl)pyridin-2(1H)-one (EXAMPLE 63, STEP 1, 16 mg, 0.045 mmol) was charged to a mixture of polymer-bound triphenylphosphine (0.45 mmol) and 2-methoxyethan-1-ol (0.045 mmol), followed by diisopropyl azodicarboxylate (26 μL, 0.13 mmol). The reaction mixture was sonicated for 12 hours, filtered, and concentrated in vacuo to afford the crude product. Purification by reverse phase HPLC (acetonitrile/water with 0.05% trifluoroacetic acid) afforded the title compound as the trifluoroacetate salt. LC/MS=417 [M+1]. $^1$H-NMR (DMSO-$d_6$, 500 MHz) δ 8.96 (d, J=3.3 Hz, 1H), 8.49 (d, J=8.2 Hz, 1H), 8.09 (d, J=6.9 Hz, 1H), 7.97 (d, J=8.4 Hz, 1H), 7.84 (d, J=8.5 Hz, 1H), 7.59-7.66 (m, 2H), 7.40 (s, 1H), 7.22 (s, 1H), 6.93 (d, J=8.5 Hz, 1H), 4.45 (d, J=4.6 Hz, 2H), 3.96 (t, J=7.0 Hz, 2H), 3.69 (d, J=4.8 Hz, 2H), 3.31 (s, 3H), 1.49 (q, J=6.9 Hz, 2H), 1.17-1.28 (m, 1H), 0.72 (d, J=6.0 Hz, 6H).

Example 76

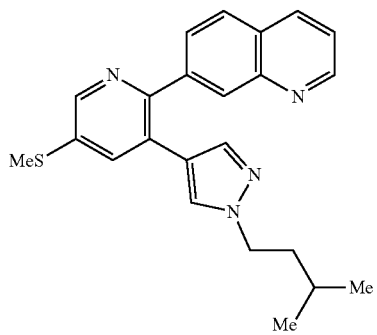 [SMILES: CSc1cnc(-c2ccc3cccnc3c2)c(-c2cnn(CCC(C)C)c2)c1]

7-{3-[1-(3-methylbutyl)-1H-pyrazol-4-yl]-5-(methylsulfanyl)pyridin-2-yl}quinoline Step 1: 2-chloro-3-(1-isopentyl-1H-pyrazol-4-yl)-5-(methylthio)pyridine To a tetrahydrofuran (14.5 mL) solution of 6-chloro-5-(1-isopentyl-1H-pyrazol-4-yl)pyridin-3-amine (INTERMEDIATE E7, 1.00 g, 3.78 mmol) at 0° C. was added 2.0 M hydrochloric acid (7.55 mL, 15.1 mmol), followed by sodium nitrite (0.391 g, 5.67 mmol). After being stirred at 0° C. for 1 hour, the reaction mixture was charged with sodium thiomethoxide (0.529 g, 7.55 mmol). It was allowed to warm to room temperature slowly. After 12 hours, the reaction mixture was extracted with ethyl acetate (20 mL) and concentrated in vacuo. Purification by column chromatography over silica gel, eluting with hexanes/ethyl acetate, afforded the title compound. LC/MS=296 [M+1].

Step 2: 7-{3-[1-(3-methylbutyl)-1H-pyrazol-4-yl]-5-(methylsulfanyl)pyridin-2-yl}quinoline To a N,N-dimethylacetamide (0.34 mL) solution of 2-chloro-3-(1-isopentyl-1H-pyrazol-4-yl)-5-(methylthio)pyridine (20 mg, 0.068 mmol) was added quinoline-7-boronic acid (13 mg, 0.074 mmol), [1,1'-bis(di-tert-butylphosphino)ferrocene]dichloropalladium(II) (2.2 mg, 3.4 μmol), and 1.0 M aqueous solution of potassium phosphate (200 μL, 0.20 mmol). The reaction was heated at 120° C. for 12 hours, diluted with ethyl acetate (3 mL), filtered through a liquid-liquid extraction column containing modified diatomaceous earth, and concentrated in vacuo to afford the crude product. Purification by reverse phase HPLC (acetonitrile/water with 0.05% trifluoroacetic acid) afforded the title compound as the trifluoroacetate salt. LC/MS=389 [M+1]. ¹H-NMR (DMSO-d₆, 500 MHz) δ 8.97 (d, J=4.2 Hz, 1H), 8.46-8.57 (m, 2H), 8.04 (s, 1H), 8.00 (d, J=8.6 Hz, 1H), 7.81 (s, 1H), 7.64 (dd, J=4.3, 8.1 Hz, 1H), 7.61 (d, J=8.4 Hz, 1H), 7.51 (s, 1H), 7.30 (s, 1H), 3.97 (t, J=6.9 Hz, 2H), 2.63 (s, 3H), 1.49 (q, J=6.8 Hz, 2H), 1.13-1.30 (m, 1H), 0.71 (d, J=6.6 Hz, 6H).

Example 77

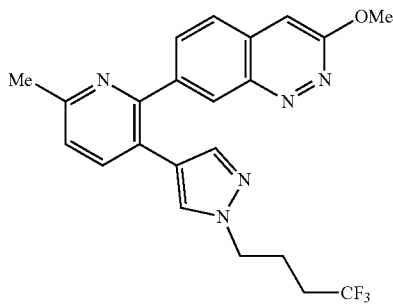 [SMILES: COc1cc2ccc(-c3nc(C)ccc3-c3cnn(CCCC(F)(F)F)c3)cc2nn1]

3-methoxy-7-{6-methyl-3-[1-(4,4,4-trifluorobutyl)-1H-pyrazol-4-yl]pyridin-2-yl}cinnoline Step 1: 4,4,4-trifluorobutyl 4-methylbenzenesulfonate A dichloromethane (0.40 mL) solution of p-toluenesulfonyl chloride (75 mg, 0.39 mmol) was charged into a 4-mL vial containing 4,4,4-trifluorobutan-1-ol (0.20 mmol), followed by N,N-diisopropylethylamine (160 µL, 0.92 mmol). The reaction mixture was stirred at room temperature for 12 hours. It was quenched by the addition of water (100 µL). The organic layer was dried by filtering through a hydrophobic frit and concentrated in vacuo to afford the title compound as the crude product, which was used in the subsequent reaction without further purification.

Step 2: 3-methoxy-7-{6-methyl-3-[1-(4,4,4-trifluorobutyl)-1H-pyrazol-4-yl]pyridin-2-yl}cinnoline To a N,N-dimethylformamide (0.5 mL) suspension of 3-methoxy-7-(6-methyl-3-(1H-pyrazol-4-yl)pyridin-2-yl) cinnoline (INTERMEDIATE F1, 30.0 mg, 0.095 mmol) was added sodium hydride (60 wt %, 20 mg, 0.5 mmol). The reaction mixture was stirred at room temperature for 10 minutes, then added to 4,4,4-trifluorobutyl 4-methylbenzenesulfonate. It was stirred at 50° C. for 12 hours and concentrated in vacuo. Purification by reverse phase HPLC (acetonitrile/water with 0.050 trifluoroacetic acid) afforded the title compound as the trifluoroacetate salt. LC/MS=428 [M+1]. ¹H-NMR (DMSO-d₆, 500 MHz) δ 8.36 (s, 1H), 7.96 (s, 1H), 7.87 (d, J=8.7 Hz, 1H), 7.69 (s, 1H), 7.66 (dd, J=1.5, 8.7 Hz, 1H), 7.56 (s, 1H), 7.46 (d, J=8.0 Hz, 1H), 7.34 (s, 1H), 4.18 (s, 3H), 4.06 (t, J=6.7 Hz, 2H), 2.60 (s, 3H), 1.97-2.11 (m, 2H), 1.79-1.90 (in, 2H).

The following examples in Table 5 were prepared using the procedures outlined in the synthesis of Example 77 with the appropriate substituted alcohol or INTERMEDIATE C in Step 1 and the appropriate INTERMEDIATE F in Step 2.

TABLE 5

| Ex | Structure | Name | MS (M + 1) |
|---|---|---|---|
| 78 | 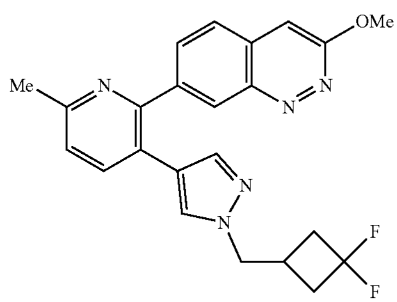 [SMILES: COc1cc2ccc(-c3nc(C)ccc3-c3cnn(CC4CC(F)(F)C4)c3)cc2nn1] | 7-(3-{1-[(3,3-difluorocyclobutyl)methyl]-1H-pyrazol-4-yl}-6-methylpyridin-2-yl)-3-methoxycinnoline | 422 |
| 79 | 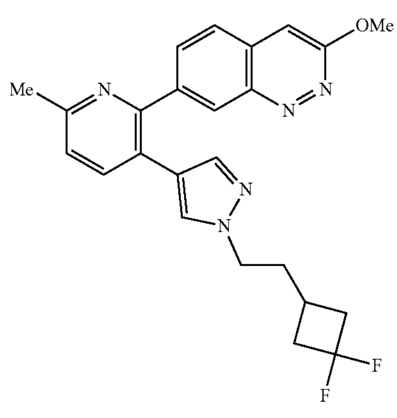 [SMILES: COc1cc2ccc(-c3nc(C)ccc3-c3cnn(CCC4CC(F)(F)C4)c3)cc2nn1] | 7-(3-{1-[2-(3,3-difluorocyclobutyl)ethyl]-1H-pyrazol-4-yl}-6-methylpyridin-2-yl)-3-methoxycinnoline | 436 |

TABLE 5-continued

| Ex | Structure | Name | MS (M + 1) |
|---|---|---|---|
| 80 | 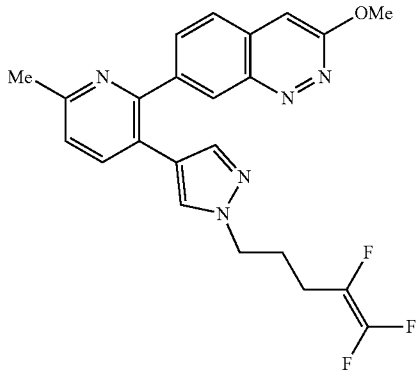 [SMILES: COc1cc2ccc(-c3nc(C)ccc3-c3cnn(CCCC(F)=C(F)F)c3)cc2nn1] | 3-methoxy-7-{6-methyl-3-[1-(4,5,5-trifluoropent-4-en-1-yl)-1H-pyrazol-4-yl]pyridin-2-yl}cinnoline | 440 |
| 81 | 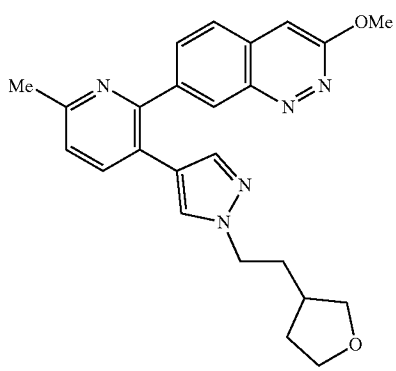 [SMILES: COc1cc2ccc(-c3nc(C)ccc3-c3cnn(CCC4CCOC4)c3)cc2nn1] | 3-methoxy-7-(6-methyl-3-{1-[2-(tetrahydrofuran-3-yl)ethyl]-1H-pyrazol-4-yl}pyridin-2-yl)cinnoline | 416 |
| 82 | 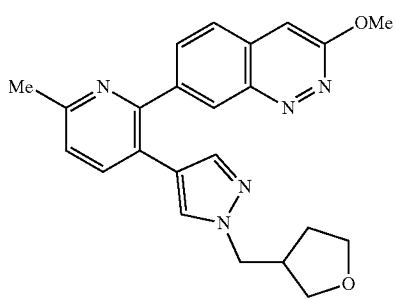 [SMILES: COc1cc2ccc(-c3nc(C)ccc3-c3cnn(CC4CCOC4)c3)cc2nn1] | 3-methoxy-7-{6-methyl-3-[1-(tetrahydrofuran-3-ylmethyl)-1H-pyrazol-4-yl]pyridin-2-yl}cinnoline | 402 |
| 83 | 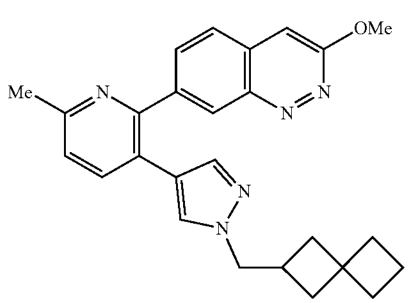 [SMILES: COc1cc2ccc(-c3nc(C)ccc3-c3cnn(CC4CC5(CCC5)C4)c3)cc2nn1] | 3-methoxy-7-{6-methyl-3-[1-(spiro[3.3]hept-2-ylmethyl)-1H-pyrazol-4-yl]pyridin-2-yl}cinnoline | 426 |

TABLE 5-continued

| Ex | Structure | Name | MS (M + 1) |
|---|---|---|---|
| 84 | 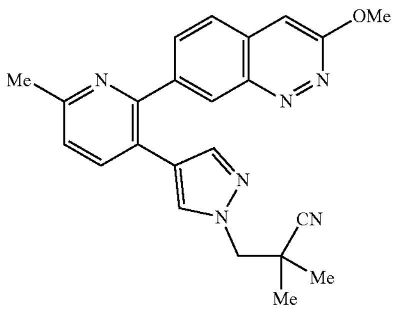 [SMILES: COc1cc2ccc(-c3nc(C)ccc3-c3cnn(CC(C)(C)C#N)c3)cc2nn1] | 3-{4-[2-(3-methoxycinnolin-7-yl)-6-methylpyridin-3-yl]-1H-pyrazol-1-yl}-2,2-dimethylpropanenitrile | 399 |
| 85 | 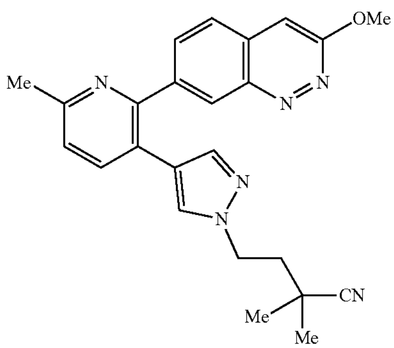 [SMILES: COc1cc2ccc(-c3nc(C)ccc3-c3cnn(CCC(C)(C)C#N)c3)cc2nn1] | 4-{4-[2-(3-methoxycinnolin-7-yl)-6-methylpyridin-3-yl]-1H-pyrazol-1-yl}-2,2-dimethylbutanenitrile | 413 |
| 86 | 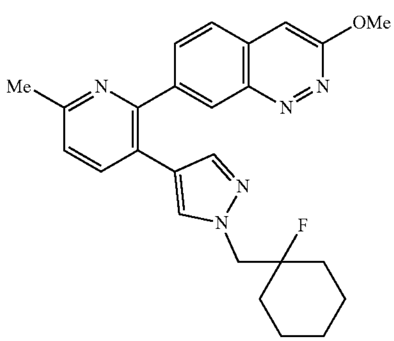 [SMILES: COc1cc2ccc(-c3nc(C)ccc3-c3cnn(CC4(F)CCCCC4)c3)cc2nn1] | 7-(3-{1-[(1-fluorocyclohexyl)methyl]-1H-pyrazol-4-yl}-6-methylpyridin-2-yl)-3-methoxycinnoline | 432 |
| 87 | 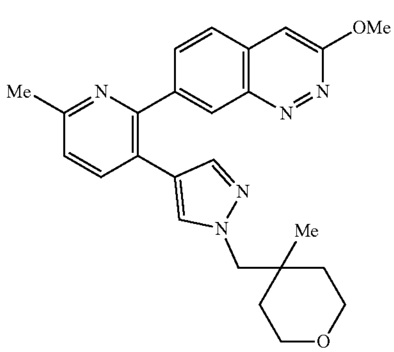 [SMILES: COc1cc2ccc(-c3nc(C)ccc3-c3cnn(CC4(C)CCOCC4)c3)cc2nn1] | 3-methoxy-7-(6-methyl-3-{1-[(4-methyltetrahydro-2H-pyran-4-yl)methyl]-1H-pyrazol-4-yl}pyridin-2-yl)cinnoline | 430 |

TABLE 5-continued

| Ex | Structure | Name | MS (M + 1) |
|---|---|---|---|
| 88 | 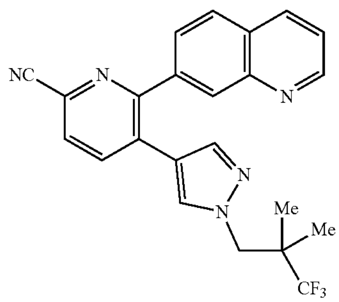 [SMILES: CC(C)(Cn1cc(-c2ccc(C#N)nc2-c2ccc3cccnc3c2)cn1)C(F)(F)F] | 6-quinolin-7-yl-5-[1-(3,3,3-trifluoro-2,2-dimethylpropyl)-1H-pyrazol-4-yl]pyridine-2-carbonitrile | 422 |
| 89 | 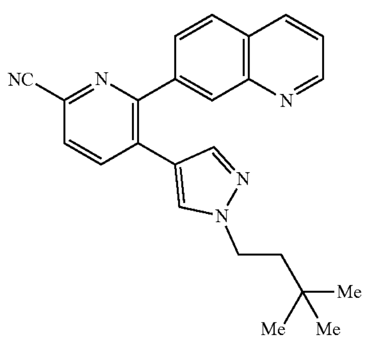 [SMILES: CC(C)(C)CCn1cc(-c2ccc(C#N)nc2-c2ccc3cccnc3c2)cn1] | 5-[1-(3,3-dimethylbutyl)-1H-pyrazol-4-yl]-6-quinolin-7-ylpyridine-2-carbonitrile | 382 |
| 90 | 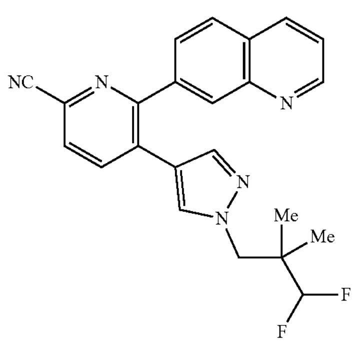 [SMILES: CC(C)(Cn1cc(-c2ccc(C#N)nc2-c2ccc3cccnc3c2)cn1)C(F)F] | 5-[1-(3,3-difluoro-2,2-dimethylpropyl)-1H-pyrazol-4-yl]-6-quinolin-7-ylpyridine-2-carbonitrile | 404 |
| 91 | 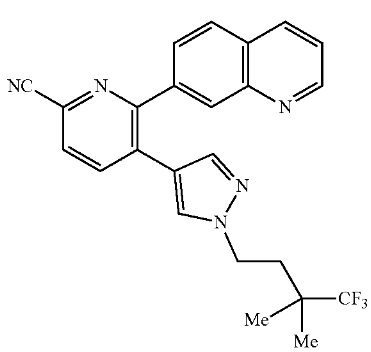 [SMILES: CC(C)(CCn1cc(-c2ccc(C#N)nc2-c2ccc3cccnc3c2)cn1)C(F)(F)F] | 6-quinolin-7-yl-5-[1-(4,4,4-trifluoro-3,3-dimethylbutyl)-1H-pyrazol-4-yl]pyridine-2-carbonitrile | 436 |

TABLE 5-continued

| Ex | Structure | Name | MS (M + 1) |
|---|---|---|---|
| 92 | 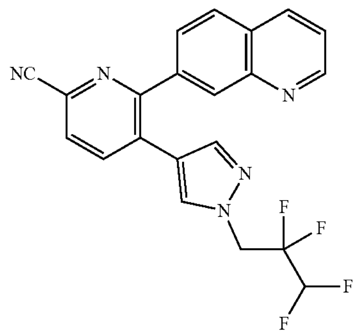 [SMILES: N#Cc1ccc(-c2cnn(CC(F)(F)C(F)F)c2)c(-c2ccc3cccnc3c2)n1] | 6-quinolin-7-yl-5-[1-(2,2,3,3-tetrahydropropyl)-1H-pyrazol-4-yl]pyridine-2-carbonitrile | 412 |
| 93 | 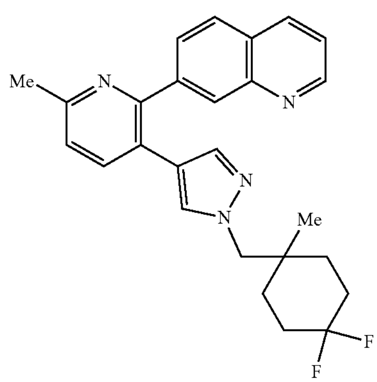 [SMILES: Cc1ccc(-c2cnn(CC3(C)CCC(F)(F)CC3)c2)c(-c2ccc3cccnc3c2)n1] | 7-(3-{1-[(4,4-difluoro-1-methylcyclohexyl)methyl]-1H-pyrazol-4-yl}-6-methylpyridin-2-yl)quinoline | 433 |

Example 94

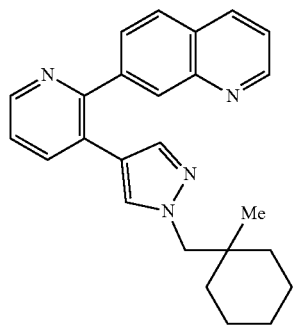 [SMILES: CC1(Cn2cc(-c3cccnc3-c3ccc4cccnc4c3)cn2)CCCCC1]

7-(3-{1-[(1-methylcyclohexyl)methyl]-1H-pyrazol-4-yl}pyridin-2-yl)quinoline

In a vial, 7-(3-(1H-pyrazol-4-yl)pyridin-2-yl)quinoline (INTERMEDIATE F7, 50 mg, 0.18 mmol), diisopropyl azodicarboxylate (74 mg, 0.37 mmol), triphenylphosphine (96 mg, 0.37 mmol) and (1-methylcyclohexyl)methanol (47 mg, 0.37 mmol) were charged with tetrahydrofuran (1 mL). The reaction mixture was heated to 65° C. under an atmosphere of nitrogen for 18 hours. It was diluted with ethyl acetate (2 mL), washed with saturated aqueous sodium hydrogencarbonate (1 mL) and brine (1 mL), and concentrated in vacuo. Purification by reverse phase HPLC (acetonitrile/water with 0.05% ammonium hydroxide) afforded the title compound. LC/MS=383 [M+1]. $^1$H-NMR (DMSO-$d_6$, 500 MHz) δ 8.90 (d, J=3.0 Hz, 1H), 8.61 (d, J=4.5 Hz, 1H), 8.40 (d, J=8.1 Hz, 1H), 8.00 (s, 1H), 7.91-7.98 (m, 2H), 7.53-7.62 (m, 2H), 7.48 (dd, J=4.8, 7.8 Hz, 1H), 7.40 (s, 1H), 7.18 (s, 1H), 3.76 (s, 2H), 0.88-1.49 (m, 10H), 0.60 (s, 3H).

The following examples in Table 6 were prepared using the procedures outlined in the synthesis of Example 94 with the appropriate alcohol and the appropriate INTERMEDIATE F.

TABLE 6

| Ex | Structure | Name | MS (M + 1) |
|---|---|---|---|
| 95 | 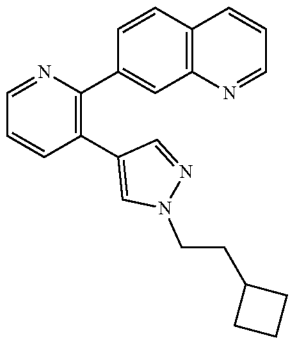 [SMILES: c1cnc(-c2ccc3cccnc3c2)c(-c2cnn(CCC3CCC3)c2)c1] | 7-{3-[1-(2-cyclobutylethyl)-1H-pyrazol-4-yl]pyridin-2-yl}quinoline | 355 |
| 96 | 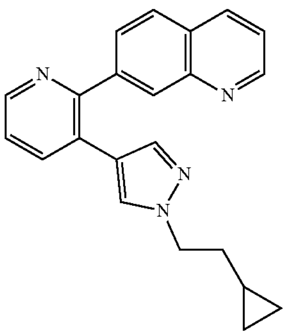 [SMILES: c1cnc(-c2ccc3cccnc3c2)c(-c2cnn(CCC3CC3)c2)c1] | 7-{3-[1-(2-cyclopropylethyl)-1H-pyrazol-4-yl]pyridin-2-yl}quinoline | 341 |
| 97 | 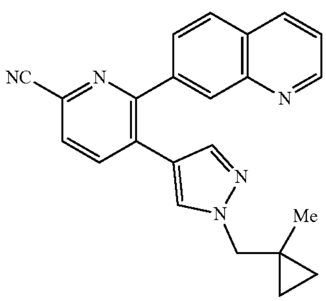 [SMILES: CC1(Cn2cc(-c3ccc(C#N)nc3-c3ccc4cccnc4c3)cn2)CC1] | 5-{1-[(1-methylcyclopropyl)methyl]-1H-pyrazol-4-yl}-6-quinolin-7-ylpyridine-2-carbonitrile | 366 |

Examples 98 and 99

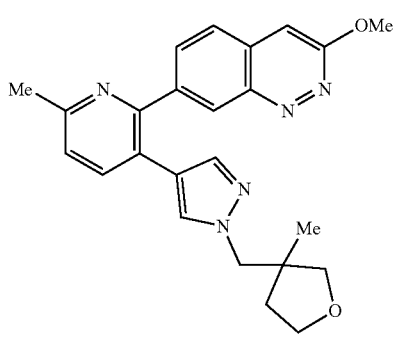 [SMILES: COc1cc2ccc(-c3nc(C)ccc3-c3cnn(CC4(C)CCOC4)c3)cc2nn1]

3-methoxy-7-(6-methyl-3-{1-[(3-methyltetrahydrofuran-3-yl)methyl]-1H-pyrazol-4-yl}pyridin-2-yl)cinnoline Step 1: diiodotriphenylphosphorane To a dichloromethane (500 mL) solution of iodine (97 g, 381 mmol) at 0° C. was slowly added triphenylphosphine (100 g, 381 mmol) portionwise. The reaction was stirred at 0° C. for 2 hours. The reaction mixture was concentrated in vacuo, and the residue was washed with dry diethyl ether to afford the title compound as the crude product, which was used in the subsequent reaction without further purification.

Step 2: 3-(iodomethyl)-3-methyltetrahydrofuran

To a dichloromethane (10 mL) solution of (3-methyltetrahydrofuran-3-yl)methanol (INTERMEDIATE C15, 2.00 g, 17.2 mmol) at −78° C. was added 1-methylimidazole (2.74 mL, 34.4 mmol) and diiodotriphenylphosphorane (12.4 g, 24.1 mmol). After addition, the reaction mixture was slowly warmed to room temperature and stirred for 48 hours. It was diluted with water (20 mL). The aqueous layer was extracted with diethyl ether (20 mL×3), and the combined organic extracts were dried (magnesium sulfate), filtered, and concentrated in vacuo. Purification by column chromatography over silica gel, eluting with hexanes/ethyl acetate, afforded the title compound. $^1$H-NMR (CDCl$_3$, 500 MHz) δ 3.85-3.97 (m, 2H), 3.67 (d, J=8.7 Hz, 1H), 3.51 (d, J=8.7 Hz, 1H), 3.30 (s, 2H), 1.94 (td, J=7.4, 14.2 Hz, 1H), 1.81 (td, J=7.0, 13.5 Hz, 1H), 1.24 (s, 3H).

Step 3: 3-methoxy-7-(6-methyl-3-{1-[(3-methyltetrahydrofuran-3-yl)methyl]-1H-pyrazol-4-yl}pyridin-2-yl)cinnoline To a mixture of 3-methoxy-7-(6-methyl-3-(1H-pyrazol-4-yl)pyridin-2-yl)cinnoline (INTERMEDIATE F1, 185 mg, 0.583 mmol), 3-(iodomethyl)-3-methyl tetrahydrofuran (132 mg, 0.583 mmol) and cesium carbonate (475 mg, 1.46 mmol) was charged N,N-dimethylformamide (5 mL). The reaction mixture was stirred at 100° C. for 3 hours, cooled down and diluted with water (20 mL). The aqueous layer was extracted with ethyl acetate (20 mL×3), and the combined organic extracts were dried (magnesium sulfate), filtered, and concentrated in vacuo. Purification by column chromatography over silica gel, eluting with hexanes/ethyl acetate, afforded the title compound. LC/MS=416 [M+1]. $^1$H-NMR (CDCl$_3$, 500 MHz) δ 8.50 (s, 1H), 7.70 (d, J=7.9 Hz, 1H), 7.60-7.67 (m, 2H), 7.38 (s, 1H), 7.20-7.25 (m, 2H), 6.94 (s, 1H), 4.30 (s, 3H), 3.93 (d, J=14.2 Hz, 1H), 3.89 (d, J=14.2 Hz, 1H), 3.72-3.81 (m, 2H), 3.57 (d, J=8.7 Hz, 1H), 3.27 (d, J=8.7 Hz, 1H), 2.66 (s, 3H), 1.76 (td, J=7.7, 12.6 Hz, 1H), 1.51 (ddd, J=6.2, 7.8, 12.6 Hz, 1H), 0.87 (s, 3H). Chiral resolution of the two enantiomers was achieved by chiral preparative SFC (AD column; methanol (0.200 ammonium hydroxide) 35 mL/min; supercritical carbon dioxide 35 mL/min) to afford the faster-eluting enantiomer EXAMPLE 98 and the slower-eluting enantiomer EXAMPLE 99.

The following examples in Table 7 were prepared using the procedures outlined in the synthesis of Examples 98 and 99 with the appropriate alkyl iodide or bromide and the appropriate INTERMEDIATE F in Step 3.

TABLE 7

| Ex | Structure | Name | MS (M + 1) |
|---|---|---|---|
| 100 | 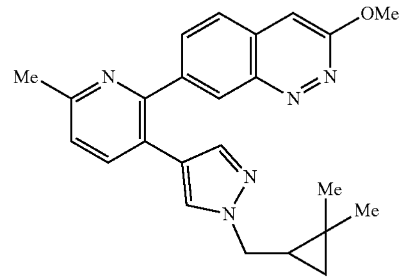 [SMILES: COc1cc2ccc(-c3nc(C#N)ccc3-c3cnn(CC4CC4(C)C)c3)cc2nn1] | 7-(3-{1-[(2,2-dimethylcyclopropyl)methyl]-1H-pyrazol-4-yl}-6-methylpyridin-2-yl)-3-methoxycinnoline | 400 |
| 101 | 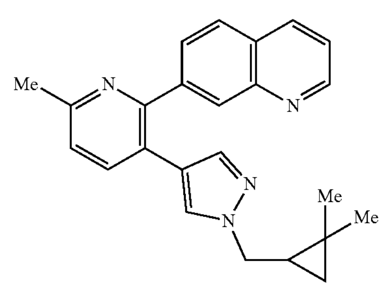 [SMILES: CC1(C)CC1Cn1cc(-c2ccc(C#N)nc2-c2ccc3cccnc3c2)cn1] | 7-(3-{1-[(2,2-dimethylcyclopropyl)methyl]-1H-pyrazol-4-yl}-6-methylpyridin-2-yl)quinoline | 369 |
| 102 | 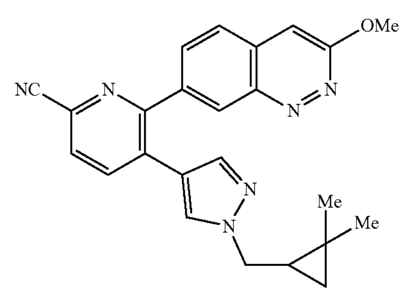 | 5-{1-[(2,2-dimethylcyclopropyl)methyl]-1H-pyrazol-4-yl}-6-(3-methoxycinnolin-7-yl)pyridine-2-carbonitrile | 411 |

TABLE 7-continued

| Ex | Structure | Name | MS (M + 1) |
|---|---|---|---|
| 103 | 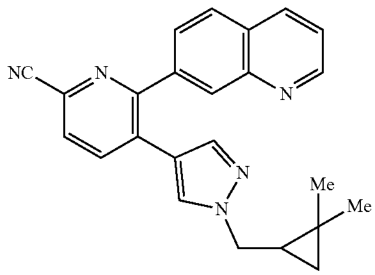 | 5-{1-[(2,2-dimethylcyclopropyl)methyl]-1H-pyrazol-4-yl}-6-quinolin-7-ylpyridine-2-carbonitrile | 380 |
| 104 | 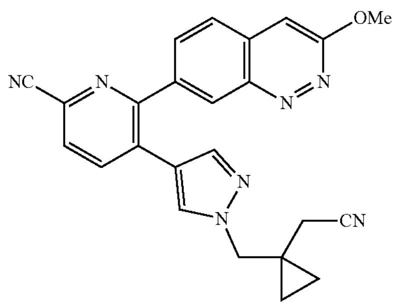 [SMILES: COc1cc2ccc(-c3nc(C#N)ccc3-c3cnn(CC4(CC#N)CC4)c3)cc2nn1] | 5-(1-{[1-(cyanomethyl)cyclopropyl]methyl}-1H-pyrazol-4-yl)-6-(3-methoxycinnolin-7-yl)pyridine-2-carbonitrile | 422 |
| 105 | 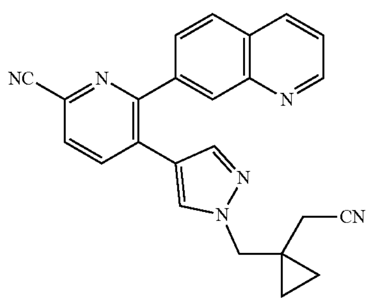 [SMILES: N#CCC1(Cn2cc(-c3ccc(C#N)nc3-c3ccc4cccnc4c3)cn2)CC1] | 5-(1-{[1-(cyanomethyl)cyclopropyl]methyl}-1H-pyrazol-4-yl)-6-quinolin-7-ylpyridine-2-carbonitrile | 391 |
| 106 | 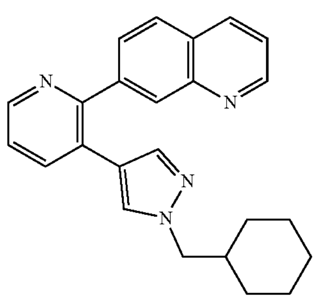 [SMILES: c1cnc(-c2ccc3cccnc3c2)c(-c2cnn(CC3CCCCC3)c2)c1] | 7-{3-[1-(cyclohexylmethyl)-1H-pyrazol-4-yl]pyridin-2-yl}quinoline | 369 |
| 107 | 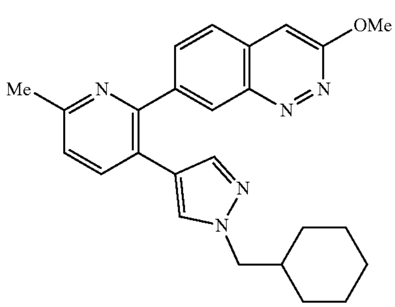 [SMILES: COc1cc2ccc(-c3nc(C)ccc3-c3cnn(CC4CCCCC4)c3)cc2nn1] | 7-{3-[1-(cyclohexylmethyl)-1H-pyrazol-4-yl]-6-methylpyridin-2-yl}-3-methoxycinnoline | 414 |

TABLE 7-continued

| Ex | Structure | Name | MS (M + 1) |
|---|---|---|---|
| 108 | 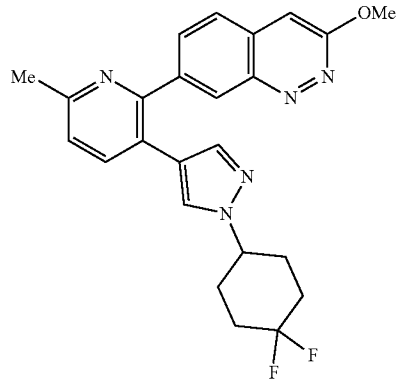 [SMILES: COc1cc2ccc(-c3nc(C)ccc3-c3cnn(C4CCC(F)(F)CC4)c3)cc2nn1] | 7-{3-[1-(4,4-difluorocyclohexyl)-1H-pyrazol-4-yl]-6-methylpyridin-2-yl}-3-methoxycinnoline | 436 |
| 109 | 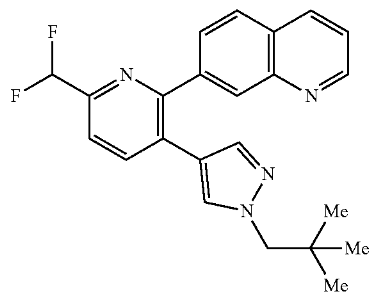 [SMILES: CC(C)(C)Cn1cc(-c2ccc(C(F)F)nc2-c2ccc3cccnc3c2)cn1] | 7-{6-(difluoromethyl)-3-[1-(2,2-dimethylpropyl)-1H-pyrazol-4-yl]pyridin-2-yl}quinoline | 393 |
| 110 | 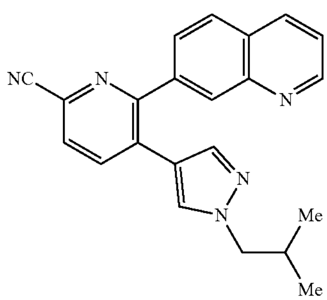 [SMILES: CC(C)Cn1cc(-c2ccc(C#N)nc2-c2ccc3cccnc3c2)cn1] | 5-[1-(2-methylpropyl)-1H-pyrazol-4-yl]-6-quinolin-7-ylpyridine-2-carbonitrile | 354 |

Example 111

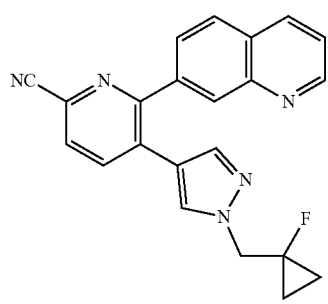

5-{1-[(1-fluorocyclopropyl)methyl]-1H-pyrazol-4-yl}-6-quinolin-7-ylpyridine-2-carbonitrile Step 1: (1-fluorocyclopropyl)methanol To a tetrahydrofuran (3.0 mL) solution of 1-fluorocyclopropanecarboxylic acid (200 mg, 1.92 mmol) at 0° C. was added a 10 M tetrahydrofuran solution of borane dimethyl sulfide complex (0.77 mL, 7.7 mmol). The reaction mixture was stirred at 25° C. for 16 hours. It was quenched with methanol (3 mL) and concentrated in vacuo to afford the title compound as the crude product, which was used in the subsequent reaction without further purification. $^1$H-NMR (CDCl$_3$, 400 MHz) δ 3.86 (d, J=22.0 Hz, 2H), 1.13 (d, J=18.8 Hz, 2H), 0.71 (d, J=7.6 Hz, 2H).

Step 2: (1-fluorocyclopropyl)methyl methanesulfonate

To a dichloromethane (4 mL) solution of (1-fluorocyclopropyl)methanol (100 mg, 1.11 mmol) at 0° C. was added triethylamine (0.62 mL, 4.44 mmol), followed by a dropwise addition of methanesulfonyl chloride (100 mg, 0.873 mmol).

The reaction mixture was stirred at 25° C. for 3 hours and quenched with saturated aqueous sodium hydrogencarbonate (5 mL). The aqueous layer was extracted with dichloromethane (10 mL×3), and the combined organic extracts were washed with brine, dried (sodium sulfate), filtered, and concentrated in vacuo to afford the title compound as the crude product. It was used in the subsequent reaction without further purification. $^1$H-NMR (CDCl$_3$, 400 MHz) δ 4.48 (d, J=22.0 Hz, 2H), 3.09 (s, 3H), 1.15-1.25 (m, 2H), 0.80-0.90 (m, 2H).

Step 3: 5-{1-[(1-fluorocyclopropyl)methyl]-1H-pyrazol-4-yl}-6-quinolin-7-ylpyridine-2-carbonitrile The title compound was made by following the procedures described in Step 3 for EXAMPLES 98 and 99, substituting 5-(1H-pyrazol-4-yl)-6-(quinolin-7-yl)picolinonitrile (INTERMEDIATE F2) for 3-methoxy-7-(6-methyl-3-(1H-pyrazol-4-yl)pyridin-2-yl)cinnoline and 1-fluorocyclopropyl)methyl methanesulfonate for 3-(iodomethyl)-3-methyltetrahydrofuran. LC/MS=370 [M+1]. $^1$H-NMR (CD$_3$OD, 400 MHz) δ 9.25 (s, 1H), 9.00 (d, J=4.8 Hz, 1H), 8.31 (s, 1H), 8.15-8.30 (m, 2H), 7.92-7.98 (m, 2H), 7.89 (d, J=4.8 Hz, 1H), 7.51 (s, 1H), 7.44 (s, 1H), 4.39 (d, J=21.2 Hz, 2H), 0.95 (d, J=16.8 Hz, 2H), 0.70-0.80 (m, 2H).

Example 112

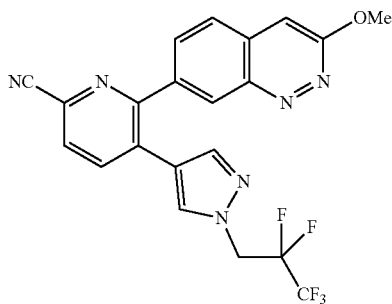 [SMILES: COc1cc2ccc(-c3nc(C#N)ccc3-c3cnn(CC(F)(F)C(F)(F)F)c3)cc2nn1]

6-(3-methoxycinnolin-7-yl)-5-[1-(2,2,3,3,3-pentafluoropropyl)-1H-pyrazol-4-yl]pyridine-2-carbonitrile Step 1: 2,2,3,3,3-pentafluoropropyl trifluoromethanesulfonate To a dichloromethane (5 mL) solution of 2,2,3,3,3-pentafluoropropan-1-ol (500 mg, 3.30 mmol) and N,N-diisopropylethylamine (1.11 g, 3.96 mmol) at −78° C. was added trifluoromethanesulfonic anhydride (1.11 g, 8.58 mmol). The reaction mixture was stirred at −78° C. for 30 minutes, then at −30° C. for 30 minutes. It was quenched with water (5 mL), and the aqueous layer was extracted with dichloromethane (5 mL×3). The combined organic extracts were washed with 1.0 N hydrochloric acid (10 mL), water (10 mL), dried (sodium sulfate), filtered, and concentrated in vacuo to afford the title compound as the crude product, which was used in the subsequent reaction without further purification.

Step 2: 6-(3-methoxycinnoline-7-yl)-5-[1-(2,2,3,3,3-pentafluoropropyl)-1H-pyrazol-4-yl]pyridine-2-carbonitrile The title compound was made by following the procedures described in Step 3 for EXAMPLES 98 and 99, substituting 6-(3-methoxycinnolin-7-yl)-5-(1H-pyrazol-4-yl)picolinonitrile (INTERMEDIATE F3) for 3-methoxy-7-(6-methyl-3-(1H-pyrazol-4-yl)pyridin-2-yl)cinnoline and 2,2,3,3,3-pentafluoropropyl trifluoromethanesulfonate for 3-(iodomethyl)-3-methyltetrahydrofuran. LC/MS=461 [M+1]. $^1$H-NMR (CD$_3$OD, 400 MHz) δ 8.40 (s, 1H), 8.19 (d, J=7.8 Hz, 1H), 7.96 (d, J=8.2 Hz, 1H), 7.89 (d, J=9.0 Hz, 1H), 7.63-7.71 (m, 2H), 7.53 (s, 1H), 7.43 (s, 1H), 4.95 (s, 2H), 4.25 (s, 3H).

Example 113

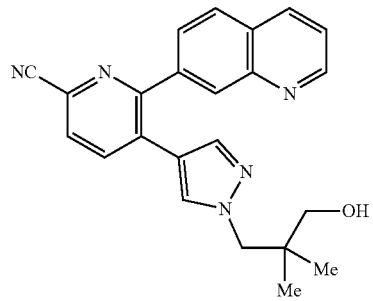 [SMILES: CC(C)(CO)Cn1cc(-c2ccc(C#N)nc2-c2ccc3cccnc3c2)cn1]

5-[1-(3-hydroxy-2,2-dimethylpropyl)-1H-pyrazol-4-yl]-6-quinolin-7-ylpyridine-2-carbonitrile Step 1: 5-(1-(3-((tert-butyldiphenylsilyl)oxy)-2,2-dimethylpropyl)-1H-pyrazol-4-yl)-6-(quinolin-7-yl)picolinonitrile The title compound was made by following the procedures described in EXAMPLE 94, substituting 5-(1H-pyrazol-4-yl)-6-(quinolin-7-yl)picolinonitrile (INTERMEDIATE F2) for 7-(3-(1H-pyrazol-4-yl)pyridin-2-yl)quinoline and 3-((tert-butyldiphenylsilyl)oxy)-2,2-dimethylpropan-1-ol for (1-methylcyclohexyl)methanol. LC/MS=622 [M+1].

Step 2: 5-[1-(3-hydroxy-2,2-dimethylpropyl)-1H-pyrazol-4-yl]-6-quinolin-7-ylpyridine-2-carbonitrile To a tetrahydrofuran (2 mL) solution of 5-(1-(3-((tert-butyldiphenylsilyl)oxy)-2,2-dimethylpropyl)-1H-pyrazol-4-yl)-6-(quinolin-7-yl)picolinonitrile (100 mg, 0.16 mmol) at 0° C. was added a 1.0 M tetrahydrofuran solution of tetrabutylammonium fluoride (0.32 mL, 0.32 mmol). The reaction mixture was stirred at 15° C. for 3 hours and concentrated in vacuo. Purification by reverse phase HPLC (acetonitrile/water with 0.05% trifluoroacetic acid) afforded the title compound as the trifluoroacetate salt. LC/MS=384 [M+1]. $^1$H-NMR (CD$_3$OD, 400 MHz) δ 9.04 (d, J=4.0 Hz, 1H), 8.78 (d, J=8.0 Hz, 1H), 8.10-8.26 (m, 3H), 7.94 (d, J=8.0 Hz, 1H), 7.73-7.87 (m, 2H), 7.39 (s, 1H), 7.35 (s, 1H), 3.86 (s, 2H), 3.02 (s, 2H), 0.68 (s, 6H).

Example 114

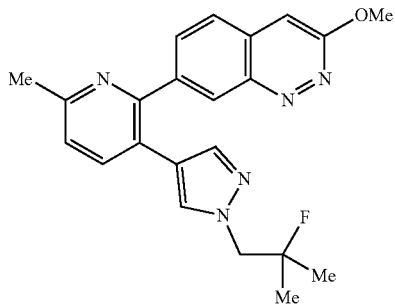

7-{3-[1-(2-fluoro-2-methylpropyl)-1H-pyrazol-4-yl]-6-methylpyridin-2-yl}-3-methoxycinnoline Step 1: 1-{4-[2-(3-methoxycinnoline-7-yl)-6-methylpyridin-3-yl]-1H-pyrazol-1-yl}-2-methylpropan-2-ol In a 30-mL vial, an acetonitrile solution (5 mL) of 3-methoxy-7-(6-methyl-3-(1H-pyrazol-4-yl)pyridin-2-yl)cinnoline (50 mg, 0.158 mmol) was charged with 2,2-dimethyloxirane (170 mg, 2.36 mmol), followed by cesium carbonate (103 mg, 0.315 mmol). The vial was sealed and heated to 90° C. for 4 hours. It was cooled to room temperature, diluted with dichloromethane (15 mL), filtered and concentrated in vacuo. The residue was dissolved in ethyl acetate (40 mL), dried (sodium sulfate), filtered and concentrated in vacuo to afford the title compound as the crude product, which was used in the subsequent reaction without further purification. LC/MS=390 [M+1]. $^1$H-NMR (CDCl$_3$, 400 MHz) δ 8.50 (s, 1H), 7.70 (d, J=8.0 Hz, 1H), 7.62-7.66 (m, 2H), 7.39 (s, 1H), 7.20-7.30 (m, 2H), 7.09 (s, 1H), 4.30 (s, 3H), 3.90 (s, 2H), 2.66 (s, 3H), 1.05 (s, 6H).

Step 2: 7-{3-[1-(2-fluoro-2-methylpropyl)-1H-pyrazol-4-yl]-6-methylpyridin-2-yl}-3-methoxycinnoline To a dichloromethane (1.5 mL) solution of 1-{4-[2-(3-methoxycinnolin-7-yl)-6-methylpyridin-3-yl]-1H-pyrazol-1-yl}-2-methylpropan-2-ol (20 mg, 0.051 mmol) at 0° C. was added (diethylamino)sulfur trifluoride (0.10 mL, 0.76 mmol) dropwise. The reaction mixture was stirred at 20° C. for 1 hour, quenched by water and concentrated in vacuo. Purification by reverse phase HPLC (acetonitrile/water with 0.05% trifluoroacetic acid) afforded the title compound as the trifluoroacetate salt. LC/MS=392 [M+1]. $^1$H-NMR (CD$_3$OD, 400 MHz) δ 8.29 (s, 1H), 7.89 (d, J=8.0 Hz, 1H), 7.84 (d, J=8.4 Hz, 1H), 7.64 (d, J=8.4 Hz, 1H), 7.59 (s, 1H), 7.39 (d, J=8.0 Hz, 1H), 7.33 (s, 1H), 7.29 (s, 1H), 4.23 (s, 3H), 4.12 (d, J=20.8 Hz, 2H), 2.61 (s, 3H), 1.12 (d, J=21.2 Hz, 6H).

Example 115

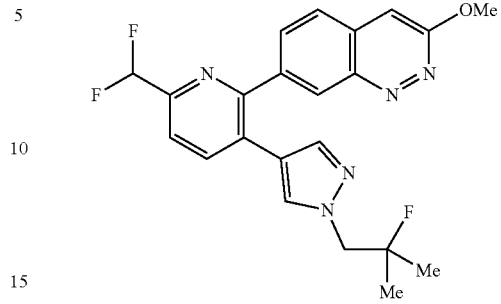

7-{6-(difluoromethyl)-3-[1-(2-fluoro-2-methylpropyl)-1H-pyrazol-4-yl]pyridin-2-yl}-3-methoxycinnoline The title compound was made by following the procedures described in EXAMPLE 114, substituting 7-(6-(difluoromethyl)-3-(1H-pyrazol-4-yl)pyridin-2-yl)-3-methoxycinnoline (INTERMEDIATE F5) for 3-methoxy-7-(6-methyl-3-(1H-pyrazol-4-yl)pyridin-2-yl)cinnoline. LC/MS=428 [M+1]. $^1$H-NMR (CD$_3$OD, 400 MHz) δ 8.35 (s, 1H), 8.13 (d, J=8.0 Hz, 1H), 7.85 (d, J=8.8 Hz, 1H), 7.77 (d, J=8.0 Hz, 1H), 7.71 (d, J=8.8 Hz, 1H), 7.58 (s, 1H), 7.38-7.46 (m, 2H), 6.64 (t, J=55.2 Hz, 1H), 4.22 (s, 3H), 4.16 (d, J=20.8 Hz, 2H), 1.15 (d, J=21.2 Hz, 6H).

Example 116

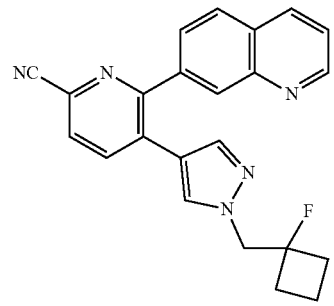 [SMILES: N#Cc1ccc(-c2cnn(CC3(F)CCC3)c2)c(-c2ccc3cccnc3c2)n1]

5-{1-[(1-fluorocyclobutyl)methyl]-1H-pyrazol-4-yl}-6-quinolin-7-ylpyridine-2-carbonitrile Step 1: 5-(1-((1-hydroxycyclobutyl)methyl)-1H-pyrazol-4-yl)-6-(quinolin-7-yl)picolinonitrile The title compound was made by following the procedures described in EXAMPLE 77, substituting 1-(hydroxymethyl)cyclobutan-1-ol for 4,4,4-trifluorobutan-1-ol in Step 1 and 5-(1H-pyrazol-4-yl)-6-(quinolin-7-yl)picolinonitrile (INTERMEDIATE F2) for 3-methoxy-7-(6-methyl-3-(1H-pyrazol-4-yl)pyridin-2-yl)cinnoline in Step 2. LC/MS=382 [M+1]. $^1$H-NMR (CD$_3$OD, 400 MHz) δ 8.85 (s, 1H), 8.39 (d, J=8.4 Hz, 1H), 8.10-8.13 (m, 2H), 7.95 (d, J=8.0 Hz, 1H), 7.87 (d, J=8.0 Hz, 1H), 7.55-7.65 (m, 2H), 7.46 (s, 1H), 7.27 (s, 1H), 4.06 (s, 2H), 1.80-2.00 (m, 4H), 1.60-1.70 (m, 1H), 1.40-1.50 (m, 1H).

Step 2: 5-{1-[(1-fluorocyclobutyl)methyl]-1H-pyrazol-4-yl}-6-quinolin-7-ylpyridine-2-carbonitrile The title compound was made by following the procedures described in EXAMPLE 114 STEP 2, substituting 5-(1-((1-hydroxycyclobutyl)methyl)-1H-pyrazol-4-yl)-6-(quinolin-7-yl)picolinonitrile for 1-{4-[2-(3-methoxycinnolin-7-yl)-6-methylpyridin-3-yl]-1H-pyrazol-1-yl}-2-methylpropan-2-ol. LC/MS=384 [M+1]. $^1$H-NMR (CD$_3$OD, 400 MHz) δ 9.13 (s, 1H), 8.95 (d, J=8.4 Hz, 1H), 8.22 (s, 1H), 8.15-8.25 (m, 2H), 7.85-7.90 (m, 2H), 7.80 (d, J=8.4 Hz, 1H), 7.43 (s, 1H), 7.40 (s, 1H), 4.30 (d, J=17.2 Hz, 2H), 2.06-2.13 (m, 4H), 1.75-1.80 (m, 1H), 1.47-1.54 (m, 1H).

Example 117

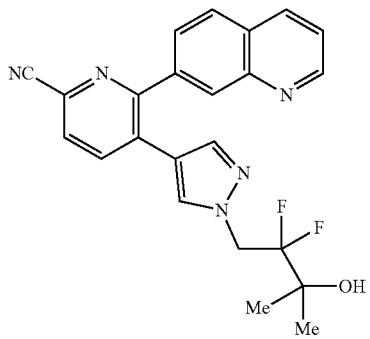 [SMILES: CC(C)(O)C(F)(F)Cn1cc(-c2ccc(C#N)nc2-c2ccc3cccnc3c2)cn1]

5-[1-(2,2-difluoro-3-hydroxy-3-methylbutyl)-1H-pyrazol-4-yl]-6-quinolin-7-ylpyridine-2-carbonitrile Step 1: ethyl 3-(4-(6-cyano-2-(quinolin-7-yl)pyridin-3-yl)-1H-pyrazol-1-yl)-2,2-difluoropropanoate The title compound was made by following the procedures described in EXAMPLE 94, substituting 5-(1H-pyrazol-4-yl)-6-(quinolin-7-yl)picolinonitrile (INTERMEDIATE F2) for 7-(3-(1H-pyrazol-4-yl)pyridin-2-yl)quinoline and ethyl 2,2-difluoro-3-hydroxypropanoate for (1-methylcyclohexyl)methanol. LC/MS=434 [M+1].

Step 2: 5-[1-(2,2-difluoro-3-hydroxy-3-methylbutyl)-1H-pyrazol-4-yl]-6-quinolin-7-ylpyridine-2-carbonitrile To a tetrahydrofuran (2 mL) solution of ethyl 3-(4-(6-cyano-2-(quinolin-7-yl)pyridin-3-yl)-1H-pyrazol-1-yl)-2,2-difluoropropanoate (60 mg, 0.032 mmol) at 0° C. was added 3.0 M tetrahydrofuran solution of methylmagnesium chloride (0.05 mL, 0.150 mmol). The reaction mixture was stirred at 0° C. for 1 hour and quenched with saturated aqueous ammonium chloride solution (10 mL). The aqueous layer was extracted with ethyl acetate (20 mL), and the combined organic extracts were concentrated. Purification by reverse phase HPLC (acetonitrile/water with 0.05% trifluoroacetic acid) afforded the title compound as the trifluoroacetate salt. LC/MS=420 [M+1]. $^1$H-NMR (CD$_3$OD, 400 MHz) δ 9.05 (d, J=4.0 Hz, 1H), 8.81 (d, J=8.0 Hz, 1H), 8.13-8.26 (m, 3H), 7.95 (d, J=8.0 Hz, 1H), 7.77-7.88 (m, 2H), 7.47 (s, 1H), 7.40 (s, 1H), 4.60 (t, J=16.0 Hz, 2H), 1.19 (s, 6H).

ASSAY PROTOCOL

The utility of the compounds as M4 muscarinic receptor allosteric modulators may be demonstrated by methodology known in the art, including by the assay described herein. CHO-K1 cells stably transfected with human M4 receptor and chimeric G-protein Gαqi5 are thawed from liquid N$_2$ storage, resuspended in growth medium, plated in black, clear bottom 384 well plates, and incubated 16-20 hours at 37° C., 5% CO$_2$. On the day of assay, growth medium is removed, the cells are washed 2 times with wash buffer, and cells are incubated in dye loading buffer at 37° C., 5% CO$_2$ for ~1 hour. Following dye loading the cell plates are placed in a FLIPR Tetra instrument and while monitoring dye fluorescence (excitation 470-495 nM/emission 515-575 nM), 10 uL of test substance at increasing concentrations is added, and fluorescence values are recorded for 4 min. Next, 10 uL of acetylcholine is added (final concentration calculated so as to achieve 20% of the maximum acetycholine response), and the fluorescence reading is continued for 3.5 min. In some cases, a third addition of acetylcholine (final concentration calculated to achieve 70% of the maximal acetylcholine response) is performed.

The following table shows representative data for the compounds of the Examples as modulators of the M4 muscarinic acetylcholine receptor as determined by the assays described herein. Such results are indicative of the intrinsic activity of the compounds for use as allosteric modulators of the M4 muscarinic acetylcholine receptor.

TABLE 8

| Example | M4PAM Hu IP (nM) | Example | M4PAM IP (nM) |
| --- | --- | --- | --- |
| 1 | 22 | 61 | 26 |
| 2 | 70 | 62 | 84 |
| 3 | 57 | 63 | 26 |
| 4 | 91 | 64 | 295 |
| 5 | 93 | 65 | 95 |
| 6 | 19 | 66 | 24 |
| 7 | 137 | 67 | 121 |
| 8 | 72 | 68 | 118 |
| 9 | 21 | 69 | 185 |
| 10 | 20 | 70 | 233 |
| 11 | 89 | 71 | 222 |
| 12 | 80 | 72 | 191 |
| 13 | 37 | 73 | 140 |
| 14 | 20 | 74 | 39 |
| 15 | 14 | 75 | 123 |
| 16 | 124 | 76 | 63 |
| 17 | 56 | 77 | 271 |
| 18 | 88 | 78 | 190 |
| 19 | 43 | 79 | 166 |
| 20 | 92 | 80 | 154 |
| 21 | 62 | 81 | 228 |
| 22 | 16 | 82 | 180 |
| 23 | 111 | 83 | 99 |
| 24 | 151 | 84 | 198 |
| 25 | 46 | 85 | 199 |
| 26 | 70 | 86 | 69 |
| 27 | 33 | 87 | 63 |
| 28 | 44 | 88 | 44 |
| 29 | 72 | 89 | 52 |
| 30 | 143 | 90 | 27 |
| 31 | 76 | 91 | 190 |
| 32 | 113 | 92 | 131 |
| 33 | 84 | 93 | 24 |
| 34 | 141 | 94 | 52 |

TABLE 8-continued

| Example | M4PAM Hu IP (nM) | Example | M4PAM IP (nM) |
|---|---|---|---|
| 35 | 187 | 95 | 158 |
| 36 | 14 | 96 | 239 |
| 37 | 25 | 97 | 87 |
| 38 | 41 | 98 | 57 |
| 39 | 92 | 99 | 169 |
| 40 | 208 | 100 | 81 |
| 41 | 39 | 101 | 100 |
| 42 | 47 | 102 | 91 |
| 43 | 112 | 103 | 45 |
| 44 | 61 | 104 | 154 |
| 45 | 60 | 105 | 120 |
| 46 | 169 | 106 | 93 |
| 47 | 88 | 107 | 16 |
| 48 | 220 | 108 | 142 |
| 49 | 84 | 109 | 48 |
| 50 | 188 | 110 | 129 |
| 51 | 414 | 111 | 110 |
| 52 | 145 | 112 | 138 |
| 53 | 131 | 113 | 139 |
| 54 | 53 | 114 | 191 |
| 55 | 108 | 115 | 190 |
| 56 | 275 | 116 | 39 |
| 57 | 243 | 117 | 104 |
| 58 | 51 | | |
| 59 | 57 | | |
| 60 | 181 | | |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of the formula I:

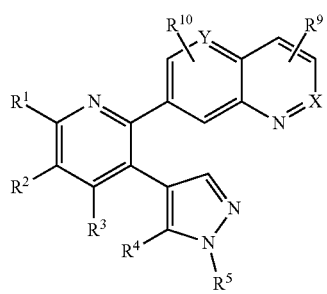

I wherein:
X is —N= or —C($R^8$)=;
Y is —N= or —C($R^{11}$)=;
$R^1$ is selected from:
(1) hydrogen,
(2) halogen,
(3) —CN,
(4) —$C_{1-6}$alkyl, which is unsubstituted or substituted with a hydroxy, pyrazolyl, dihydropyranyl, or 1-3 fluoro,
(5) —O—$C_{1-6}$alkyl, which is unsubstituted or substituted with a hydroxy, or 1-3 fluoro,
(6) cyclopropyl,
(7) —C=$CH_2$,
(8) —C≡CH,
(9) -pyrazolyl, which is unsubstituted or substituted with —$C_{1-6}$alkyl, and
(10) dihydropyranyl;

$R^2$ is selected from:
(1) hydrogen,
(2) halogen,
(3) —$C_{1-6}$alkyl,
(4) —CN,
(5) —$OC_{1-6}$alkyl, and
(6) —$SC_{1-6}$alkyl;

$R^3$ is selected from:
(1) hydrogen,
(2) chloro,
(3) —$C_{1-6}$alkyl, and
(4) —$OC_{1-6}$alkyl;

$R^4$ is selected from:
(1) hydrogen, and
(2) fluoro;

$R^5$ is —$C_{1-6}$alkyl, which is unsubstituted or substituted with:
(1) fluoro,
(2) hydroxy,
(3) —CN,
(4) keto,
(5) —$C_{1-6}$alkyl, which is unsubstituted or substituted with hydroxy, methoxy, fluoro, or —$C_{1-6}$alkyl-fluoro,
(6) —$C_{2-6}$alkenyl, which is unsubstituted or substituted with fluoro,
(7) —$OC_{1-6}$alkyl, which is unsubstituted or substituted with —$C_{1-6}$alkyl, hydroxy, methoxy, fluoro, or —$C_{1-6}$alkyl-fluoro,
(8) —$C_{3-4}$cycloalkyl or $C_{6-10}$cycloalkyl, which is unsubstituted or substituted with —$C_{1-6}$alkyl, hydroxy, methoxy, fluoro, or —$C_{1-6}$alkyl-fluoro,
(9) tetrahydrofuranyl, which is unsubstituted or substituted with —$C_{1-6}$alkyl, hydroxy, methoxy, or 1-3 fluoro,
(10) tetrahydropyranyl, which is unsubstituted or substituted with —$C_{1-6}$alkyl, hydroxy, methoxy, or 1-3 fluoro, and
(11) phenyl, which is unsubstituted or substituted with —$C_{1-6}$alkyl, hydroxy, methoxy, or 1-3 fluoro;

each of $R^8$, $R^9$, $R^{10}$ and $R^{11}$ is independently selected from:
(1) hydrogen,
(2) halogen,
(3) —$C_{1-6}$alkyl, which is unsubstituted or substituted with: hydroxy, —$OC_{1-6}$alkyl, cyclopropyl, cyclobutyl, or 1-3 fluoro; phenyl, which is unsubstituted or substituted with hydroxy, —$C_{1-6}$alkyl or fluoro; or pyridyl, which is unsubstituted or substituted with hydroxy, —$C_{1-6}$alkyl or fluoro,
(4) —$OC_{1-6}$alkyl, which is unsubstituted or substituted with a hydroxy, —$OC_{1-6}$alkyl, cyclopropyl, cyclobutyl, or 1-3 fluoro,
(5) —$C_{3-6}$cyclolkyl, which is unsubstituted or substituted with a hydroxy, methoxy, or 1-3 fluoro, and
(6) —CN;

or a pharmaceutically acceptable salt thereof.

2. The compound of claim 1 of the formula Ib:

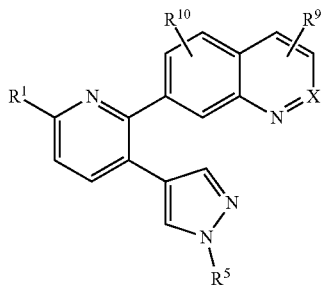

or a pharmaceutically acceptable salt thereof.

3. The compound of claim 1, or a pharmaceutically acceptable salt thereof, wherein $R^2$ is hydrogen, $R^3$ is hydrogen and $R^1$ is selected from:
(1) hydrogen,
(2) fluoro,
(3) chloro,
(4) —CN, and
(5) methyl.

4. The compound of claim 1, or a pharmaceutically acceptable salt thereof, wherein $R^5$ is —CH$_2$—, which is substituted with a group selected from:
(1) adamantyl,
(2) bicyclopentyl,
(3) bicyclooctyl,
(4) cyclobutyl, which is unsubstituted or substituted with —C$_{1-6}$alkyl or 1-3 fluoro,
(5) cyclopropyl, which is unsubstituted or substituted with —C$_{1-6}$alkyl or 1-3 fluoro,
(6) cyclohexyl, which is unsubstituted or substituted with —C$_{1-6}$alkyl or 1-3 fluoro,
(7) phenyl, which is unsubstituted or substituted with 1-3 fluoro;
(8) spiropentyl, and
(9) tetrahydrofuranyl, which is unsubstituted or substituted with —C$_{1-6}$alkyl or 1-3 fluoro.

5. The compound of claim 1, or a pharmaceutically acceptable salt thereof, wherein $R^5$ is —C$_{1-6}$alkyl, which is unsubstituted or substituted with fluoro, —OC$_{1-6}$alkyl, cyclopropyl, cyclobutyl, cyclohexyl, or phenyl.

6. The compound of claim 1 or a pharmaceutically acceptable salt thereof, wherein $R^5$ is —C$_{1-6}$alkyl, which is unsubstituted or substituted with fluoro.

7. The compound of claim 1 or a pharmaceutically acceptable salt thereof, wherein $R^5$ is selected from:
(1) 2,2-dimethylpropyl,
(2) 2,2-difluorobutyl,
(3) 3-methylbutyl,
(4) 3-fluoro-3-methylbutyl,
(5) neopentyl,
(6) 1-(methylcyclopentyl)methyl,
(7) 1-(fluorocyclopentyl)methyl,
(8) cyclopentyl-3,3,3-trifluoro-2,2-dimethylpropyl,
(9) 1-(cyclohexylmethyl), and
(10) (1-(trifluromethyl)cyclopropyl)methyl.

8. The compound of claim 1, or a pharmaceutically acceptable salt thereof, wherein each of $R^8$, $R^9$, $R^{10}$ and $R^{11}$ is independently selected from:
(1) hydrogen,
(2) halogen,
(3) —OH,
(4) —C$_{1-6}$alkyl, which is unsubstituted or substituted with a hydroxy, or 1-3 fluoro,
(5) —OC$_{1-6}$alkyl, which is unsubstituted or substituted with a hydroxy, or 1-3 fluoro, and
(6) cyclopropyl.

9. The compound of claim 1, or a pharmaceutically acceptable salt thereof, wherein each of $R^8$, $R^9$, $R^{10}$ and $R^{11}$ is independently selected from:
(1) hydrogen,
(2) fluoro,
(3) —CH$_3$,
(4) —CF$_3$, and
(5) —OCH$_3$, and
(6) cyclopropyl.

10. A compound which is selected from:
3-methoxy-7-(3-{1-[(1-methylcyclohexyl)methyl]-1H-pyrazol-4-yl}pyridin-2-yl)cinnoline;
7-(3-(1-(3-fluoro-3-methylbutyl)-1H-pyrazol-4-yl)-6-methylpyridin-2-yl)quinoline;
7-{3-[1-(3-fluoro-3-methylbutyl)-1H-pyrazol-4-yl]-6-methylpyridin-2-yl}-3-methoxycinnoline;
7-[3-(1-benzyl-1H-pyrazol-4-yl)-6-methylpyridin-2-yl] quinoline;
7-[3-(1-benzyl-1H-pyrazol-4-yl)-6-methylpyridin-2-yl]-3-methoxycinnoline;
7-{3-[1-(2,2-dimethylpropyl)-1H-pyrazol-4-yl]-6-methylpyridin-2-yl}quinoline;
7-(6-methyl-3-{1-[(1-methylcyclohexyl)methyl]-1H-pyrazol-4-yl}pyridin-2-yl)-3-(trifluoromethyl)quinoline;
7-{3-[1-(cyclobutylmethyl)-1H-pyrazol-4-yl]-6-methylpyridin-2-yl}-3-methoxycinnoline;
7-{3-[1-(bicyclo[1.1.1]pent-1-ylmethyl)-1H-pyrazol-4-yl]-6-methylpyridin-2-yl}quinoline;
7-{3-[1-(bicyclo[1.1.1]pent-1-ylmethyl)-1H-pyrazol-4-yl]-6-methylpyridin-2-yl}-3-methoxycinnoline;
7-{6-methyl-3-[1-(4,4,4-trifluoro-3-methylbutyl)-1H-pyrazol-4-yl]pyridin-2-yl}quinoline;
7-(3-(1-(((3r,5r,7r)-adamantan-1-yl)methyl)-1H-pyrazol-4-yl)-6-methylpyridin-2-yl)quinoline;
7-(3-(1-(((3r,5r,7r)-adamantan-1-yl)methyl)-1H-pyrazol-4-yl)-6-methylpyridin-2-yl)-3-methoxycinnoline;
7-{3-[1-(bicyclo[2.2.2]oct-1-ylmethyl)-1H-pyrazol-4-yl]-6-methylpyridin-2-yl}quinoline;
7-{3-[1-(bicyclo[2.2.2]oct-1-ylmethyl)-1H-pyrazol-4-yl]-6-methylpyridin-2-yl}-3-methoxycinnoline;
7-(3-{1-[(4,4-difluorocyclohexyl)methyl]-1H-pyrazol-4-yl}-6-methylpyridin-2-yl)quinoline;
7-(3-{1-[(4,4-difluorocyclohexyl)methyl]-1H-pyrazol-4-yl}-6-methylpyridin-2-yl)-3-methoxycinnoline;
7-(3-{1-[(4-fluorocyclohexyl)methyl]-1H-pyrazol-4-yl}-6-methylpyridin-2-yl)quinoline;
7-(3-{1-[(4-fluorocyclohexyl)methyl]-1H-pyrazol-4-yl}-6-methylpyridin-2-yl)-3-methoxycinnoline;
7-{3-[1-(2-fluorobenzyl)-1H-pyrazol-4-yl]-6-methylpyridin-2-yl}quinoline;
7-{3-[1-(2-fluorobenzyl)-1H-pyrazol-4-yl]-6-methylpyridin-2-yl}-3-methoxycinnoline;
7-(3-{1-[(4,4-difluoro-1-methylcyclohexyl)methyl]-1H-pyrazol-4-yl}-6-methylpyridin-2-yl)-3-methoxycinnoline;
3-methoxy-7-(6-methyl-3-{1-[(2-methyltetrahydrofuran-2-yl)methyl]-1H-pyrazol-4-yl}pyridin-2-yl)cinnoline;
3-methoxy-7-[6-methyl-3-(1-[1-(trifluoromethyl)cyclobutyl]methyl 1-1H-pyrazol-4-yl)pyridin-2-yl]cinnoline;

3-methoxy-7-(6-methyl-3-[1-[(1-methylcyclobutyl)methyl]-1H-pyrazol-4-yl]pyridin-2-yl)cinnoline;

3-methoxy-7-(6-methyl-3-[1-[(1-methylcyclopropyl)methyl]-1H-pyrazol-4-yl]pyridin-2-yl)cinnoline;

5-(1-{[1-(difluoromethyl)cyclopropyl]methyl}-1H-pyrazol-4-yl)-6-quinolin-7-ylpyridine-2-carbonitrile;

5-(1-{[1-(difluoromethyl)cyclopropyl]methyl}-1H-pyrazol-4-yl)-6-(3-methoxycinnolin-7-yl)pyridine-2-carbonitrile;

6-quinolin-7-yl-5-[1-(spiro[2.2]pent-1-ylmethyl)-1H-pyrazol-4-yl]pyridine-2-carbonitrile;

7-{6-chloro-3-[1-(3-methoxy-3-methylbutyl)-1H-pyrazol-4-yl]-5-methylpyridin-2-yl}-3-methoxycinnoline;

7-{6-chloro-3-[1-(2-methoxy-2-methylpropyl)-1H-pyrazol-4-yl]-5-methylpyridin-2-yl}-3-methoxycinnoline;

6-(3-methoxycinnolin-7-yl)-5-[1-(3-methoxy-3-methylbutyl)-1H-pyrazol-4-yl]-3-methylpyridine-2-carbonitrile;

6-(3-methoxycinnolin-7-yl)-5-[1-(2-methoxy-2-methylpropyl)-1H-pyrazol-4-yl]-3-methylpyridine-2-carbonitrile;

3-methoxy-7-{3-[1-(3-methoxy-3-methylbutyl)-1H-pyrazol-4-yl]-5,6-dimethylpyridin-2-yl}cinnoline;

3-methoxy-7-{3-[1-(2-methoxy-2-methylpropyl)-1H-pyrazol-4-yl]-5,6-dimethylpyridin-2-yl}cinnoline;

7-[3-fluoro-1-(3-fluoro-3-methylbutyl)-1H-pyrazol-4-yl]-6-methylpyridin-2-yl-3-methoxycinnoline;

5-[1-(2,2-dimethylpropyl)-1H-pyrazol-4-yl]-6-quinolin-7-ylpyridine-2-carbonitrile;

5-[1-(2,2-dimethylpropyl)-1H-pyrazol-4-yl]-6-(3-methoxycinnolin-7-yl)pyridine-2-carbonitrile;

5-[1-(2,2-dimethylpropyl)-1H-pyrazol-4-yl]-6-(2-methylquinolin-7-yl)pyridine-2-carbonitrile;

5-[1-(2,2-dimethylpropyl)-1H-pyrazol-4-yl]-6-(1,5-naphthyridin-3-yl)pyridine-2-carbonitrile;

5-[1-(2,2-dimethylpropyl)-1H-pyrazol-4-yl]-6-(3-fluoroquinolin-7-yl)pyridine-2-carbonitrile;

6-(3-chlorocinnolin-7-yl)-5-[1-(2,2-dimethylpropyl)-1H-pyrazol-4-yl]pyridine-2-carbonitrile;

6-cinnolin-7-yl-5-[1-(2,2-dimethylpropyl)-1H-pyrazol-4-yl]pyridine-2-carbonitrile;

6-quinolin-7-yl-5-(1-1 [1-(trifluoromethyl)cyclopropyl]methyl-1H-pyrazol-4-yl)pyridine-2-carbonitrile;

6-(3-methoxycinnolin-7-yl)-5-(1-1 [1-(trifluoromethyl)cyclopropyl]methyl 1-1H-pyrazol-4-yl)pyridine-2-carbonitrile;

5-[1-(2-hydroxy-3-methylbutyl)-1H-pyrazol-4-yl]-6-quinolin-7-ylpyridine-2-carbonitrile;

3-fluoro-6-quinolin-7-yl-5-(1-{[1-(trifluoromethyl)cyclopropyl]methyl}-1H-pyrazol-4-yl)pyridine-2-carbonitrile;

7-{6-methoxy-3-[1-(3-methylbutyl)-1H-pyrazol-4-yl]pyridin-2-yl}quinoline;

7-{3-[1-(3-methylbutyl)-1H-pyrazol-4-yl]-6-(trifluoromethyl)pyridin-2-yl}quinoline;

7-{4-methyl-3-[1-(3-methylbutyl)-1H-pyrazol-4-yl]pyridin-2-yl}quinoline;

7-{4-methoxy-3-[1-(3-methylbutyl)-1H-pyrazol-4-yl]pyridin-2-yl}quinoline;

7-{5-chloro-3-[1-(3-methylbutyl)-1H-pyrazol-4-yl]pyridin-2-yl}quinoline;

7-{5-chloro-3-[1-(3-methylbutyl)-1H-pyrazol-4-yl]pyridin-2-yl}-3-methoxycinnoline;

7-{6-(difluoromethyl)-3-[1-(2,2-dimethylpropyl)-1H-pyrazol-4-yl]pyridin-2-yl}-3-methoxycinnoline;

7-{3-[1-(2,2-dimethylpropyl)-1H-pyrazol-4-yl]-5-fluoropyridin-2-yl}quinoline;

2-methyl-6-quinolin-7-yl-5-(1-{[1-(trifluoromethyl)cyclopropyl]methyl}-1H-pyrazol-4-ylpyridine-3-carbonitrile;

6-(3-methoxycinnolin-7-yl)-2-methyl-5-(1-{[1-(trifluoromethyl)cyclopropyl]methyl}-1H-pyrazol-4-ylpyridine-3-carbonitrile;

5-[1-(2,2-dimethylpropyl)-5-fluoro-1H-pyrazol-4-yl]-6-quinolin-7-ylpyridine-2-carbonitrile;

5-(5-fluoro-1-{[1-(trifluoromethyl)cyclopropyl]methyl}-1H-pyrazol-4-yl)-6-quinolin-7-ylpyridine-2-carbonitrile;

5-[1-(3-methyl-2-oxobutyl)-1H-pyrazol-4-yl]-6-quinolin-7-ylpyridine-2-carbonitrile;

5-[1-(2,2-difluoro-3-methylbutyl)-1H-pyrazol-4-yl]-6-quinolin-7-ylpyridine-2-carbonitrile;

2-chloro-7-{3-[1-(3-methylbutyl)-1H-pyrazol-4-yl]pyridin-2-yl}quinoline;

7-{6-chloro-3-[1-(3-methylbutyl)-1H-pyrazol-4-yl]pyridin-2-yl}quinoline;

7-{4-chloro-3-[1-(3-methylbutyl)-1H-pyrazol-4-yl]pyridin-2-yl}quinoline;

7-{6-fluoro-3-[1-(3-methylbutyl)-1H-pyrazol-4-yl]pyridin-2-yl}quinoline;

5-[1-(3-methylbutyl)-1H-pyrazol-4-yl]-6-quinolin-7-ylpyridine-2-carbonitrile;

7-{6-(3,6-dihydro-2H-pyran-4-yl)-3-[1-(3-methylbutyl)-1H-pyrazol-4-yl]pyridin-2-yl}quinoline;

7-{3-[1-(3-methylbutyl)-1H-pyrazol-4-yl]-6-(1-methyl-1H-pyrazol-5-yl)pyridin-2-yl}quinoline;

7-{3-[1-(3-methylbutyl)-1H-pyrazol-4-yl]-6-propylpyridin-2-yl}quinoline;

7-{6-(cyclopropyl)-3-[1-(3-methylbutyl)-1H-pyrazol-4-yl]pyridin-2-yl}quinoline;

7-{5-methyl-3-[1-(3-methylbutyl)-1H-pyrazol-4-yl]pyridin-2-yl}quinoline;

7-{6-ethenyl-3-[1-(3-methylbutyl)-1H-pyrazol-4-yl]pyridin-2-yl}quinoline;

7-{6-ethyl-3-[1(3-methylbutyl)-1H-pyrazol-4-yl]pyridin-2-yl}quinoline;

7-{6-bromo-3-[1-(3-methylbutyl)-1H-pyrazol-4-yl]pyridin-2-yl}quinoline;

7-{6-(2-methoxyethoxy)-3-[1-(3-methylbutyl)-1H-pyrazol-4-yl]pyridin-2-yl}quinoline;

7-{3-[1-(3-methylbutyl)-1H-pyrazol-4-yl]-5-(methyl sulfanyl)pyridin-2-yl}quinoline;

3-methoxy-7-{6-methyl-3-[1-(4,4,4-trifluorobutyl)-1H-pyrazol-4-yl]pyridin-2-yl}cinnoline;

7-(3-{1-[(3,3-difluorocyclobutyl)methyl]-1H-pyrazol-4-yl}-6-methylpyridin-2-yl)-3-methoxycinnoline;

7-(3-{1-[2-(3,3-difluorocyclobutyl)ethyl]-1H-pyrazol-4-yl}-6-methylpyridin-2-yl)-3-methoxycinnoline;

3-methoxy-7-{6-methyl-3-[1-(4,5,5-trifluoropent-4-en-1-yl)-1H-pyrazol-4-yl]pyridin-2-yl}cinnoline;

3-methoxy-7-(6-methyl-3-{1-[2-(tetrahydrofuran-3-yl)ethyl]-1H-pyrazol-4-yl}pyridin-2-yl)cinnoline;

3-methoxy-7-{6-methyl-3-[1-(tetrahydrofuran-3-ylmethyl)-1H-pyrazol-4-yl]pyridin-2-yl}cinnoline;

3-methoxy-7-{6-methyl-3-[1-(spiro[3.3]hept-2-ylmethyl)-1H-pyrazol-4-yl]pyridin-2-yl}cinnoline;

3-{4-[2-(3-methoxycinnolin-7-yl)-6-methylpyridin-3-yl]-1H-pyrazol-1-yl}-2,2-dimethylpropanenitrile;

4-{4-[2-(3-methoxycinnolin-7-yl)-6-methylpyridin-3-yl]-1H-pyrazol-1-yl}-2,2-dimethylbutanenitrile;

7-(3-{1-[(1-fluorocyclohexyl)methyl]-1H-pyrazol-4-yl}-6-methylpyridin-2-yl)-3-methoxycinnoline;

3-methoxy-7-(6-methyl-3-{1-[(4-methyltetrahydro-2H-pyran-4-yl)methyl]-1H-pyrazol-4-yl}pyridin-2-yl)cinnoline;

6-quinolin-7-yl-5-[1-(3,3,3-trifluoro-2,2-dimethylpropyl)-1H-pyrazol-4-yl]pyridine-2-carbonitrile;

5-[1-(3,3-dimethylbutyl)-1H-pyrazol-4-yl]-6-quinolin-7-ylpyridine-2-carbonitrile;

5-[1-(3,3-difluoro-2,2-dimethylpropyl)-1H-pyrazol-4-yl]-6-quinolin-7-ylpyridine-2-carbonitrile;

6-quinolin-7-yl-5-[1-(4,4,4-trifluoro-3,3-dimethylbutyl)-1H-pyrazol-4-yl]pyridine-2-carbonitrile;

6-quinolin-7-yl-5-[1-(2,2,3,3-tetrafluoropropyl)-1H-pyrazol-4-yl]pyridine-2-carbonitrile;

7-(3-{1-[(4,4-difluoro-1-methylcyclohexyl)methyl]-1H-pyrazol-4-yl}-6-methylpyridin-2-yl)quinoline;

7-(3-{1-[(1-methylcyclohexyl)methyl]-1H-pyrazol-4-yl}pyridin-2-yl)quinoline;

7-{3-[1-(2-cyclobutylethyl)-1H-pyrazol-4-yl]pyridin-2-yl}quinoline;

7-{3-[1-(2-cyclopropylethyl)-1H-pyrazol-4-yl]pyridin-2-yl}quinoline;

5-{1-[(1-methylcyclopropyl)methyl]-1H-pyrazol-4-yl}-6-quinolin-7-ylpyridine-2-carbonitrile;

3-methoxy-7-(6-methyl-3-{1-[(3-methyltetrahydrofuran-3-yl)methyl]-1H-pyrazol-4-yl}pyridin-2-yl)cinnoline;

7-(3-{1-[(2,2-dimethyl cyclopropyl)methyl]-1H-pyrazol-4-yl}-6-methylpyridin-2-yl)-3-methoxycinnoline;

7-(3-{1-[(2,2-dimethylcyclopropyl)methyl]-1H-pyrazol-4-yl}-6-methylpyridin-2-yl)quinoline;

5-{1-[(2,2-dimethylcyclopropyl)methyl]-1H-pyrazol-4-yl}-6-(3-methoxycinnolin-7-yl)pyridine-2-carbonitrile;

5-{1-[(2,2-dimethylcyclopropyl)methyl]-1H-pyrazol-4-yl}-6-quinolin-7-ylpyridine-2-carbonitrile;

5-{1-[1-(cyanomethyl)cyclopropyl]methyl-1H-pyrazol-4-yl}-6-(3-methoxycinnolin-7-yl)pyridine-2-carbonitrile;

5-{1-[1-(cyanomethyl)cyclopropyl]methyl-1H-pyrazol-4-yl}-6-quinolin-7-ylpyridine-2-carbonitrile;

7-{3-[1-(cyclohexylmethyl)-1H-pyrazol-4-yl]pyridin-2-yl}quinoline;

7-{3-[1-(cyclohexylmethyl)-1H-pyrazol-4-yl]-6-methylpyridin-2-yl}-3-methoxycinnoline;

7-{3-[1-(4,4-difluorocyclohexyl)-1H-pyrazol-4-yl]-6-methylpyridin-2-yl}-3-methoxycinnoline;

7-{6-(difluoromethyl)-3-[1-(2,2-dimethylpropyl)-1H-pyrazol-4-yl]pyridin-2-yl}quinoline;

5-[1-(2-methylpropyl)-1H-pyrazol-4-yl]-6-quinolin-7-ylpyridine-2-carbonitrile;

5-{1-[(1-fluorocyclopropyl)methyl]-1H-pyrazol-4-yl}-6-quinolin-7-ylpyridine-2-carbonitrile;

6-(3-methoxycinnolin-7-yl)-5-[1-(2,2,3,3,3-pentafluoropropyl)-1H-pyrazol-4-yl]pyridine-2-carbonitrile;

5-[1-(3-hydroxy-2,2-dimethylpropyl)-1H-pyrazol-4-yl]-6-quinolin-7-ylpyridine-2-carbonitrile;

7-{3-[1-(2-fluoro-2-methylpropyl)-1H-pyrazol-4-yl]-6-methylpyridin-2-yl}-3-methoxycinnoline;

7-{6-(difluoromethyl)-3-[1-(2-fluoro-2-methylpropyl)-1H-pyrazol-4-yl]pyridin-2-yl}-3-methoxycinnoline;

5-{1-[(1-fluorocyclobutyl)methyl]-1H-pyrazol-4-yl}-6-quinolin-7-ylpyridine-2-carbonitrile; and 5-[1-(2,2-difluoro-3-hydroxy-3-methylbutyl)-1H-pyrazol-4-yl]-6-quinolin-7-ylpyridine-2-carbonitrile;

or a pharmaceutically acceptable salt thereof.

11. A pharmaceutical composition which comprises an inert carrier and a compound of claim 1 or a pharmaceutically acceptable salt thereof.

12. A method for the treatment of a neurological and/or psychiatric disorder associated with muscarinic acetylcholine receptor dysfunction in a mammal comprising the step of administering at least one compound of claim 1, or a pharmaceutically acceptable salt of said compound, to a patient in need thereof in an amount effective to treat said disorder.

13. The method of claim 12, wherein the mammal has been diagnosed with a need for treatment of the disorder prior to the administering step.

14. The method of claim 12, wherein the disorder is a neurological and/or psychiatric disorder associated with mAChR M4 dysfunction.

15. The method of claim 12, wherein the disorder is a psychotic disorder.

16. The method of claim 15, wherein the psychotic disorder is selected from schizophrenia, psychotic disorder, brief psychotic disorder, schizophreniform disorder, schizoaffective disorder, delusional disorder, shared psychotic disorder, catastrophic schizophrenia, postpartum psychosis, psychotic depression, psychotic break, tardive psychosis, myxedematous psychosis, occupational psychosis, menstrual psychosis, secondary psychotic disorder, bipolar I disorder with psychotic features, and substance-induced psychotic disorder.

17. The method of claim 12, wherein the disorder is a cognitive disorder.

18. The method of claim 17, wherein the cognitive disorder is selected from amnesia, dementia, delirium, amnestic disorder, substance-induced persisting delirium, dementia due to HIV disease, dementia due to Huntington's disease, dementia due to Parkinson's disease, Parkinsonian-ALS dementia complex, dementia of the Alzheimer's type, age-related cognitive decline, and mild cognitive impairment.

* * * * *